(12) United States Patent
Morgan et al.

(10) Patent No.: US 7,491,826 B2
(45) Date of Patent: *Feb. 17, 2009

(54) COMPOUNDS, COMPOSITIONS AND METHODS

(75) Inventors: Bradley Paul Morgan, Moraga, CA (US); Kathleen A. Elias, San Francisco, CA (US); Erica Anne Kraynack, Belmont, CA (US); Pu-Ping Lu, Foster City, CA (US); Fady Malik, Burlingame, CA (US); Alex Muci, San Francisco, CA (US); Xiangping Qian, Foster City, CA (US); Whitney Walter Smith, El Cerrito, CA (US); Todd Tochimoto, Foster City, CA (US); Adam Lewis Tomasi, San Francisco, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 427 days.

This patent is subject to a terminal disclaimer.

(21) Appl. No.: 10/890,829

(22) Filed: Jul. 14, 2004

(65) Prior Publication Data

US 2005/0159416 A1    Jul. 21, 2005

Related U.S. Application Data

(63) Continuation-in-part of application No. PCT/US2004/001069, filed on Jan. 14, 2004.

(60) Provisional application No. 60/501,376, filed on Sep. 8, 2003, provisional application No. 60/476,517, filed on Jun. 5, 2003, provisional application No. 60/476,086, filed on Jun. 4, 2003, provisional application No. 60/440,183, filed on Jan. 14, 2003, provisional application No. 60/440,133, filed on Jan. 14, 2003.

(51) Int. Cl.
*C07D 211/68* (2006.01)
*C07D 401/04* (2006.01)
*C07D 401/14* (2006.01)

(52) U.S. Cl. ................... 546/194; 546/274.1

(58) Field of Classification Search ............... 544/124; 546/278.1, 309, 216, 194, 271.4; 548/530; 549/42

See application file for complete search history.

(56) References Cited

U.S. PATENT DOCUMENTS

| | | |
|---|---|---|
| 3,907,782 A | 9/1975 | Edwards |
| 3,939,169 A | 2/1976 | Edwards |
| 5,162,360 A | 11/1992 | Creswell et al. |
| 5,547,966 A | 8/1996 | Atwal et al. |
| 5,624,937 A | 4/1997 | Reel et al. |
| 5,919,811 A | 7/1999 | Conti et al. |
| 5,962,483 A | 10/1999 | Warrellow et al. |
| 5,972,975 A | 10/1999 | Esser et al. |
| 6,001,860 A | 12/1999 | Hamanaka |
| 6,174,905 B1 | 1/2001 | Suzuki et al. |
| 6,207,809 B1 | 3/2001 | Nestler |
| 6,262,083 B1 | 7/2001 | Moon et al. |
| 6,329,395 B1 | 12/2001 | Dugar et al. |
| 6,573,264 B1 | 6/2003 | Zablocki et al. |
| 6,645,990 B2 | 11/2003 | Askew et al. |
| 6,656,971 B2 | 12/2003 | Wu et al. |
| 6,670,376 B1 | 12/2003 | Moran et al. |
| 6,696,576 B2 | 2/2004 | Baumann et al. |
| 7,176,222 B2 * | 2/2007 | Morgan et al. ............... 514/318 |
| 2002/0165394 A1 * | 11/2002 | Dumas et al. ................ 546/143 |
| 2003/0045552 A1 | 3/2003 | Robarge et al. |
| 2003/0207872 A1 | 11/2003 | Riedl et al. |
| 2004/0229937 A1 | 11/2004 | Dumas et al. |
| 2004/0235829 A1 | 11/2004 | Scott et al. |
| 2005/0032798 A1 | 2/2005 | Boyer et al. |
| 2005/0038031 A1 | 2/2005 | Dumas et al. |
| 2005/0059703 A1 | 3/2005 | Wilhelm et al. |
| 2006/0014761 A1 | 1/2006 | Morgan et al. |
| 2006/0025470 A1 | 2/2006 | Morgan et al. |
| 2006/0241110 A1 | 10/2006 | Morgan et al. |
| 2007/0066626 A1 | 3/2007 | Morgan et al. |
| 2007/0195704 A1 | 8/2007 | Morgan et al. |
| 2007/0197505 A1 | 8/2007 | Morgan et al. |

FOREIGN PATENT DOCUMENTS

| | | | |
|---|---|---|---|
| DE | 3147879 | * | 6/1983 |
| EP | 27965 | * | 10/1980 |
| EP | 81142 | * | 6/1983 |

(Continued)

OTHER PUBLICATIONS

Jeffcoat et al. STN Accession No. 1977:462295; Document No. 87:62295 Abstract of Drug Metabolism and Disposition (1977), 5(2), 157-66).*

(Continued)

*Primary Examiner*—D. Margaret Seaman
*Assistant Examiner*—Nizal S Chandrakumar
(74) *Attorney, Agent, or Firm*—Finnegan, Henderson, Farabow, Garrett & Dunner, LLP

(57) ABSTRACT

Certain substituted urea derivatives selectively modulate the cardiac sarcomere, for example by potentiating cardiac myosin, and are useful in the treatment of systolic heart failure including congestive heart failure.

8 Claims, No Drawings

FOREIGN PATENT DOCUMENTS

| | | | |
|---|---|---|---|
| EP | 0 656 350 A1 | | 6/1995 |
| GB | 921682 | * | 8/1960 |
| JP | 11-302173 | | 11/1999 |
| JP | 2000-256194 | | 9/2000 |
| JP | 2002-220338 | | 8/2002 |
| NZ | 240935 | | 11/1994 |
| WO | WO 92/10468 | | 6/1992 |
| WO | WO 93/14074 A1 | | 7/1993 |
| WO | WO 96/10559 A1 | | 4/1996 |
| WO | WO 9932111 | * | 12/1997 |
| WO | WO 9850346 | * | 1/1998 |
| WO | WO 98/50346 A2 | | 11/1998 |
| WO | WO 98/52558 A1 | | 11/1998 |
| WO | WO 98/52559 A1 | | 11/1998 |
| WO | WO 99/32106 A1 | | 7/1999 |
| WO | WO 99/32436 A1 | | 7/1999 |
| WO | WO 99/32463 A1 | | 7/1999 |
| WO | WO 99/64394 A1 | | 12/1999 |
| WO | WO 00/41698 A1 | | 7/2000 |
| WO | WO 01/25190 A1 | | 4/2001 |
| WO | WO 0153274 A1 | * | 7/2001 |
| WO | WO 02/00626 A1 | | 1/2002 |
| WO | WO 02/00632 A1 | | 1/2002 |
| WO | WO 02/06246 A1 | | 1/2002 |
| WO | WO 02/14311 A2 | | 2/2002 |
| WO | WO 02/059106 A1 | | 8/2002 |
| WO | WO 02/062763 A2 | | 8/2002 |
| WO | WO 02/064576 A1 | | 8/2002 |
| WO | WO 02/070462 A1 | | 9/2002 |
| WO | WO 02085857 A2 | * | 10/2002 |
| WO | WO 02/092576 A1 | | 11/2002 |
| WO | WO 03/007942 A1 | | 1/2003 |
| WO | WO 03/013523 A1 | | 2/2003 |
| WO | WO 03/022820 A1 | | 3/2003 |
| WO | WO 03/024933 A1 | | 3/2003 |
| WO | WO 03/042164 A1 | | 5/2003 |
| WO | WO 03/059258 A2 | | 7/2003 |
| WO | WO 03/062224 A1 | | 7/2003 |
| WO | WO 03/062235 A1 | | 7/2003 |
| WO | WO 03/074501 A1 | | 9/2003 |
| WO | WO 03/082278 A1 | | 10/2003 |
| WO | WO 03/082808 A1 | | 10/2003 |
| WO | WO 03/082861 A2 | | 10/2003 |
| WO | WO 03/088967 A1 | | 10/2003 |
| WO | WO 03/091229 A1 | | 11/2003 |
| WO | WO 03/093250 A2 | | 11/2003 |
| WO | WO 03/097576 A2 | | 11/2003 |
| WO | WO 04/000831 A1 | | 12/2003 |
| WO | WO 2004/002481 A1 | | 1/2004 |
| WO | WO 2004/013102 A1 | | 2/2004 |
| WO | WO 2004/013132 A1 | | 2/2004 |
| WO | WO 2004/019958 A1 | | 3/2004 |
| WO | WO 2004/024729 A1 | | 3/2004 |
| WO | WO 2004/039306 A2 | | 5/2004 |

OTHER PUBLICATIONS

Office Action mailed Jun. 22, 2006, for U.S. Appl. No. 11/032,227, filed Jan. 11, 2005.
Notice of Allowance mailed Oct. 18, 2006, for U.S. Appl. No. 11/032,227, filed Jan. 11, 2005.
International Search Report and Written Opinion mailed Jan. 14, 2005, for Application No. PCT/US04/01069, filed Jan. 14, 2004.
Office Action mailed Sep. 7, 2007, for U.S. Appl. No. 10/541,596, filed Apr. 25, 2006.
Kempter et al., STN Accession No. 1984:510849; Document No. 101:110849 (1983).
El-Sharief et al., STN Accession No. 1987:549199; Document No. 107:14919 (1987).
Supplementary Partial European Search Report dated Aug. 2, 2007, for EP 04702228.0 - 1211, filed Aug. 5, 2005.
International Search Report and Written Opinion for International Application No. PCT/US05/21100, mailed Aug. 2, 2006, 10 pages.
Notice of Allowance mailed Dec. 21, 2007, for U.S. Appl. No. 10/541,596, filed Apr. 25, 2006.
Office Action mailed Mar. 20, 2008 for U.S. Appl. No. 11/498,986, filed Aug. 4, 2006.
Examiner Search Strategy and Results mailed Mar. 20, 2008 for U.S. Appl. No. 11/498,986, filed Aug. 4, 2006.
Office Action mailed Oct. 12, 2007 for U.S. Appl. No. 11/155,940, filed Jun. 16, 2005.
Jeffcoat et al., Drug Metabolism and Disposition 5(2):157-166.
Mizukura et al., STN Accession No.: 113:106314; Original Reference No.: 113:17823a, 17826a (1990).

* cited by examiner

COMPOUNDS, COMPOSITIONS AND METHODS

CROSS-REFERENCE TO RELATED APPLICATIONS

This application is a continuation-in-part of co-pending International Application PCT/US 2004/001069, with an international filing date of Jan. 14, 2004; which claims the benefit of provisional U.S. Applications Ser. Nos. 60/440,133 and 60/440,183 filed Jan. 14, 2003; 60/476,086 filed Jun. 4, 2003; 60/476,517 filed Jun. 5, 2003; and 60/501,376 filed Sep. 8, 2003; each incorporated herein by reference.

FIELD OF THE INVENTION

The invention relates to substituted urea derivatives, particularly to compounds that selectively modulate the cardiac sarcomere, and specifically to compounds, pharmaceutical formulations and methods of treatment for systolic heart failure, including congestive heart failure.

BACKGROUND OF THE INVENTION

The Cardiac Sarcomere

The "sarcomere" is an elegantly organized cellular structure found in cardiac and skeletal muscle made up of inter-digitating thin and thick filaments; it comprises nearly 60% of cardiac cell volume. The thick filaments are composed of "myosin," the protein responsible for transducing chemical energy (ATP hydrolysis) into force and directed movement. Myosin and its functionally related cousins are called motor proteins. The thin filaments are composed of a complex of proteins. One of these proteins, "actin" (a filamentous polymer) is the substrate upon which myosin pulls during force generation. Bound to actin are a set of regulatory proteins, the "troponin complex" and "tropomyosin," which make the actin-myosin interaction dependent on changes in intracellular $Ca^{2+}$ levels. With each heartbeat, $Ca^{2+}$ levels rise and fall, initiating cardiac muscle contraction and then cardiac muscle relaxation (Robbins J and Leinwand L A. (1999) *Molecular Basis of Cardiovascular Disease*, Chapter 8. editor Chien, K. R., W. B. Saunders, Philadelphia). Each of the components of the sarcomere contributes to its contractile response.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes (Goodson H V and Spudich J A. (1993) Proc. Natl. Acad. Sci. USA 90: 659-663). Myosin-II consists of two globular head domains linked together by a long alpha-helical coiled-coiled tail that assembles with other myosin-IIs to form the core of the sarcomere's thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound (Spudich J A. (2001) Nat Rev Mol Cell Biol. 2(5):387-92). Un-binding of the globular head from the actin filament (also $Ca^{2+}$ modulated) coupled with return of the catalytic domain and light chain to their starting conformation/orientation completes the contraction and relaxation cycle.

Mammalian heart muscle consists of two forms of cardiac myosin, alpha and beta, and they are well characterized (Robbins, supra). The beta form is the predominant form (>90 percent) in adult human cardiac muscle. Both have been observed to be regulated in human heart failure conditions at both transcriptional and translational levels (Miyata supra), with the alpha form being down-regulated in heart failure.

The sequences of all of the human skeletal, cardiac, and smooth muscle myosins have been determined. While the cardiac alpha and beta myosins are very similar (93% identity), they are both considerably different from human smooth muscle (42% identity) and more closely related to skeletal myosins (80% identity). Conveniently, cardiac muscle myosins are incredibly conserved across mammalian species. For example, both alpha and beta cardiac myosins are >96% conserved between humans and rats, and the available 250-residue sequence of porcine cardiac beta myosin is 100% conserved with the corresponding human cardiac beta myosin sequence. Such sequence conservation contributes to the predictability of studying myosin based therapeutics in animal based models of heart failure.

The components of the cardiac sarcomere present targets for the treatment of heart failure, for example by increasing contractility or facilitating complete relaxation to modulate systolic and diastolic function, respectively.

Heart Failure

Congestive heart failure ("CHF") is not a specific disease, but rather a constellation of signs and symptoms, all of which are caused by an inability of the heart to adequately respond to exertion by increasing cardiac output. The dominant pathophysiology associated with CHF is systolic dysfunction, an impairment of cardiac contractility (with a consequent reduction in the amount of blood ejected with each heartbeat). Systolic dysfunction with compensatory dilation of the ventricular cavities results in the most common form of heart failure, "dilated cardiomyopathy," which is often considered to be one in the same as CHF. The counterpoint to systolic dysfunction is diastolic dysfunction, an impairment of the ability to fill the ventricles with blood, which can also result in heart failure even with preserved left ventricular function. Congestive heart failure is ultimately associated with improper function of the cardiac myocyte itself, involving a decrease in its ability to contract and relax.

Many of the same underlying conditions can give rise to systolic and/or diastolic dysfunction, such as atherosclerosis, hypertension, viral infection, valvular dysfunction, and genetic disorders. Patients with these conditions typically present with the same classical symptoms: shortness of breath, edema and overwhelming fatigue. In approximately half of the patients with dilated cardiomyopathy, the cause of their heart dysfunction is ischemic heart disease due to coronary atherosclerosis. These patients have had either a single myocardial infarction or multiple myocardial infarctions; here, the consequent scarring and remodeling results in the development of a dilated and hypocontractile heart. At times the causative agent cannot be identified, so the disease is referred to as "idiopathic dilated cardiomyopathy." Irrespective of ischemic or other origin, patients with dilated cardiomyopathy share an abysmal prognosis, excessive morbidity and high mortality.

The prevalence of CHF has grown to epidemic proportions as the population ages and as cardiologists have become more successful at reducing mortality from ischemic heart disease, the most common prelude to CHF. Roughly 4.6 million people in the United States have been diagnosed with CHF; the incidence of such diagnosis is approaching 10 per 1000 after 65 years of age. Hospitalization for CHF is usually the result of inadequate outpatient therapy. Hospital discharges for CHF rose from 377,000 (in 1979) to 957,000 (in 1997) making CHF the most common discharge diagnosis in people age 65 and over. The five-year mortality from CHF approaches 50% (Levy D. (2002) New Engl J. Med. 347(18): 1442-4). Hence, while therapies for heart disease have greatly improved and life expectancies have extended over the last several years, new and better therapies continue to be sought, particularly for CHF.

"Acute" congestive heart failure (also known as acute "decompensated" heart failure) involves a precipitous drop in heart function resulting from a variety of causes. For example in a patient who already has congestive heart failure, a new myocardial infarction, discontinuation of medications, and dietary indiscretions may all lead to accumulation of edema fluid and metabolic insufficiency even in the resting state. A therapeutic agent that increases heart function during such an acute episode could assist in relieving this metabolic insufficiency and speeding the removal of edema, facilitating the return to the more stable "compensated" congestive heart failure state. Patients with very advanced congestive heart failure particularly those at the end stage of the disease also could benefit from a therapeutic agent that increases heart function, for example, for stabilization while waiting for a heart transplant. Other potential benefits could be provided to patients coming off a bypass pump, for example, by administration of an agent that assists the stopped or slowed heart in resuming normal function. Patients who have diastolic dysfunction (insufficient relaxation of the heart muscle) could benefit from a therapeutic agent that modulates relaxation.

Therapeutic Active Agents

Inotropes are drugs that increase the contractile ability of the heart. As a group, all current inotropes have failed to meet the gold standard for heart failure therapy, i.e., to prolong patient survival. In addition, current agents are poorly selective for cardiac tissue, in part leading to recognized adverse effects that limit their use. Despite this fact, intravenous inotropes continue to be widely used in acute heart failure (e.g., to allow for reinstitution of oral medications or to bridge patients to heart transplantation) whereas in chronic heart failure, orally given digoxin is used as an inotrope to relieve patient symptoms, improve the quality of life, and reduce hospital admissions.

Given the limitations of current agents, new approaches are needed to improve cardiac function in congestive heart failure. The most recently approved short-term intravenous agent, milrinone, is now nearly fifteen years old. The only available oral drug, digoxin, is over 200 hundred years old. There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes.

The selectivity of agents directed at the cardiac sarcomere (for example, by targeting cardiac beta myosin) has been identified as an important means to achieve this improved therapeutic index. The present invention provides such agents (particularly sarcomere activating agents) and methods for their identification and use.

SUMMARY OF THE INVENTION

The present invention provides compounds, pharmaceutical compositions and methods for the treatment of heart failure including CHF, particularly systolic heart failure. The compositions are selective modulators of the cardiac sarcomere, for example, potentiating cardiac myosin.

In one aspect, the invention relates to one or more compounds of the group represented by Formula I:

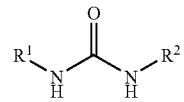

Formula I wherein:
$R^1$ is optionally substituted aryl or optionally substituted heteroaryl; and
$R^2$ is optionally substituted aryl, optionally substituted aralkyl; optionally substituted cycloalkyl, optionally substituted heteroaryl, optionally substituted heteroaralkyl or optionally substituted heterocyclyl, including single stereoisomers, mixtures of stereoisomers, and the pharmaceutically acceptable salts, solvates, and solvates of pharmaceutically acceptable salts thereof. The compounds of Formula I are useful as active agents in practice of the methods of treatment and in manufacture of the pharmaceutical formulations of the invention, and as intermediates in the synthesis of such active agents.

In a preferred aspect, the invention relates to one or more compounds of Formula I, where $R^1$ is represented by Formula II:

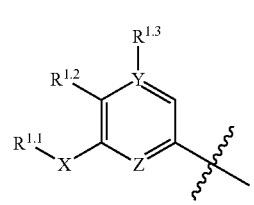

Formula II in which:
X is —O—, —O-(optionally substituted lower alkylene)-, -(optionally substituted lower alkylene)-O—, —S—, —S-(optionally substituted lower alkylene)-, -(optionally substituted lower alkylene)-S—, —SO$_2$—, —SO$_2$— (optionally substituted lower alkylene)-, or -(optionally substituted lower alkylene)-SO$_2$—;
Y and Z are independently —C═ or —N═, provided that only one of Y or Z is —N═;
$R^{1.1}$ is optionally substituted aryl, optionally substituted heteroaryl or optionally substituted heterocyclyl;
$R^{1.2}$ is hydrogen, halo or optionally substituted heteroaryl; and
$R^{1.3}$ is hydrogen, halo, optionally substituted heteroaryl or nitro.

Further preferred are the foregoing compounds where $R^2$ is optionally substituted pyridinyl, particularly pyridin-3-yl or 6-methyl-pyridin-3-yl, especially the compounds represented by Formula III:

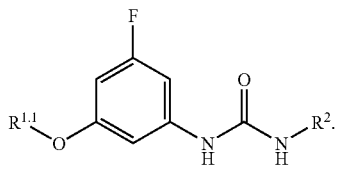

Formula III

In another preferred aspect, the invention relates to one or more compounds of Formula I where $R^1$ is represented by Formula II, having one or more of the following:

X is —O—;

Y and Z are —C═;

$R^{1.1}$ is tetrahydrofuranyl, tetrahydropyranyl, optionally substituted pyrrolidinyl, optionally substituted 3-oxo-tetrahydro-pyrrolo[1,2-c]oxazol-6-yl, optionally substituted morpholinyl, optionally substituted piperidinyl, optionally substituted pyridinyl or optionally substituted phenyl;

$R^{1.2}$ is hydrogen or fluoro; and $R^{1.3}$ is pyridinyl or fluoro.

In a further preferred aspect, the invention relates to one or more compounds of Formula I where $R^1$ is represented by Formula II and $R^{1.1}$ is 1-acyl-pyrrolidin-3-yl, 1-alkoxycarbonyl-pyrrolidin-3-yl, 1-amidino-pyrrolidin-3-yl, 1-sulfonyl-pyrrolidin-3-yl, 3-oxo-tetrahydro-pyrrolo[1,2-c]oxazol-6-yl, 1-acyl-piperidin-3-yl, 1-alkoxycarbonyl-piperidin-3-yl, 1-amidino-piperidin-3-yl or 1-sulfonyl-piperidin-3-yl, optionally having an additional lower alkoxy or lower alkoxyalkyl ring substituent.

In another aspect, the invention relates to compounds of the group represented by Formula I, where $R^2$ is optionally substituted aryl or optionally substituted heteroaryl, including single stereoisomers, mixtures of stereoisomers, and the pharmaceutically acceptable salts, solvates, and solvates of pharmaceutically acceptable salts thereof, particularly those where $R^2$ is:

optionally substituted phenyl, optionally substituted naphthyl, optionally substituted pyrrolyl, optionally substituted, thiazolyl, optionally substituted isooxazolyl, optionally substituted pyrazolyl, optionally substituted pyridinyl, optionally substituted pyrazinyl, optionally substituted pyrimidinyl or optionally substituted pyridazinyl.

Still another aspect of the invention relates to compounds of the group represented by Formula I, where $R^2$ is optionally substituted aralkyl; optionally substituted cycloalkyl, optionally substituted heteroaralkyl or optionally substituted heterocyclyl, including single stereoisomers, mixtures of stereoisomers, and the pharmaceutically acceptable salts, solvates, and solvates of pharmaceutically acceptable salts thereof, particularly those where:

$R^2$ is tetrahydrofuran-2-yl, tetrahydrofuran-3-yl, N-acetyl-pyrrolidin-2-yl, N-acetyl-morpholin-3-yl, N-acyl-piperidin-3-yl, N-acyl-piperidin-4-yl or cyclohexyl, or $R^2$ is represented by the formula —W—$R^{2.1}$ where:

W is $C_1$ to $C_3$ straight or branched-chain optionally substituted alkylene; and $R^{2.1}$ is optionally substituted tetrahydrofuranyl, optionally substituted tetrahydropyranyl, optionally substituted pyrrolidinyl, optionally substituted morpholinyl, optionally substituted piperidinyl, optionally substituted pyridinyl or optionally substituted phenyl.

Yet other aspects of the invention relate to a pharmaceutical formulation including a pharmaceutically acceptable excipient, and to a method of treatment for heart disease, each entailing a therapeutically effective amount of a compound, isomer, salt or solvate represented by Formula I.

In an additional aspect, the present invention provides methods of screening for compounds that will bind to myosin (particularly myosin II or β myosin), for example compounds that will displace or compete with the binding of the compounds of Formula I. The methods comprise combining an optionally-labeled compound of Formula I, myosin, and at least one candidate agent and determining the binding of the candidate agent to myosin.

In a further aspect, the invention provides methods of screening for modulators of the activity of myosin. The methods comprise combining a compound of Formula I, myosin, and at least one candidate agent and determining the effect of the candidate agent on the activity of myosin.

Other aspects and embodiments will be apparent to those skilled in the art form the following detailed description.

DETAILED DESCRIPTION

The present invention provides compounds useful in selective modulation of the cardiac sarcomere, for example, by potentiating cardiac myosin. The compounds can be used to treat heart failure including CHF, particularly systolic heart failure. The invention further relates to pharmaceutical formulations comprising compounds of the invention, and to methods of treatment employing such compounds or compositions. The compositions are selective modulators of the cardiac sarcomere, for example, potentiating cardiac myosin.

Definitions

As used in the present specification, the following words and phrases are generally intended to have the meanings as set forth below, except to the extent that the context in which they are used indicates otherwise. The following abbreviations and terms have the indicated meanings throughout:

| | |
|---|---|
| Ac = | acetyl |
| Boc = | t-butyloxy carbonyl |
| c- = | cyclo |
| CBZ = | carbobenzoxy = benzyloxycarbonyl |
| DCM = | dichloromethane = methylene chloride = $CH_2Cl_2$ |
| DIEA = | N,N-diisopropylethylamine |
| DMF = | N,N-dimethylformamide |
| DMSO = | dimethyl sulfoxide |
| Et = | ethyl |
| EtOAc = | ethyl acetate |
| EtOH = | ethanol |
| GC = | gas chromatograghy |
| h = | hour |
| Me = | methyl |
| min = | minute |
| mL = | milliliter |
| MTBE = | methyl tert-butyl ether |
| Ph = | phenyl |
| PyBroP = | bromo-tris-pyrrolidinophosphonium hexafluorophosphate |
| rt = | room temperature |
| s- = | secondary |
| t- = | tertiary |
| TFA = | trifluoroacetic acid |
| THF = | tetrahydrofuran |
| TLC = | thin layer chromatography |

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical, synthetically non-feasible and/or inherently unstable.

"Alkyl" is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s-and t-butyl and the like. Preferred alkyl groups are those of $C_{20}$ or below. More preferred alkyl groups are those of $C_{13}$ or below. Still more preferred alkyl groups are those of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene is another subset of alkyl, referring to the same residues as alkyl, but having two points of attachment. Examples of alkylene include ethylene ($-CH_2CH_2-$), propylene ($-CH_2CH_2CH_2-$), dimethylpropylene ($-CH_2C(CH_3)_2CH_2-$) and cyclohexylpropylene ($-CH_2CH_2CH(C_6H_{13})-$). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, preferably including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

The term "substituted alkoxy" refers to the group —O-(substituted alkyl). One preferred substituted alkoxy group is "polyalkoxy" or —O-(optionally substituted alkylene)-(optionally substituted alkoxy), and includes groups such as —OCH$_2$CH$_2$OCH$_3$, and glycol ethers such as polyethyleneglycol and —O(CH$_2$CH$_2$O)$_x$CH$_3$, where x is an integer of about 2-20, preferably about 2-10, and more preferably about 2-5. Another preferred substituted alkoxy group is hydroxyalkoxy or —OCH$_2$(CH$_2$)$_y$OH, where y is an integer of about 1-10, preferably about 1-4.

"Acyl" refers to groups of from 1 to 10 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. "Lower-acyl" refers to groups containing 1 to 4 carbons; "acyloxy" refers to the group O-acyl.

The term "amino" refers to the group —NH$_2$. The term "substituted amino" refers to the group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyl-oxy-sulfonamino.

"Aryl" means a 5- or 6-membered aromatic ring, a bicyclic 9- or 10-membered aromatic ring system, or a tricyclic 12- to 14-membered aromatic ring system. Examples include cyclopenta-1,3-diene, phenyl, naphthyl, indane, tetraline, fluorene, cyclopenta[b]naphthalene and anthracene.

"Aralkoxy" refers to the group —O-aralkyl. Similarly, "heteroaralkoxy" refers to the group —O-heteroaralkyl; "aryloxy" refers to —O-aryl; and "heteroaryloxy" refers to the group —O-heteroaryl.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

"ATPase" refers to an enzyme that hydrolyzes ATP. ATPases include proteins comprising molecular motors such as the myosins.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroaryl" means a 5- or 6-membered aromatic ring containing 1-4 heteroatoms, a bicyclic 8-, 9- or 10-membered aromatic ring system containing 1-4 (or more) heteroatoms, or a tricyclic 11- to 14-membered aromatic ring system containing 1-4 (or more) heteroatoms; the heteroatoms are selected from O, N or S. Examples include furan, pyrrole, thiophene, pyrazole, imidazole, triazole, tetrazole, dithiole, oxazole, isoxazole, oxadiazole, thiazole, thiopyran, pyridine, pyridazine, pyrimidine, pyrazine, indole, benzofuran, benzothiophene, quinoline, isoquinoline and quinoxaline.

"Heterocycle" or "heterocyclyl" refers to a cycloalkyl residue in which one to four of the carbons is replaced by a heteroatom such as oxygen, nitrogen or sulfur. a 4-, 5-, 6- or 7-membered non-aromatic ring containing 1-4 heteroatoms, a bicyclic 8-, 9- or 10-membered non-aromatic ring system containing 1-4 (or more) heteroatoms, or a tricyclic 11- to 14-membered non-aromatic ring system containing 1-4 (or more) heteroatoms; the heteroatoms are selected from O, N or S. Examples include pyrrolidine, tetrahydrofuran, tetrahydro-thiophene, thiazolidine, piperidine, tetrahydro-pyran, tetrahydro-thiopyran, piperazine, morpholine, thiomorpholine and dioxane. Heterocyclyl also includes ring systems including unsaturated bonds, provided the number and placement of unsaturation does not render the group aromatic. Examples include imidazoline, oxazoline, tetrahydroisoquinoline, benzodioxan, benzodioxole and 3,5-dihydrobenzoxazinyl. Examples of substituted heterocyclyl include 4-methyl-1-piperazinyl and 4-benzyl-1-piperidinyl.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. All tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

The term "solvate" refers to a compound (e.g., a compound of Formula I or a pharmaceutically acceptable salt thereof) in physical association with one or more molecules of a pharmaceutically acceptable solvent. It will be understood that phrases such as "a compound of Formula I or a pharmaceutically acceptable salt or solvate thereof" are intended to encompass the compound of Formula I, a pharmaceutically acceptable salt of the compound, a solvate of the compound, and a solvate of a pharmaceutically acceptable salt of the compound.

"Substituted-" alkyl, aryl, heteroaryl and heterocyclyl refer respectively to alkyl, aryl, heteroaryl and heterocyclyl wherein one or more (up to about 5, preferably up to about 3) hydrogen atoms are replaced by a substituent independently selected from the group: acyl, optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted aralkyl (e.g., benzyl), optionally substituted aryloxy (e.g., phenoxy), optionally substituted aralkoxy (e.g., benzyloxy), carboxy (—COOH), carboalkoxy (i.e., acyloxy or —OOCR), alkoxycarbonyl or carboxyalkyl (i.e., esters or —COOR), carboxamido, aminocarbonyl, benzyloxycarbonylamino (CBZ-amino), cyano, carbonyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

The term "sulfanyl" refers to the groups: —S-(optionally substituted alkyl), —S-(optionally substituted aryl), —S-(optionally substituted heteroaryl), and —S-(optionally substituted heterocyclyl).

The term "sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocyclyl).

The term "sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), —S(O$_2$)-(optionally substituted heterocyclyl), —S(O$_2$)-(optionally substituted alkoxy), —S(O$_2$)-optionally substituted aryloxy), —S(O$_2$)-(optionally substituted heteroaryloxy), and —S(O$_2$)-(optionally substituted heterocyclyloxy).

The term "therapeutically effective amount" or "effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease, that is, causing the clinical symptoms of the disease not to develop;

b) inhibiting the disease, that is, slowing or arresting the development of clinical symptoms; and/or c) relieving the disease, that is, causing the regression of clinical symptoms.

Compounds of the Present Invention

The present invention is directed to the compounds that are selective modulators of the cardiac sarcomere (e.g., by stimulating or otherwise potentiating the activity of cardiac myosin), as represented by Formula I:

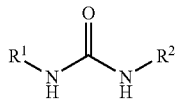

Formula I where:
- $R^1$ is optionally substituted aryl or optionally substituted heteroaryl; and
- $R^2$ is optionally substituted aryl, optionally substituted aralkyl; optionally substituted cycloalkyl, optionally substituted heteroaryl, optionally substituted heteroaralkyl or optionally substituted heterocyclyl, including single stereoisomers, mixtures of stereoisomers, and the pharmaceutically acceptable salts, solvates, and solvates of pharmaceutically acceptable salts thereof. The compounds of Formula I are useful as active agents in practice of the methods of treatment and in manufacture of the pharmaceutical formulations of the invention, and as intermediates in the synthesis of such active agents.

In one of its aspects, the invention relates to one or more compounds of Formula I, where $R^1$ is represented by Formula II:

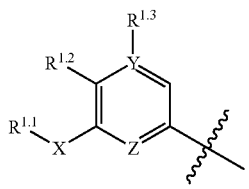

Formula II in which:
- X is —O—, —O-(optionally substituted lower alkylene)-, -(optionally substituted lower alkylene)-O—, —S—, —S-(optionally substituted lower alkylene)-, -(optionally substituted lower alkylene)-S—, —SO$_2$—, —SO$_2$-(optionally substituted lower alkylene)-, or -(optionally substituted lower alkylene)-SO$_2$—;
- Y and Z are independently —C= or —N=, provided that only one of Y or Z is —N=;
- $R^{1.1}$ is optionally substituted aryl, optionally substituted heteroaryl, optionally substituted heterocyclyl, or lower-alkyl substituted with a hydroxy, alkoxy, or aryloxy group or with a substituted amino group;
- $R^{1.2}$ is hydrogen, halo or optionally substituted heteroaryl; and
- $R^{1.3}$ is hydrogen, optionally substituted alkyl, halogen, nitro, cyano, trifluoromethyl, —C≡CH, optionally substituted heteroaryl (especially pyridinyl, or imidazolyl) or alkoxycarbonyl.

Different stereoisomers, for example, about an asymmetric center at the bond between $R^{1.1}$ and X, will vary in potency depending upon the nature of those and the other substituents.

In another aspect, the invention relates to one or more compounds of Formula I where $R^1$ is represented by Formula II, having one or more of the following:
- X is —O—, —O-(optionally substituted lower alkylene)-, -(optionally substituted lower alkylene)-O—, —S—, —S-(optionally substituted lower alkylene)-, -(optionally substituted lower alkylene)-S—, —SO$_2$—, —SO$_2$-(optionally substituted lower alkylene)-, or -(optionally substituted lower alkylene)-SO$_2$—;
- Y and Z are independently —C= or —N=, provided that only one of Y or Z is —N=;
- $R^{1.1}$ is optionally substituted aryl, optionally substituted heteroaryl or optionally substituted heterocyclyl;
- $R^{1.2}$ is hydrogen, halo or optionally substituted heteroaryl; and
- $R^{1.3}$ is hydrogen, halo, optionally substituted heteroaryl or nitro.

Another aspect of the invention relates to one or more compounds of Formula I where $R^1$ is represented by Formula II, having one or more of the following:
- X is —O—;
- Y and Z are —C=;
- $R^{1.1}$ is tetrahydrofuranyl, tetrahydropyranyl, optionally substituted pyrrolidinyl, 3-oxo-tetrahydro-pyrrolo[1,2-c]oxazol-6-yl, optionally substituted morpholinyl, optionally substituted piperidinyl, optionally substituted pyridinyl or optionally substituted phenyl;
- $R^{1.2}$ is hydrogen or fluoro; and
- $R^{1.3}$ is pyridinyl or fluoro.

In yet another aspect, the invention relates to one or more compounds of Formula I where $R^1$ is represented by Formula II and $R^{1.1}$ is 1-acyl-pyrrolidin-3-yl, 1-alkoxycarbonyl-pyrrolidin-3-yl, 1-amidino-pyrrolidin-3-yl, 1-sulfonyl-pyrrolidin-3-yl, 3-oxo-tetrahydro-pyrrolo[1,2-c]oxazol-6-yl, 1-acyl-piperidin-3-yl, 1-alkoxycarbonyl-piperidin-3-yl, 1-amidino-piperidin-3-yl or 1-sulfonyl-piperidin-3-yl, optionally having an additional lower alkoxy or lower alkoxyalkyl ring substituent.

Another aspect of the invention relates to one or more compounds represented by Formula I, where $R^2$ is optionally substituted aryl or optionally substituted heteroaryl, including single stereoisomers, mixtures of stereoisomers, and the pharmaceutically acceptable salts, solvates, and solvates of pharmaceutically acceptable salts thereof, particularly those where $R^2$ is:

optionally substituted phenyl, optionally substituted naphthyl, optionally substituted pyrrolyl, optionally substituted, thiazolyl, optionally substituted isooxazolyl, optionally substituted pyrazolyl, optionally substituted pyridinyl, optionally substituted pyrazinyl, optionally substituted pyrimidinyl or optionally substituted pyridazinyl.

Still another aspect of the invention relates to one or more compounds represented by Formula I where $R^2$ is optionally substituted aralkyl; optionally substituted cycloalkyl, optionally substituted heteroaralkyl or optionally substituted heterocyclyl, including single stereoisomers, mixtures of stereoisomers, and the pharmaceutically acceptable salts, solvates, and solvates of pharmaceutically acceptable salts thereof, particularly those where $R^2$ is:

tetrahydrofuran-2-yl, tetrahydrofuran-3-yl, N-acetyl-pyrrolidin-2-yl, N-acetyl-morpholin-3-yl, N-acyl-piperidin-3-yl, N-acyl-piperidin-4-yl or cyclohexyl, or $R^2$ is represented by the formula —W—$R^{2.1}$ where:
W is $C_1$ to $C_3$ straight or branched-chain optionally substituted alkylene; and R²·¹ is optionally substituted tetrahydrofuranyl, optionally substituted tetrahydropyranyl, optionally substituted pyrrolidinyl, optionally substituted morpholinyl, optionally substituted piperidinyl, optionally substituted pyridinyl or optionally substituted phenyl.

In a further aspect, the invention relates to one or more compounds represented by Formula III:

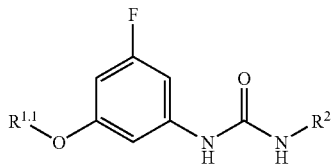

Formula III where:
R¹·¹ is N-substituted piperidin-3-yl or N-substituted pyrrolidin-3-yl, optionally having an additional lower alkoxy or lower alkoxyalkyl ring substituent; and
R² is optionally substituted pyridinyl, including single stereoisomers, mixtures of stereoisomers, and the pharmaceutically acceptable salts, solvates, and solvates of pharmaceutically acceptable salts thereof.

Nomenclature

The compounds of Formula I can be named and numbered (e.g., using AutoNom version 2.1) as described below. For example, the compound of Formula IA:

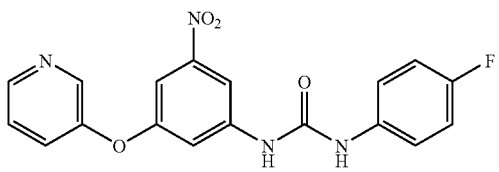

Formula IA i.e., the compound according to Formula I where R¹ is Formula II in which X is —O—, Y and Z are —C=, R¹·¹ is pyridin-3-yl, R¹·² is hydrogen and R¹·³ is nitro, and R² is 4-fluorophenyl, can be named 1-(4-fluoro-phenyl)-3-[3-nitro-5-(pyridin-3-yloxy)-phenyl]-urea.

The compound of Formula IB:

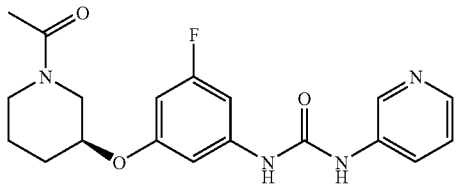

Formula IB i.e., the compound according to Formula I where where R¹ is Formula II in which X is —O—, Y and Z are —C=, R¹·¹ is N-acetyl-piperidin-3-yl, R¹·² is hydrogen and R¹·³ is fluoro, and R² is pyridin-3-yl, can be named (S)-1-[3-(1-acetyl-piperidin-3-yloxy)-5-fluoro-phenyl]-3-pyridin-3-yl-urea.

The compound of Formula IC:

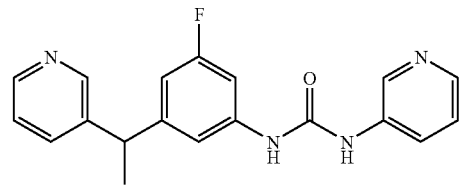

Formula IC i.e., the compound according to Formula I where where R¹ is Formula II in which X is —CH(CH₃)—, Y and Z are —C=, R¹·¹ is pyridin-3-yl, R¹·² is hydrogen and R¹·³ is fluoro, and R² is pyridin-3-yl, can be named 1-[(3-fluoro-5-(1-pyridin-3-yl-ethyl)-phenyl]-3-pyridin-3-yl-urea.

The compound of Formula ID:

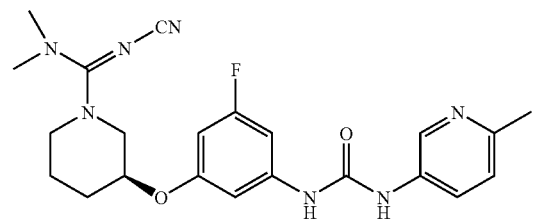

Formula ID i.e., the compound according to Formula I where R¹ is Formula II in which X is —O—, Y and Z are —C=, R¹·¹ is 1-(N²-cyano-N¹,N¹-dimethyamidino)-piperidin-3-yl, R¹·² is hydrogen and R¹·³ is fluoro, and R² is 6-methyl-pyridin-3-yl, can be named (S)-3-[3-fluoro-5-(2-methyl-pyridin-5-yl-ureido)-phenoxy]-piperidine-1-N,N-dimethyl-N-cyano-carboxamidine.

The compound of Formula IE:

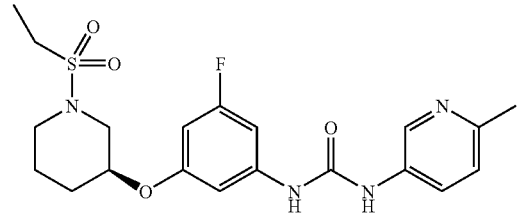

Formula IE i.e., the compound according to Formula I where where R¹ is Formula II in which X is —O—, Y and Z are —C=, R¹·¹ is 1-(ethane-2-sulfonyl)-pyridin-3-yl, R¹·² is hydrogen and R¹·³ is fluoro, and R² is 6-methyl-pyridin-3-yl, can be named (S)-1-{3-[1-(ethane-2-sulfonyl) -piperidin-3-yloxy]-5-fluoro-phenyl}-3-(6-methyl-pydridin-3-yl)-urea.

The compound of Formula IF:

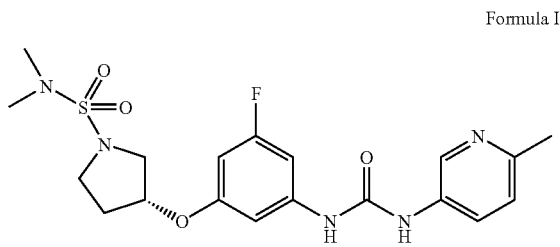

Formula IF i.e., the compound according to Formula I where where $R^1$ is Formula II in which X is —O—, Y and Z are —C═, $R^{1.1}$ is 1-(dimethylaminosulfonyl)-pyrrolidin-3-yl, $R^{1.2}$ is hydrogen and $R^{1.3}$ is fluoro, and $R^2$ is 6-methyl-pyridin-3-yl, can be named (R)-1-[3-(1-dimethyl -aminosulfonyl-piperidin-3-yloxy)-5-fluoro-phenyl]-3-(6-methyl-pydridin-3-yl)-urea.

The compound of Formula IG:

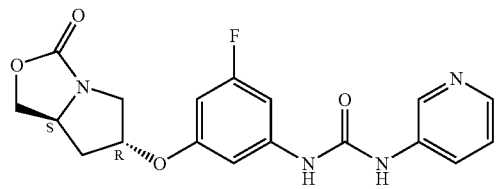

Formula IG i.e., the compound according to Formula I where where $R^1$ is Formula II in which X is —O—, Y and Z are —C═, $R^{1.1}$ is 3-oxo-tetrahydro-pyrrolo[1,2-c]oxazol-6-yl, $R^{1.2}$ is hydrogen and $R^{1.3}$ is fluoro, and $R^2$ is pyridin-3-yl, can be named 1-[3-fluoro-5-(R)-(3-oxo-(S) -tetrahydro-pyrrolo[1,2-c]oxazol-6-yloxy)-phenyl]-3-pyridin-3-yl-urea.

The compound of Formula IH:

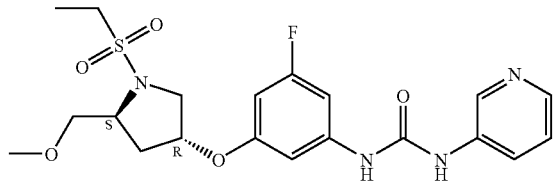

Formula IH i.e., the compound according to Formula I where where $R^1$ is Formula II in which X is —O—, Y and Z are —C═, $R^{1.1}$ is 1-ethanesulfonyl-5-methoxymethyl-pyrrolidin-3-yl, $R^{1.2}$ is hydrogen and $R^{1.3}$ is fluoro, and $R^2$ is pyridin-3-yl, can be named (R)-1-{3-(1-ethanesulfonyl-[(S)$_5$-methoxymethyl]-pyrrolidin-3-yloxy)-5-fluoro-phenyl}-3-pyridin-3-yl-urea, where the (R)— designation is intended to describe the $R^{1.1}$ substituent vis-à-vis the remainder of the molecule through X substituent. Alternatively, as in the example of Formula IG, the compound can be named 1-{3-(R)-(1-ethanesulfonyl-[(S)-5-methoxymethyl]-pyrrolidin-3-yloxy)-5-fluoro-phenyl}-3-pyridin-3-yl-urea.

The compound of Formula II:

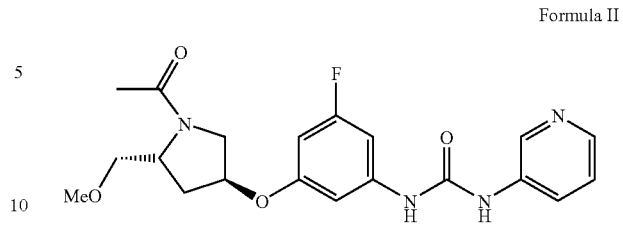

Formula II i.e., the compound according to Formula I where where $R^1$ is Formula II in which X is —O—, Y and Z are —C═, $R^{1.1}$ is 1-acetyl-5-methoxymethyl-pyrrolidin-3-yl, $R^{1.2}$ is hydrogen and $R^{1.3}$ is fluoro, and $R^2$ is pyridin-3-yl, can be named 1-[(S)-3-(1-acetyl-(R)-5-methoxymethyl-pyrrolidin-3-yloxy)-5-fluoro-phenyl]-3-pyridin-3-yl-urea.

The compound of Formula IJ:

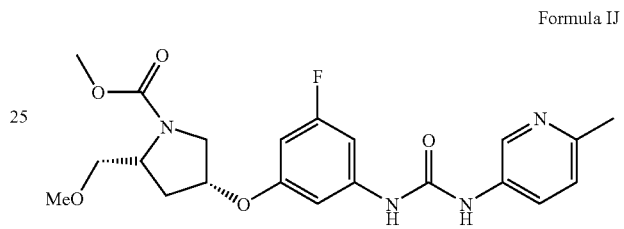

Formula IJ i.e., the compound according to Formula I where where $R^1$ is Formula II in which X is —O—, Y and Z are —C═, $R^{1.1}$ is 1-methoxycarbonyl-2-methoxymethyl-pyrrolidin-4-yl, $R^{1.2}$ is hydrogen and $R^{1.3}$ is fluoro, and $R^2$ is pyridin-3-yl, can be named 4-{3-fluoro-5-[(R)-3-(6-methyl-pyridin-3-yl)-ureido]phenoxy}-(R)-2-methoxymethyl-pyrrolidine-1-carboxylic acid methyl ester.

Synthesis of the Compounds of Formula I

The compounds of the invention can be synthesized utilizing techniques well known in the art, e.g., as illustrated below with reference to the Reaction Schemes.

Synthetic Reaction Parameters

Unless specified to the contrary, the reactions described herein take place at atmospheric pressure, generally within a temperature range from −10° C. to 110° C. Further, except as employed in the Examples or as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent", "organic solvent" or "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

When desired, the (R)— and (S)-isomers may be resolved by methods known to those skilled in the art, for example by formation of diastereoisomeric salts or complexes which may be separated, for example, by crystallization; via formation of diastereoisomeric derivatives which may be separated, for example, by cyrstallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I can be dissolved in a lower alkanol and placed on a Chiralpak AD (205×20 mm) column (Chiral Technologies, Inc.) conditioned for 60 min at 70% EtOAc in Hexane. It will be appreciated that where the desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts or solvents, or by converting one enantiomer to the other by asymmetric transformation.

BRIEF DESCRIPTION OF REACTION SCHEMES

Reaction Scheme 1 illustrates the synthesis of compounds of Formula I.

Reaction Scheme 2 illustrates an alternative synthesis of compounds of Formula I.

Reaction Scheme 3 illustrates the preparation of compounds of Formula 305, which are useful as intermediates in the synthesis of compounds of Formula I.

Reaction Schemes 4 and 5 illustrate the preparation of stereospecific reactants useful in the asymmetric synthesis of single enantiomers of compounds of Formula I.

It will be appreciated by those skilled in the art that one or more of the reactants, steps and/or conditions described in the reaction schemes may require adjustment to accommodate various substituents at $R^1$ and $R^2$.

Materials

Many of the optionally substituted starting compounds 101, 103, 201, 301a and 301b and other reactants are commercially available, e.g., from Aldrich Chemical Company (Milwaukee, Wis.) or can be readily prepared by those skilled in the art using commonly employed synthetic methodology.

REACTION SCHEME 1

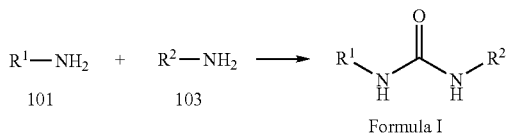

Formula I

Preparation of Compounds of Formula I Referring to Reaction Scheme 1, a flask equipped with a magnetic stirrer, reflux condenser and thermal well, under nitrogen, is charged with phosgene or a phosgene equivalent (typically triphosgene) and a nonpolar, aprotic solvent such as dichloromethane or tetrahydrofuran. A solution of a compound of Formula 101 in a nonpolar, aprotic solvent such as dichloromethane or tetrahydrofuran is added dropwise over about 10-60 minutes and the solution is allowed to stir between 1 to 15 hr. A compound of Formula 103 is added portionwise, and the solution is stirred for about 10-60 min. A base, such as DIEA, is added dropwise for about one hour, and the solution is allowed to stir for about 1-15 hr. The product, a compound of Formula 105, is isolated and purified.

REACTION SCHEME 2

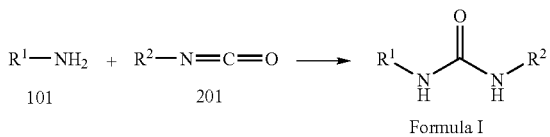

Formula I

Preparation of Compounds of Formula I Reaction Scheme 2 illustrates an alternative synthesis of compounds of Formula I. The isocyanate of Formula 201 can be formed and isolated independently from either corresponding amine (i.e., $R^2$—$NH_2$) using phosgene or a phosgene equivalent or from the corresponding carboxylic acid (i.e., $R^2$—COOH) using a Curtius or Hoffman rearrangement. A mixture of compounds of Formula 101 and 201 in an aprotic solvent such as dichloromethane or tetrahydrofuran from −40° C. to 110° C. is allowed to stir for between 1 to 15 hr. The product, a compound of Formula I, is isolated and purified.

REACTION SCHEME 3

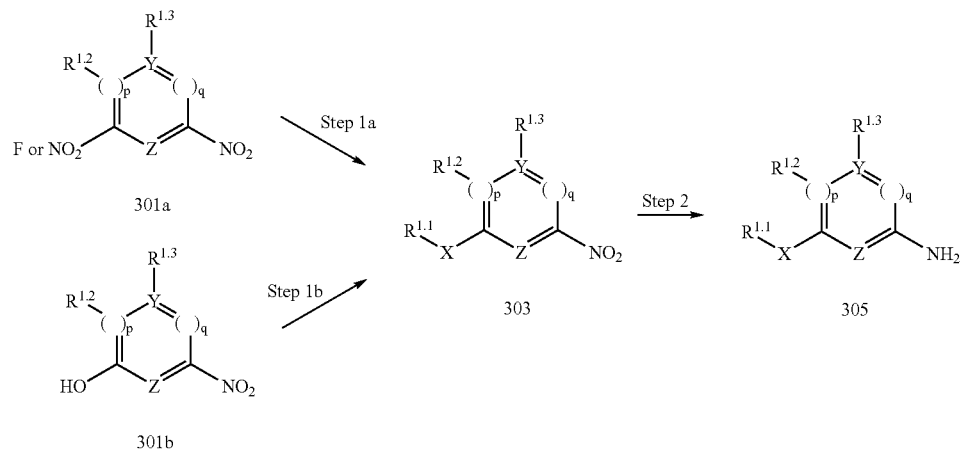

Preparation of Formula 303 Referring to Reaction Scheme 3, Step 1a, a compound of Formula 301a (where p and q are independently whole integers from 0 to 2, and p+q=1 to 4), is combined with about one equivalent of a compound of the formula $R^{1.1}$—OH wherein $R^{1.1}$ is as described above; a base such as potassium carbonate in an aprotic solvent such as DMF. The mixture is heated for about 1-16 hr at about 100° C. The product, a compound of Formula 303, is isolated and purified.

Alternatively, as in Scheme 3, Step 1 b, a compound of Formula 301 b is combined a compound of the formula $R^{1.1}$—OH wherein $R^{3.1}$ is as described above; an azadicarboxylate such as diethyl azadicarboxylate or disopropyl azadicarboxylate and a phosphine such as triphenylphosphine in an aprotic solvent such as THF. The mixture is stirred about 1-16 hr at about room temperature. The product, a compound of Formula 303, is isolated and purified. Alternatively, as in Scheme 3, Step 1b, a compound of Formula 301b is treated with a base such as sodium hydride in an aprotic solvent such as DMF for 1-16 hours from 0° C. to 110° C. A compound of the formula $R^{1.1}$—X wherein $R^{1.1}$ is as described above and X is a leaving group such as a halogen, methanesulfonate, a p-toluenesulfonate, or a triflouromethanesulfonate in an aprotic solvent such as DMF or THF for 1-16 hours from 0° C. to 110° C. The product, a compound of Formula 303, is isolated and purified.

Preparation of Formula 305 Referring to Reaction Scheme 3, Step 2, a Parr hydrogenation bomb is charged with 10% Pd/C under a nitrogen atmosphere, followed by a solution of a compound of Formula 303 in a polar, protic solvent such as ethanol. The reaction is stirred for about 24 hr under about 70 psi $H_2$. The reaction mixture is filtered through celite and concentrated in vacuo to afford a compound of Formula 305, which can be carried forward to Formula I as illustrated with respect to Reaction Schemes 1 and 2.

Preparation of Specific Enantiomers of Formula I As discussed above, a specific enantiomer of Formula I can be synthesized by asymmetric synthesis using optically active reagents, substrates, catalysts or solvents, or by converting one enantiomer to the other by asymmetric transformation. For example, (R)— and (S)-3-hydroxypiperidine are commercially available are commercially available from Sigma-Aldrich, as are (R)— and (S)-hydroxypyrrolidine; they can also be resolved [e.g., using (6,6-dimethyl-2-oxo-adamantan-1-yl)-methane sulfonic acid, see: Ringdahl et. al, *J. Chem. Soc. Perkin Trans. II*, 1981, 4, 697-8] and via other published methodology. Additional asymmetric synthetic approaches can be employed as illustrated in Reaction Schemes 4 and 5, in which PG represents an orthogonal protecting group (or a hydrogen, depending on the stage of synthesis, as will be appreciated by those skilled in the art), LG represents a leaving group, and n is 1, 2 or 3. These protecting and leaving groups can be readily inserted and removed by those skilled in the art using commonly employed synthetic methodology.

REACTION SCHEME 4

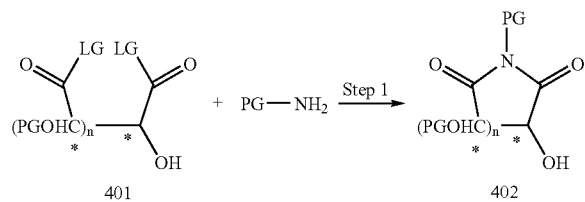

n = 1, 2, or 3

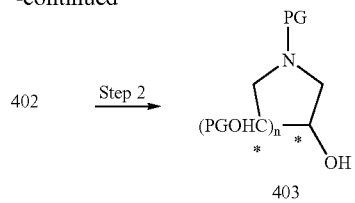

Preparation of Formula 403 Referring to Reaction Scheme 4, Steps 1 and 2, a compound of Formula 401 is combined with about 1 equivalent of a protected amine of Formula 402 (such as benzyl amine) in a solvent such as dichloromethane or DMF. The reaction takes place at −20° C. to 100° C. over a period of 1 to 48 hours. The product, a compound of Formula 403, is isolated conventionally and then treated with a reducing agent (such as lithium aluminum hydride or borane) in an aprotic solvent such as THF. The reaction takes place at −20° C. to 100° C. over a period of 1 to 48 hours. The product, a compound of Formula 403, is then isolated conventionally, and can be carried forward to the compounds of Formula I, e.g., as described above.

REACTION SCHEME 5

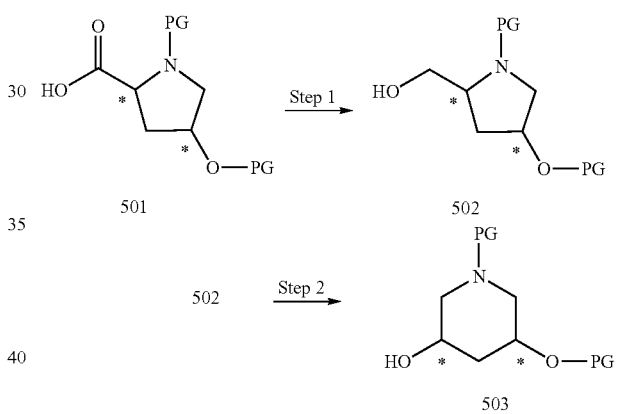

Preparation of Formula 502 Referring to Reaction Scheme 5, Step 1, a compound of Formula 501 is treated with a reducing agent (such as lithium aluminum hydride or lithium borohydride) in solvent such as THF. The reaction takes place at −20° C. to 100° C. over a period of 1 to 48 hours. The product, a compound of Formula 502, is isolated conventionally.

Preparation of Formula 503 Referring to Reaction Scheme 5, Steps 2 and 3, a compound of formula 502 is stirred with an acylating agent, such as triflouroacetic anhydride in a solvent, such as THF from −78° C. to 70° C. for 1 to 12 hours. After addition of a base, such as triethylamine, the mixture is stirred at 20° C. to reflux from 8 to 48 hours. The product, a compound of Formula 503, is isolated conventionally (see, e.g., U.S. Pat. No. 6,316,626) and can be carried forward to the compounds of Formula I, e.g., as described above.

Compounds prepared by the above-described process of the invention can be identified, e.g., by the presence of a detectable amount of Formula 101, 103, 201 or 305. While it is well known that pharmaceuticals must meet pharmacopoeia standards before approval and/or marketing, and that synthetic reagents (such as the various substituted amines or alcohols) and precursors should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a synthetic process of the invention.

Preferred Processes and Last Steps

A racemic mixture of isomers of a compound of Formula I is optionally placed on a chromatography column and separated into (R)— and (S)— enantiomers.

A compound of Formula I is optionally contacted with a pharmaceutically acceptable acid to form the corresponding acid addition salt.

A pharmaceutically acceptable acid addition salt of Formula I is optionally contacted with a base to form the corresponding free base of Formula I.

Preferred Compounds

Preferred embodiments of the invention include or employ the compounds of Formula I having the following combinations and permutations of substituent groups (indented/subgrouped, respectively, in increasing order of preference). These are presented in support of the appended claims to support other combinations and permutations of substituent groups, which for the sake of brevity have not been specifically claimed, but should be appreciated as encompassed within the teachings of the present disclosure. In that regard, the below-described preferred subsets for each substituent (sometimes referenced by paragraph number) are intended to apply to that substituent alone or in combination with one, several, or all of the described subsets for the other substituents.

In one embodiment, $R^1$ is optionally substituted phenyl, naphthyl or pyridinyl wherein the aromatic ring is optionally substituted with one, two, or three of the following groups optionally substituted lower alkyl (preferably, methyl, hydroxymethyl, or hydroxyethyl); lower alkoxy (especially methoxy); halogen (preferably, chloro or fluoro); hydroxy; cyano; or substituted amino (especially carbamoyl).

In a preferred embodiment, $R^1$ is represented by Formula II in which:

X is —O—, —O-(optionally substituted lower alkylene)-, or -(optionally substituted lower alkylene)-O—.

X is —O—.

Y and Z are —C=.

$R^{1.1}$ is optionally substituted aryl, optionally substituted heteroaryl or optionally substituted heterocyclyl; preferably optionally substituted azepanyl, optionally substituted azetidinyl, optionally substituted 3-oxo-tetrahydro-pyrrolo-[1,2-c]-oxazolyl, optionally substituted tetrahydrofuranyl, optionally substituted tetrahydropyranyl, optionally substituted pyrrolidinyl, optionally substituted morpholinyl, optionally substituted piperidinyl, optionally substituted pyridinyl or optionally substituted phenyl.

$R^{1.1}$ is tetrahydrofuranyl, tetrahydropyranyl, optionally substituted pyrrolidinyl, 3-oxo-tetrahydro-pyrrolo[1,2-c]oxazolyl, optionally substituted morpholinyl, optionally substituted piperidinyl, optionally substituted pyridinyl or optionally substituted phenyl.

$R^{1.1}$ is optionally substituted heteroaryl or optionally substituted heterocyclyl.

$R^{1.1}$ is tetrahydrofuranyl, tetrahydropyranyl, substituted-pyrrolidinyl, 3-oxo-tetrahydro-pyrrolo[1,2-c]oxazolyl, substituted-piperidinyl, pyridinyl or hydroxy-lower alkyl-phenyl.

$R^{1.1}$ is 1-acyl-pyrrolidin-3-yl, 1-alkoxycarbonyl-pyrrolidin-3-yl, 1-amidino-pyrrolidin-3-yl, 1-sulfonyl-pyrrolidin-3-yl, 3-oxo-tetrahydro-pyrrolo[1,2-c]oxazol-6-yl, 1-acyl-piperidin-3-yl, 1-alkoxycarbonyl-piperidin-3-yl, 1-amidino-piperidin-3-yl or 1-sulfonyl-piperidin-3-yl, optionally having an additional lower alkoxy or lower alkoxyalkyl ring substituent.

$R^{1.1}$ is 1-acetyl-piperidin-3-yl, 1-methoxyacetyl-piperidin-3-yl, 1-(azetidine-1-carbonyl)-piperidin-3-yl, 1-methoxycarbonyl-piperidin-3-yl, 1-ethoxycarbonyl-piperidin-3-yl, 1-dimethylaminocarbonyl-piperidin-3-yl, 1-methanesulfonyl-piperidin-3-yl, 1-(ethane-2-sulfonyl)-piperidin-3-yl, 1-(propane-2-sulfonyl)-piperidin-3-yl, 1-(azetidin-1-yl-sulfonyl)-piperidin-3-yl, 1-dimethylaminosulfonyl-piperidin-3-yl, 1-($N^1$-azetidin-1-yl-$N^2$-cyano-amidino)-piperidin-3-yl, 1-($N^2$-cyano-$N^1$,$N^1$-dimethyamidino)-piperidine-3-yl, 1-acetyl-pyrrolidin-3-yl, 1-acetyl-5-methoxymethyl-pyrrolidin-3-yl, 1-methoxyacetyl-pyrrolidin-3-yl, 1-(azetidine-1-carbonyl)-pyrrolidin-3-yl, 1-methoxycarbonyl-pyrrolidin-3-yl, 1-methoxycarbonyl-2-methoxymethyl-pyrrolidin-4-yl, 1-methanesulfonyl-pyrrolidin-3-yl, 1-(ethane-2-sulfonyl)-pyrrolidin-3-yl, 1-(ethane-2-sulfonyl)-4-methoxy-pyrrolidin-3-yl, 1-(ethane-2-sulfonyl)-5-methoxymethyl-pyrrolidin-3-yl, 1-(propane-2-sulfonyl)-pyrrolidin-3-yl, 1-(azetidin-1-yl-sulfonyl)-pyrrolidin-3-yl, 1-dimethylaminosulfonyl-pyrrolidin-3-yl, 1-dimethylaminosulfonyl-2-methoxymethyl-pyrrolidin-4-yl, 1-($N^1$-azetidin-1-yl-$N^2$-cyano-amidino)-pyrrolidin-3-yl, 1-($N^2$-cyano-$N^1$,$N^1$-dimethyamidino)-pyrrolidin-3-yl, or 3-oxo-tetrahydro-pyrrolo[1,2-c]oxazol-6-yl.

$R^{1.1}$ is 1-acyl-pyrrolidin-3-yl, 1-sulfonyl-pyrrolidin-3-yl, 3-oxo-tetrahydro-pyrrolo[1,2-c]oxazol-6-yl, 1-alkoxycarbonyl-piperidin-3-yl or 1-sulfonyl-piperidin-3-yl.

$R^{1.1}$ is 1-methoxycarbonyl-2-methoxymethyl-pyrrolidin-4-yl, 1-acetyl-5-methoxymethyl-pyrrolidin-3-yl, 1-(ethane-2-sulfonyl)-pyrrolidin-3-yl, 1-(ethane-2-sulfonyl)-5-methoxymethyl-pyrrolidin-3-yl, 1-dimethylaminosulfonyl-pyrrolidin-3-yl, 1-dimethylaminosulfonyl-2-methoxymethyl-pyrrolidin-4-yl, 3-oxo-tetrahydro-pyrrolo[1,2-c]oxazol-6-yl, 1-methoxycarbonyl-piperidin-3-yl, 1-methanesulfonyl-piperidin-3-yl, or 1-(ethane-2-sulfonyl)-piperidin-3-yl.

$R^{1.2}$ is hydrogen or fluoro.

$R^{1.2}$ is hydrogen.

$R^{1.3}$ is optionally substituted heteroaryl (especially pyridinyl or imidazolyl), nitro or halo.

$R^{1.3}$ is pyridinyl or fluoro.

$R^{1.3}$ is fluoro.

$R^1$ is represented by Formula II in which $R^{1.1}$ is:

optionally substituted aryl (especially phenyl or phenyl substituted with an acyl, alkoxy, optionally substituted alkyl, or halo group);

optionally substituted heteroaryl (especially pyridinyl or pyridinyl substituted with an acyl, alkoxy, optionally substituted alkyl, or halo group);

optionally substituted heteroaralkyl (especially pyridinylmethyl-, pyridinylethyl-, or pyridinylpropyl);

optionally substituted heterocyclyl (especially optionally substituted piperidinyl, tetrahydrofuranyl-, oxo-piperidinyl-, or morpholinyl-); or lower-alkyl substituted with a hydroxy, alkoxy, or aryloxy group or with a substituted amino group. Particularly preferred amino substituents are —$SO_2R'$, —(CO)R', or —(CO)N(R')$_2$ wherein R' is hydrogen or optionally substituted lower alkyl.

In another preferred embodiment where $R^1$ is represented by Formula II, $R^{1.1}$ is selected from the group: 2-substituted-azetidin-1-yl, N-substituted pyrrolidin-3-yl, N-substituted piperidin-3 or 4-yl and N-substituted-azepan-3 or 4-yl, in which:

The 2-substituted-azetidine substituent or N-substituent is acetyl, methoxyacetyl, azetidin-1-yl, acetyl, ethane-2-carbonyl, propane-2-carbonyl, methoxycarbonyl, (eth-2-oxy)-carbonyl, (prop-2-oxy)-carbonyl, dimethylaminocarbonyl, $N^2$-cyano-$N^1$,$N^1$-dimethyamidino or $N^1$-azetidin-1-yl-$N^2$-cyano-amidino.

Each having zero, one or two additional ring substituents selected from: methoxy and methoxymethyl.

$R^2$ is optionally substituted aryl or optionally substituted heteroaryl.

$R^2$ is optionally substituted pyridinyl, pyrimidinyl, or pyridazinyl.

The $R^2$ aryl or heteroaryl ring is substituted with one, two, or three of the following groups: optionally substituted lower alkyl, halo, hydroxy, cyano, substituted amino, nitro, methylenedioxy, ethelenedioxy, optionally substituted heterocyclyl, sulfanyl, sulfonyl, —OR', —COR', —(CO)OR' and/or —(CO)N R'R' where each R' is independently hydrogen or optionally substituted lower alkyl (R' especially being methyl in the cases of —OR' and —COR').

Optionally substituted lower alkyl being preferably, methyl, hydroxymethyl, methoxymethyl, trifluoromethyl, ethyl, (amino)carbonylmethyl, (methylamino)carbonylmethyl, acetylaminomethyl, or hydroxyethyl.

Optionally substituted heterocyclyl especially being optionally substituted mopholinyl.

Sulfanyl especially being methylsulfanyl.

$R^2$ is optionally substituted phenyl, optionally substituted naphthyl, optionally substituted pyrrolyl, optionally substituted, thiazolyl, optionally substituted isooxazolyl, optionally substituted pyrazolyl, optionally substituted pyridinyl, optionally substituted pyrazinyl, optionally substituted pyrimidinyl, or optionally substituted pyridazinyl.

$R^2$ has one or two optional substituents selected from: acetyl, lower alkyl, lower alkoxy, lower alkoxyalkyl, lower alkoxy carbonyl, hydroxy lower alkyl, alkoxy lower alkyl, carboxy, halo, trifluoromethyl.

$R^2$ is isooxazol-3-yl, 5-methyl-isooxazol-3-yl, isooxazol-5-yl, pyrazol-3-yl, pyrazinyl, substituted phenyl or optionally substuted pyridinyl.

$R^2$ is phenyl having one or two substituents selected from: lower alkyl, lower alkoxy, halo, hydroxy and hydroxy lower alkyl.

$R^2$ is pyridin-2-yl, pyridin-3-yl or pyridin-4-yl optionally having a substituent selected from: acetyl, lower alkyl, lower alkoxy, lower alkoxyalkyl, lower alkoxy carbonyl, carboxy and trifluoromethyl.

$R^2$ is optionally-p-substituted pyridin-3-yl $R^2$ is pyridin-3-yl optionally p-substituted with a member of the group: acetyl, methyl, ethyl, methoxy, methoxymethyl, hydroxy, hydroxymethyl and hydroxyethyl.

$R^2$ is pyridin-3-yl or 6-methyl-pyridin-3-yl.

$R^2$ is optionally substituted aralkyl, optionally substituted cycloalkyl, optionally substituted heteroaralkylyl or optionally substituted heterocyclyl.

$R^2$ is tetrahydrofuran-2-yl, tetrahydrofuran-3-yl, N-acetyl-pyrrolidin-2-yl, N-acetyl-morpholin-3-yl, N-acyl-piperidin-3-yl, N-acyl-piperidin-4-yl or cyclohexyl.

$R^2$ is represented by the formula —W—$R^{2.1}$ where:

W is $C_1$ to $C_3$ straight or branched-chain alkylene.

W is methylene.

$R^{2.1}$ is tetrahydrofuranyl, tetrahydropyranyl, optionally substituted pyrrolidinyl, optionally substituted morpholinyl, optionally substituted piperidinyl, optionally substituted pyridinyl or optionally substituted phenyl.

$R^{2.1}$ is tetrahydrofuran-2-yl, tetrahydrofuran-3-yl, N-acetyl-pyrrolidin-2-yl, N-acetyl-morpholin-3-yl, N-acyl-piperidin-3-yl, N-acyl-piperidin-4-yl, pyridin-3-yl, pyridin-4-yl, optionally substituted piperidinyl p-methoxy-phenyl or p-fluoro-phenyl.

In another embodiment, when $R^1$ and/or $R^2$ is optionally substituted heteroaryl, the other of $R^1$ and/or $R^2$ is independently selected from the group consisting of optionally substituted 2-oxo-2,3-dihydro-1H-imidazole-4-yl; oxazole-4-yl; 2H-pyrazole-3-yl; 1H-imidazole-4-yl; oxazole-2-yl; thiazol-2-yl; thiazol-4-yl; thiazol-5-yl; 1H-imidazole-2-yl; 2H-[1,2,4]triazole-3-yl; 5-oxo-4,5-dihydro-1H-[1,2,4]triazole-3-yl; 5-oxo-4,5-dihydro-[1,3,4]oxadiazole-2-yl; pyridine-3-yl; pyridine-2-yl; pyrimidine-2-yl; pyridazine-3-yl; 6-oxo-1,6-dihydro-pyridine-2-yl; 2-oxo-2,3-dihydro-pyrimidine-4-yl; 2-oxo-1,2-dihydro-pyridine-3-yl; isoxazole-3-yl; and 1H-pyrazole-3-yl.

In another preferred embodiment, $R^1$ is an optionally substituted 5- or 6-membered heterocycle. Particularly preferred heterocycles include optionally substituted 2-oxo-2,3-dihydro-1H-imidazole-4-yl; oxazole-4-yl; 2H-pyrazole-3-yl; 1H-imidazole-4-yl; oxazole-2-yl; thiazol-2-yl; thiazol-4-yl; thiazol-5-yl; 1H-imidazole-2-yl; 2H-[1,2,4]triazole-3-yl; 5-oxo-4,5-dihydro-1H-[1,2,4]triazole-3-yl; 5-oxo-4,5-dihydro-[1,3,4]oxadiazole-2-yl; pyridine-3-yl; pyridine-2-yl; pyrimidine-2-yl; pyridazine-3-yl; 6-oxo-1,6-dihydro-pyridine-2-yl; 2-oxo-2,3-dihydro-pyrimidine-4-yl; 2-oxo-1,2-dihydro-pyridine-3-yl; isoxazole-3-yl; and 1H-pyrazole-3-yl.

In another particular embodiment, $R^2$ is an optionally substituted cycloalkyl or heterocyclic ring.

More particularly, $R^2$ is indan-1-yl; indan-2-yl; 1,2,3,4-tetrahydro-naphthalen-1-yl; 1,2,3,4-tetrahydro-naphthalen-2-yl; 6,7,8,9-tetrahydro-5H-benzocyclohepten-6-yl; piperidinyl; oxo-piperidinyl; pyrrolidinyl; oxo-pyrrolidinyl; tetrahydro-furanyl or morpholinyl, each being optionally substituted with one or more of the following: acetyl, acyl, acyloxy, optionally substituted alkoxy (especially methoxy), alkoxycarbonyl, optionally substituted lower-alkyl, optionally substituted amino, aminocarbonyl, azido, cyano, optionally substituted heteroaryl, optionally substituted heteroaralkyl, optionally substituted heteroaralkoxy, optionally substituted heteroaryloxy, optionally substituted heterocyclyl, optionally substituted heterocycloalkyl, halo, hydroxy, nitro, sulfanyl, sulfonamido, sulfonyl and trifluoromethyl.

In a particular embodiment of the foregoing, $R^1$ is optionally substituted phenyl, pyridinyl, indazolyl, quinolinyl, benzoimidazolyl, oxazolyl, isoxazolyl, or oxadiazolyl.

More particularly, $R^1$ is phenyl or pyridinyl, each of which optionally is substituted with one or more of the following: amino, substituted amino, halogen, alkoxy, optionally substituted aryloxy (especially phenoxy), optionally substituted heteroaryloxy (especially methyl-pyridinyloxy- or methoxy-pyridinyloxy-), optionally substituted lower-alkyl (especially, methyl), or hydroxy.

Illustrative of the suitable combinations and permutations of particular substituents are the compounds, pharmaceutically acceptable salts and solvates where $R^1$ is represented by Formula II in which X is —O—, Y and Z are —C═, $R^{1.2}$ is hydrogen, $R^{1.3}$ is fluoro, and one or more of $R^{1.1}$ and $R^2$ is/are as described in paragraphs 0095-00103 above, such as:

$R^{1.1}$ is tetrahydrofuranyl, tetrahydropyranyl, substituted-pyrrolidinyl, 3-oxo-tetrahydro-pyrrolo[1,2-c]oxazolyl, substituted-piperidinyl, pyridinyl or hydroxy-lower alkyl-phenyl.

$R^{1.1}$ is 1-acyl-pyrrolidin-3-yl, 1-alkoxycarbonyl-pyrrolidin-3-yl, 1-amidino-pyrrolidin-3-yl, 1-sulfonyl-pyrrolidin-3-yl, 3-oxo-tetrahydro-pyrrolo[1,2-c]oxazol-6-yl, 1-acyl-piperidin-3-yl, 1-alkoxycarbonyl-piperidin-3-yl, 1-amidino-piperidin-3-yl or 1-sulfonyl-piperidin-3-yl, optionally having an additional lower alkoxy or lower alkoxyalkyl ring substituent.

$R^{1.1}$ is 1-acetyl-piperidin-3-yl, 1-methoxyacetyl-piperidin-3-yl, 1-(azetidine-1-carbonyl)-piperidin-3-yl, 1-methoxycarbonyl-piperidin-3-yl, 1-ethoxycarbonyl-piperidin-3-yl, 1-dimethylaminocarbonyl-piperidin-3-yl, 1-methanesulfonyl-piperidin-3-yl, 1-(ethane-2-sulfonyl)-piperidin-3-yl, 1-(propane-2-sulfonyl)-piperidin-3-yl, 1-(azetidin-1-yl-sulfonyl)-piperidin-3-yl, 1-dimethylaminosulfonyl-piperidin-3-yl, 1-($N^1$-azetidin-1-yl-$N^2$-cyano-amidino)-piperidin-3-yl, 1-($N^2$-cyano-$N^1$,$N^1$-dimethyamidino)-piperidine-3-yl, 1-acetyl-pyrrolidin-3-yl, 1-acetyl-5-methoxymethyl-pyrrolidin-3-yl, 1-methoxyacetyl-pyrrolidin-3-yl, 1-(azetidine-1-carbonyl)-pyrrolidin-3-yl, 1-methoxycarbonyl-pyrrolidin-3-yl, 1-methoxycarbonyl-2-methoxymethyl-pyrrolidin-4-yl, 1-methanesulfonyl-pyrrolidin-3-yl, 1-(ethane-2-sulfonyl)-pyrrolidin-3-yl, 1-(ethane-2-sulfonyl)-4-methoxy-pyrrolidin-3-yl, 1-(ethane-2-sulfonyl)-5-methoxymethyl-pyrrolidin-3-yl, 1-(propane-2-sulfonyl)-pyrrolidin-3-yl, 1-(azetidin-1-yl-sulfonyl)-pyrrolidin-3-yl, 1-dimethylaminosulfonyl-pyrrolidin-3-yl, 1-dimethylaminosulfonyl-2-methoxymethyl-pyrrolidin-4-yl, 1-($N^1$-azetidin-1-yl-$N^2$-cyano-amidino)-pyrrolidin-3-yl, 1-($N^2$-cyano-$N^1$,$N^1$-dimethyamidino)-pyrrolidin-3-yl, or 3-oxo-tetrahydro-pyrrolo[1,2-c]oxazol-6-yl.

$R^{1.1}$ is 1-acyl-pyrrolidin-3-yl, 1-sulfonyl-pyrrolidin-3-yl, 3-oxo-tetrahydro-pyrrolo[1,2-c]oxazol-6-yl, 1-alkoxycarbonyl-piperidin-3-yl or 1-sulfonyl-piperidin-3-yl.

$R^{1.1}$ is 1-methoxycarbonyl-2-methoxymethyl-pyrrolidin-4-yl, 1-acetyl-5-methoxymethyl-pyrrolidin-3-yl, 1-(ethane-2-sulfonyl)-pyrrolidin-3-yl, 1-(ethane-2-sulfonyl)-5-methoxymethyl-pyrrolidin-3-yl, 1-dimethylaminosulfonyl-pyrrolidin-3-yl, 1-dimethylaminosulfonyl-2-methoxymethyl-pyrrolidin-4-yl, 3-oxo-tetrahydro-pyrrolo[1,2-c]oxazol-6-yl, 1-methoxycarbonyl-piperidin-3-yl, 1-methanesulfonyl-piperidin-3-yl, or 1-(ethane-2-sulfonyl)-piperidin-3-yl.

$R^2$ is pyridin-3-yl or 6-methyl-pyridin-3-yl.

$R^2$ is pyridin-3-yl or 6-methyl-pyridin-3-yl.

$R^2$ is pyridin-3-yl optionally p-substituted with a member of the group: acetyl, methyl, ethyl, methoxy, methoxymethyl, hydroxy, hydroxymethyl and hydroxyethyl.

$R^2$ is optionally-p-substituted pyridin-3-yl $R^2$ is phenyl having one or two substituents selected from: lower alkyl, lower alkoxy, halo, hydroxy and hydroxy lower alkyl.

$R^2$ is pyridin-2-yl, pyridin-3-yl or pyridin-4-yl optionally having a substituent selected from: acetyl, lower alkyl, lower alkoxy, lower alkoxyalkyl, lower alkoxy carbonyl, carboxy and trifluoromethyl.

$R^2$ is optionally substituted phenyl or optionally substituted pyridinyl.

$R^2$ is phenyl having one or two substituents selected from: lower alkyl, lower alkoxy, halo, hydroxy and hydroxy lower alkyl.

$R^2$ is pyridin-2-yl, pyridin-3-yl or pyridin-4-yl optionally having a substituent selected from: acetyl, lower alkyl, lower alkoxy, lower alkoxyalkyl, lower alkoxy carbonyl, carboxy and trifluoromethyl.

$R^2$ is optionally-p-substituted pyridin-3-yl.

$R^2$ is pyridin-3-yl optionally p-substituted with a member of the group: acetyl, methyl, ethyl, methoxy, methoxymethyl, hydroxy, hydroxymethyl and hydroxyethyl.

$R^2$ is pyridin-3-yl or 6-methyl-pyridin-3-yl.

Thus, the compounds where $R^1$ is represented by Formula II in which X is —O—, Y and Z are —C═, $R^{1.2}$ is hydrogen, $R^{1.3}$ is fluoro, including those where the above-described groupings and sub-groups of substituents are taken individually and/or combined together as illustrated with regard to those compounds where $R^{1.1}$ is tetrahydrofuranyl, tetrahydropyranyl, substituted-pyrrolidinyl, substituted-piperidinyl, pyridinyl or hydroxy-lower alkyl-phenyl, are particularly preferred for practice of the present invention, as are the compounds of Formula III.

In another embodiment, where $R^1$ is represented by Formula II in which X is —O—, Y and Z are —C═, $R^{1.1}$ is N-substituted-piperidin-3-yl, $R^{1.2}$ is hydrogen, $R^{1.3}$ is fluoro, and $R^2$ is pyridin-3-yl, modulation of myocyte contractility, aortic ring dilation and protein binding properties has been observed by varying the substituent on $R^{1.1}$, for example as between N-acyl, methyl carbamate, dimethyl urea, morpholinyl urea, piperidinyl urea, piperazinyl urea, N,N-dimethylcyanoguanidine, and sulfamide analogues, as well as certain N-substituted pyrrolidin-2-yl homologs (such modulation also being influenced by stereochemistry and the nature of the other substituent groups).

The following group of compounds are preferred (individually and collectively) as compounds of the present invention, and in connection with their formulations, methods of manufacture and use:

1-[3-(1-Acetyl-piperidin-3-yloxy)-5-fluoro-phenyl]-3-pyridin-3-yl-urea;

1-[3-(1-Acetyl-piperidin-3-yloxy)-5-fluoro-phenyl]-3-pyrimidin-5-yl-urea;

1-[3-(1-Acetyl-piperidin-3-yloxy)-5-fluoro-phenyl]-3-(2-methyl-pyrimidin-5-yl)-urea;
1-[3-(1-Acetyl-piperidin-3-yloxy)-5-fluoro-phenyl]-3-(2-methoxy-pyrimidin-5-yl)-urea;
1-[3-(1-Acetyl-piperidin-3-yloxy)-5-fluoro-phenyl]-3-pyrazin-2-yl-urea;
1-[3-(1-Acetyl-piperidin-3-yloxy)-5-fluoro-phenyl]-3-(5-methoxy-pyrazin-2-yl)-urea;
1-[3-(1-Acetyl-piperidin-3-yloxy)-5-fluoro-phenyl]-3-(6-methoxy-pyridazin-3-yl)-urea;
1-[3-(1-Acetyl-piperidin-3-yloxy)-5-fluoro-phenyl]-3-(6-trifluoromethyl-pyridin-3-yl)-urea;
3-[3-Fluoro-5-(3-pyridin-3-yl-ureido)-phenoxy]-piperidine-1-carboxylic acid methyl ester;
3-{3-Fluoro-5-[3-(6-methoxy-pyridin-3-yl)-ureido]-phenoxy}-piperidine-1-carboxylic acid methyl ester;
3-{(3-Fluoro-5-[3-(6-methyl-pyridin-3-yl)-ureido]-phenoxy}-piperidine-1-carboxylic acid methyl ester;
3-{3-Fluoro-5-[3-(6-methoxy-pyridin-3-yl)-ureido]-phenoxy}-piperidine-1-carboxylic acid dimethylamide;
3-{3-[3-(6-Cyano-pyridin-3-yl)-ureido]-5-fluoro-phenoxy}-piperidine-1-carboxylic acid methyl ester;
1-[3-(1-Acetyl-piperidin-3-yloxy)-5-fluoro-phenyl]-3-(6-cyano-pyridin-3-yl)-urea;
1-[3-(1-Acetyl-piperidin-3-yloxy)-5-fluoro-phenyl]-3-(6-methylsulfanyl-pyridin-3-yl) -urea;
1-[3-(1-Acetyl-piperidin-3-yloxy)-5-fluoro-phenyl]-3-(6-acetyl-pyridin-3-yl)-urea;
1-[3-(1-Acetyl-piperidin-3-yloxy)-5-fluoro-phenyl]-3-[6-(1-hydroxy-ethyl)-pyridin-3-yl]-urea;
3-[3-Fluoro-5-(3-pyridin-3-yl-ureido)-phenoxy]-piperidine-1-carboxylic acid dimethylamide;
1-[3-Fluoro-5-(1-methanesulfonyl-piperidin-3-yloxy)-phenyl]-3-pyridin-3-yl-urea;
1-[3-Fluoro-5-(1-methanesulfonyl-piperidin-3-yloxy)-phenyl]-3-(6-methoxy-pyridin-3-yl)-urea;
1-[3-Fluoro-5-(6-oxo-piperidin-3-yloxy)-phenyl]-3-pyridin-3-yl-urea;
1-(6-Cyano-pyridin-3-yl)-3-[3-fluoro-5-(1-methanesulfonyl-piperidin-3-yloxy)-phenyl]-urea;
3-{3-[3-(6-Cyano-pyridin-3-yl)-ureido]-5-fluoro-phenoxy}piperidine-carboxylic acid dimethylamide;
1-[3-(1-Acetyl-piperidin-3-yloxy)-5-fluoro-phenyl]-3-(6-methyl-pyridin-3-yl)-urea;
3-{3-Fluoro-5-[3-(6-methyl-pyridin-3-yl)-ureido]-phenoxy}-piperidine-carboxylic acid methyl ester;
3-{3-[3-(6-Carbamoyl-pyridin-3-yl)-ureido]-5-fluoro-phenoxy}-piperidine-1-carboxylic acid methyl ester;
1-[3-Fluoro-5-(2-oxo-piperidin-3-yloxy)-phenyl]-3-(6-methyl-pyridin-3-yl)-urea;
1-[3-Fluoro-5-(6-oxo-piperidin-3-yloxy)-phenyl]-3-(6-methyl-pyridin-3-yl)-urea;
3-{3-Fluoro-5-[3-(6-methoxymethyl-pyridin-3-yl)-ureido]-phenoxy}-piperidine-1-carboxylic acid methyl ester;
3-(3-{3-[6-(Acetylamino-methyl)-pyridin-3-yl]-ureido}-5-fluoro-phenoxy)-piperidine-1-carboxylic acid methyl ester;
5-{3-[3-(1-Dimethylcarbamoyl-piperidin-3-yloxy)-5-fluoro-phenyl]-ureido}-pyridine-2-carboxylic acid amide;
3-(3-{3-[6-(Acetylamino-methyl)-pyridin-3-yl]-ureido}-5-fluoro-phenoxy)-piperidine-1-carboxylic acid dimethylamide;
3-{3-Fluoro-5-[3-(6-methoxymethyl-pyridin-3-yl)-ureido]-phenoxy}-piperidine-1-carboxylic acid dimethylamide;
3-{3-Fluoro-5-[3-(6-methyl-pyridin-3-yl)-ureido]-phenoxy}-piperidine-1-carboxylic acid dimethylamide;
1-[3-Fluoro-5-(1-methanesulfonyl-piperidin-3-yloxy)-phenyl]-3-(6-methyl-pyridin-3-yl) -urea;
1-[3-Fluoro-5-(1-methanesulfonyl-piperidin-3-yloxy)-phenyl]-3-(6-methoxymethyl-pyridin-3-yl)-urea;
1-{3-Fluoro-5-[1-(morpholine-4-carbonyl)-piperidin-3-yloxy]-phenyl}-3-(6-methyl -pyridin-3-yl)-urea;
1-{3-Fluoro-5-[1-(4-hydroxy-piperidine-1-carbonyl)-piperidin-3-yloxy]-phenyl}-3-(6-methyl-pyridin-3-yl)-urea;
1-(3-{3-Fluoro-5-[3-(6-methylpyridin-3-yl)-ureido]-phenoxy}-piperidine-1-carbonyl)-piperidine-4-carboxylic acid ethyl ester;
5-{3-[3-Fluoro-5-(1-methanesulfonyl-piperidin-3-yloxy)-phenyl]-ureido}-pyridine-2-carboxylic acid amide;
5-{3-[3-(1-Acetyl-piperidin-3-yloxy)-5-fluoro-phenyl]-ureido}-pyridine-2-carboxylic acid amide;
1-[3-(1-Acetyl-piperidin-3-yloxy)-5-fluoro-phenyl]-3-(6-ethyl-pyridin-3-yl)-urea;
2-(5-{3-[3-(1-Acetyl-piperidin-3-yloxy)-5-fluoro-phenyl]-ureido}-pyridin-2-yl) -N-methyl-acetamide;
1-[3-(1-Acetyl-piperidin-3-yloxy)-5-fluoro-phenyl]-3-(6-methoxymethyl-pyridin-3-yl) -urea;
2-(5-{3-[3-(1-Acetyl-piperidin-3-yloxy)-5-fluoro-phenyl]-ureido}-pyridin-2-yl) -acetamide;
1-[3-(1-Acetyl-piperidin-3-yloxy)-5-fluoro-phenyl]-3-pyridazin-4-yl-urea;
1-[3-(1-Acetyl-piperidin-3-yloxy)-4,5-difluoro-phenyl]-3-(6-methyl-pyridin-3-yl)-urea;
1-[3-Fluoro-5-(pyridin-3-yloxy)-phenyl]-3-pyridin-3-yl-urea;
N'-Cyano-3-{3-fluoro-5-[3-(6-methyl-pyridin-3-yl)-ureido]-phenoxy}-N,N-dimethyl -piperidine-1-carboxamidine;
N'-Cyano-3-{3-fluoro-5-[3-(pyridin-3-yl)-ureido]-phenoxy}-N,N-dimethyl-piperidine-1-carboxamidine;
1-[3-(1-Acetyl-piperidin-3-yloxy)-5-fluoro-phenyl]-3-(2-methyl-pyrimidin-5-yl)-urea;
1-[3-(1-Acetyl-piperidin-3-yloxy)-5-fluoro-phenyl]-3-(2-methoxy-pyrimidin-5-yl)-urea;
1-[3-(1-Acetyl-piperidin-3-yloxy)-5-fluoro-phenyl]-3-(5-methoxy-pyrazin-2-yl)-urea;
1-[3-(1-Acetyl-piperidin-3-yloxy)-5-fluoro-phenyl]-3-pyrazin-2-yl-urea;
1-[3-(1-Acetyl-piperidin-3-yloxy)-5-fluoro-phenyl]-3-pyridazin-4-yl-urea;
1-[3-(1-Acetyl-piperidin-3-yloxy)-5-fluoro-phenyl]-3-(6-methoxy-pyridazin-3-yl)-urea;
1-[3-(1-Acetyl-piperidin-3-yloxy)-5-fluoro-phenyl]-3-(6-methyl-pyridazin-3-yl)-urea;
1-[3-(1-Acetyl-piperidin-3-yloxy)-5-fluoro-phenyl]-3-(pyridazin-3-yl)-urea;
1-[3-Fluoro-5-(2-methyl-1,1-dioxo-hexahydro-1$\lambda^6$-thia-2,6a-diaza-pentalen-5-yloxy)phenyl]-3-pyridin-3-yl-urea;
3-[3-Fluoro-5-(3-pyridin-3-yl-ureido)-phenoxy]-pyrrolidine-1-sulfonic acid dimethylamide;
3-{3-Fluoro-5-[3-(6-methyl-pyridin-3-yl)-ureido]-phenoxy}-pyrrolidine-1-sulfonic acid dimethylamide;
3-{3-Fluoro-5-[3-(6-methyl-pyridin-3-yl)-ureido]-phenoxy}-pyrrolidine-sulfonic acid dimethylamide;
1-[3-(1-Acetyl-5-methoxymethyl-pyrrolidin-3-yloxy)-5-fluorophenyl]-3-pyridin-3-yl-urea;
1-[3-(1-Acetyl-5-methoxymethyl-pyrrolidin-3-yloxy)-5-fluorophenyl]-3-(6-methyl-pyridin -3-yl)-urea;
4-{3-fluoro-5-[3-(6-methyl-pyridin-3-yl)-ureido]phenoxy}-2-methoxymethyl-pyrrolidine-1-carboxylic acid methyl ester
1-[3-(1-Acetyl-piperidin-3-yloxy)-5-fluoro-phenyl]-3-pyrimidin-5-yl-urea; and 1-[3-(1-Acetyl-piperidin-3-yloxy)-5-fluoro-phenyl]-3-(6-methoxy-pyridin-3-yl)-urea, or a single stereoisomer, mixture of stereoisomers, pharmaceutically acceptable salt, solvate, or a solvate of a pharmaceutically acceptable salt thereof.

The following group of compounds are further preferred (individually and collectively) as compounds of the present invention, and in connection with their formulations, methods of manufacture and use:

1-[3-(1-Acetyl-piperidin-3-yloxy)-5-fluoro-phenyl]-3-(6-methoxy-pyridin-3-yl)-urea;
1-[3-(1-Acetyl-piperidin-3-yloxy)-5-fluoro-phenyl]-3-pyridin-3-yl-urea;
1-[3-Fluoro-5-(1-methanesulfonyl-piperidin-3-yloxy)-phenyl]-3-pyridin-3-yl-urea;
1-[3-Fluoro-5-(3-pyridin-3-yl-ureido)-phenoxy]-piperidine-1-carboxylic acid methyl ester;
(R)-1-[3-(1-Acetyl-piperidin-3-yloxy)-5-fluoro-phenyl]-3-(6-methoxy-pyridin-3-yl)-urea;
(S)-1-[3-(1-Acetyl-piperidin-3-yloxy)-5-fluoro-phenyl]-3-(6-methoxy-pyridin-3-yl)-urea;
(R)-1-[3-(1-Acetyl-piperidin-3-yloxy)-5-fluoro-phenyl]-3-pyridin-3-yl-urea;
(S)-1-[3-(1-Acetyl-piperidin-3-yloxy)-5-fluoro-phenyl]-3-pyridin-3-yl-urea;
(R)-1-[3-Fluoro-5-(3-pyridin-3-yl-ureido)-phenoxy]-piperidine-1-carboxylic acid methyl ester;
(S)-1-[3-Fluoro-5-(3-pyridin-3-yl-ureido)-phenoxy]-piperidine-1-carboxylic acid methyl ester;
(R)-3-{3-Fluoro-5-[3-(6-methyl-pyridin-3-yl)-ureido]-phenoxy}-piperidine-1-carboxylic acid methyl ester;
(S)-3-{3-Fluoro-5-[3-(6-methyl-pyridin-3-yl)-ureido]-phenoxy}-piperidine-1-carboxylic acid methyl ester;
(R)-1-[3-Fluoro-5-(3-pyridin-3-yl-ureido)-phenoxy]-piperidine-1-carboxylic acid dimethylamide;
(S)-1-[3-Fluoro-5-(3-pyridin-3-yl-ureido)-phenoxy]-piperidine-1-carboxylic acid dimethylamide;
(R)-1-[3-Fluoro-5-(1-methanesulfonyl-piperidin-3-yloxy)-phenyl]-3-pyridin-3-yl-urea;
(S)-1-[3-Fluoro-5-(1-methanesulfonyl-piperidin-3-yloxy)-phenyl]-3-pyridin-3-yl-urea;
(R)-1-[3-(1-Acetyl-piperidin-3-yloxy)-5-fluoro-phenyl]-3-(6-methyl-pyridin-3-yl)-urea;
(S)-1-[3-(1-Acetyl-piperidin-3-yloxy)-5-fluoro-phenyl]-3-(6-methyl-pyridin-3-yl)-urea;
(R)-1-{3-Fluoro-5-[3-(6-methyl-pyridin-3-yl)-ureido]-phenoxy}-piperidine-1-carboxylic acid methyl ester;
(S)-1-{3-Fluoro-5-[3-(6-methyl-pyridin-3-yl)-ureido]-phenoxy}-piperidine-1-carboxylic acid methyl ester;
(R)-1-{3-Fluoro-5-[3-(6-methyl-pyridin-3-yl)-ureido]-phenoxy}-piperidine-1-carboxylic acid dimethylamide;
(S)-1-{3-Fluoro-5-[3-(6-methyl-pyridin-3-yl)-ureido]-phenoxy}-piperidine-1-carboxylic acid dimethylamide;
(R)-1-[3-Fluoro-5-(1-methanesulfonyl-piperidin-3-yloxy)-phenyl]-3-(6-methyl-pyridin-3-yl)-urea;
(S)-1-[3-Fluoro-5-(1-methanesulfonyl-piperidin-3-yloxy)-phenyl]-3-(6-methyl-pyridin-3-yl)-urea;
(R)-1-[3-Fluoro-5-(3-pyridin-3-yl-ureido)-phenoxy]-piperidine-1-carboxylic acid ethyl ester;
(S)-1-[3-Fluoro-5-(3-pyridin-3-yl-ureido)-phenoxy]-piperidine-1-carboxylic acid ethyl ester;
(R)-1-[3-Fluoro-5-(3-pyridin-3-yl-ureido)-phenoxy]-piperidine-1-sulfonic acid dimethylamide;
(S)-1-[3-Fluoro-5-(3-pyridin-3-yl-ureido)-phenoxy]-piperidine-1-sulfonic acid dimethylamide;
(R)-1-{3-Fluoro-5-[3-(6-methyl-pyridin-3-y)-ureido]-phenoxy}-piperidine-1-sulfonic acid dimethylamide;
(S)-1-{3-Fluoro-5-[3-(6-methyl-pyridin-3-yl)-ureido]-phenoxy}-piperidine-1-sulfonic acid dimethylamide;
(R)-1-{3-Fluoro-5-[1-(propane-2-sulfonyl)-piperidin-3-yloxy]-phenyl}-3-pyridin-3-yl-urea;
(S)-1-{3-Fluoro-5-[1-(propane-2-sulfonyl)-piperidin-3-yloxy]-phenyl}-3-pyridin-3-yl-urea;
(R)-1-{3-Fluoro-5-[1-(propane-2-sulfonyl)-piperidin-3-yloxy]-phenyl}-3-(6-methyl -pyridin-3-yl)-urea;
(S)-1-{3-Fluoro-5-[1-(propane-2-sulfonyl)-piperidin-3-yloxy]-phenyl}-3-(6-methyl -pyridin-3-yl)-urea;
(R)-1-[3-(1-ethanesulfonyl-piperidin-3-yloxy)-5-fluoro-phenyl]-3-pyridin-3-yl-urea;
(S)-1-[3-(1-ethanesulfonyl-piperidin-3-yloxy)-5-fluoro-phenyl]-3-pyridin-3-yl-urea;
(R)-1-[3-(1-Ethanesulfonyl-piperidin-3-yloxy)-5-fluoro-phenyl]-3-(6-methyl-pyridin-3-yl)-urea;
(S)-1-[3-(1-Ethanesulfonyl-piperidin-3-yloxy)-5-fluoro-phenyl]-3-(6-methyl-pyridin-3-yl)-urea;
(R)-3-[3-Fluoro-5-(pyridin-3-yl-ureido)-phenoxy]-piperidine-1-N,N-dimethyl-N-cyano-carboxamidine;
(S)-3-[3-Fluoro-5-(pyridin-3-yl-ureido)-phenoxy]-piperidine-1-N,N-dimethyl-N-cyano-carboxamidine;
(R)-3-[3-Fluoro-5-(2-methyl-pyridin-5-yl-ureido)-phenoxy]-piperidine-1-N,N-dimethyl-N-cyano -carboxamidine;
(S)-3-[3-Fluoro-5-(2-methyl-pyridin-5-yl-ureido)-phenoxy]-piperidine-1-N,N-dimethyl-N-cyano -carboxamidine;
(R)-1-[3-(1-Ethanesulfonyl-piperidin-3-yloxy)-5-fluoro-phenyl]-3-(6-methyl-pydridin-3-yl)-urea;
(S)-1-[3-(1-Ethanesulfonyl-piperidin-3-yloxy)-5-fluoro-phenyl]-3-(6-methyl-pydridin-3-yl)-urea;
(R)-1-{3-Fluoro-5-[3-(6-methyl-pyridin-3-y)-ureido]-phenoxy}-piperidine-1-carboxylic acid ethyl ester;
(S)-1-{3-Fluoro-5-[3-(6-methyl-pyridin-3-yl)-ureido]-phenoxy}-piperidine-1-carboxylic acid ethyl ester;
(R)-1-[3-Fluoro-5-(2-methyl-1,1-dioxo-hexahydro-1$\lambda^6$-thia-2,6a-diaza-pentalen-5-yloxy)phenyl]-3-pyridin-3-yl-urea;
(S)-1-[3-Fluoro-5-(2-methyl-1,1-dioxo-hexahydro-1$\lambda^6$-thia-2,6a-diaza-pentalen-5-yloxy)phenyl]-3-pyridin-3-yl-urea;
(R)-3-[3-Fluoro-5-(3-pyridin-3-yl-ureido)-phenoxy]-pyrrolidine-1-sulfonic acid dimethylamide;
(S)-3-[3-Fluoro-5-(3-pyridin-3-yl-ureido)-phenoxy]-pyrrolidine-1-sulfonic acid dimethylamide;
(R)-3-{3-Fluoro-5-[3-(6-methyl-pyridin-3-yl)-ureido]-phenoxy}-pyrrolidine-1-sulfonic acid dimethylamide;
(S)-3-{3-Fluoro-5-[3-(6-methyl-pyridin-3-yl)-ureido]-phenoxy}-pyrrolidine-1-sulfonic acid dimethylamide;
1-[(R)-3-(1-Acetyl-(R)-5-methoxymethyl-pyrrolidin-3-yloxy)-5-fluoro-phenyl]-3-pyridin-3-yl-urea;
1-[(S)-3-(1-Acetyl-(S)-5-methoxymethyl-pyrrolidin-3-yloxy)-5-fluoro-phenyl]-3-pyridin-3-yl-urea;
1-[(R)-3-(1-Acetyl-(S)-5-methoxymethyl-pyrrolidin-3-yloxy)-5-fluoro-phenyl]-3-pyridin-3-yl-urea;
1-[(S)-3-(1-Acetyl-(R)-5-methoxymethyl-pyrrolidin-3-yloxy)-5-fluoro-phenyl]-3-pyridin-3-yl-urea;
4-{3-fluoro-5-[(R)-3-(6-methyl-pyridin-3-yl)-ureido]phenoxy}-(R)-2-methoxymethyl -pyrrolidine-1-carboxylic acid methyl ester;
4-{3-fluoro-5-[(S)-3-(6-methyl-pyridin-3-yl)-ureido]phenoxy}-(S)-2-methoxymethyl -pyrrolidine-1-carboxylic acid methyl ester;

4-{3-fluoro-5-[(R)-3-(6-methyl-pyridin-3-yl)-ureido]phenoxy}-(S)-2-methoxymethyl -pyrrolidine-1-carboxylic acid methyl ester;

4-{3-fluoro-5-[(S)-3-(6-methyl-pyridin-3-yl)-ureido]phenoxy}-(R)-2-methoxymethyl -pyrrolidine-1-carboxylic acid methyl ester;

1-[(R)-3-(1-Acetyl-(R)-5-methoxymethyl-pyrrolidin-3-yloxy)-5-fluoro-phenyl]-3-(6-methyl-pyridin-3-yl)-urea;

1-[(S)-3-(1-Acetyl-(S)-5-methoxymethyl-pyrrolidin-3-yloxy)-5-fluoro-phenyl]-3-(6-methyl-pyridin-3-yl)-urea;

1-[(R)-3-(1-Acetyl-(S)-5-methoxymethyl-pyrrolidin-3-yloxy)-5-fluoro-phenyl]-3-(6-methyl-pyridin-3-yl)-urea; and 1-[(S)-3-(1-Acetyl-(R)-5-methoxymethyl-pyrrolidin-3-yloxy)-5-fluoro-phenyl]-3-(6-methyl-pyridin-3-yl)-urea, or a single stereoisomer, mixture of stereoisomers, pharmaceutically acceptable salt, solvate, or a solvate of a pharmaceutically acceptable salt thereof.

The following group of compounds are similarly preferred (individually and collectively) as compounds of the present invention, and in connection with their formulations, methods of manufacture and use:

1-[3-(1-Acetyl-piperidin-3-yloxy)-5-fluoro-phenyl]-3-(6-methoxy-pyridin-3-yl)-urea;

1-[3-(1-Acetyl-piperidin-3-yloxy)-5-fluoro-phenyl]-3-pyridin-3-yl-urea;

1-[3-Fluoro-5-(1-methanesulfonyl-piperidin-3-yloxy)-phenyl]-3-pyridin-3-yl-urea;

1-[3-Fluoro-5-(3-pyridin-3-yl-ureido)-phenoxy]-piperidine-1-carboxylic acid methyl ester;

(R)-1-[3-(1-Acetyl-piperidin-3-yloxy)-5-fluoro-phenyl]-3-(6-methoxy-pyridin-3-yl)-urea;

(R)-1-[3-(1-Acetyl-piperidin-3-yloxy)-5-fluoro-phenyl]-3-pyridin-3-yl-urea;

(R)-1-[3-Fluoro-5-(3-pyridin-3-yl-ureido)-phenoxy]-piperidine-1-carboxylic acid methyl ester;

(R)-1-[3-Fluoro-5-(3-pyridin-3-yl-ureido)-phenoxy]-piperidine-1-carboxylic acid dimethylamide;

(R)-1-[3-Fluoro-5-(1-methanesulfonyl-piperidin-3-yloxy)-phenyl]-3-pyridin-3-yl-urea;

(R)-1-[3-(1-Acetyl-piperidin-3-yloxy)-5-fluoro-phenyl]-3-(6-methyl-pyridin-3-yl)-urea;

(R)-1-{3-Fluoro-5-[3-(6-methyl-pyridin-3-yl)-ureido]-phenoxy}-piperidine-1-carboxylic acid methyl ester;

(R)-1-{3-Fluoro-5-[3-(6-methyl-pyridin-3-yl)-ureido]-phenoxy}-piperidine-1-carboxylic acid dimethylamide;

(R)-1-[3-Fluoro-5-(1-methanesulfonyl-piperidin-3-yloxy)-phenyl]-3-(6-methyl-pyridin-3-yl)-urea;

(R)-1-[3-Fluoro-5-(3-pyridin-3-yl-ureido)-phenoxy]-piperidine-1-carboxylic acid ethyl ester;

(R)-1-[3-Fluoro-5-(3-pyridin-3-yl-ureido)-phenoxy]-piperidine-1-sulfonic acid dimethylamide;

(R)-1-{3-Fluoro-5-[3-(6-methyl-pyridin-3-yl)-ureido]-phenoxy}-piperidine-1-sulfonic acid dimethylamide;

(R)-1-{3-Fluoro-5-[1-(propane-2-sulfonyl)-piperidin-3-yloxy]-phenyl}-3-pyridin-3-yl-urea;

(R)-1-{3-Fluoro-5-[1-(propane-2-sulfonyl)-piperidin-3-yloxy]-phenyl}-3-(6-methyl -pyridin-3-yl)-urea;

(R)-1-[3-(1-ethanesulfonyl-piperidin-3-yloxy)-5-fluorophenyl]-3-pyridin-3-yl-urea;

(R)-1-[3-(1-Ethanesulfonyl-piperidin-3-yloxy)-5-fluorophenyl]-3-(6-methyl-pyridin-3-yl)-urea;

(S)-3-[3-Fluoro-5-(pyridin-3-yl-ureido)-phenoxy]-piperidine-1-N,N-dimethyl-N-cyano-carboxamidine;

(S)-3-[3-Fluoro-5-(2-methyl-pyridin-5-yl-ureido)-phenoxy]-piperidine-1-N,N-dimethyl-N-cyano -carboxamidine;

(S)-1-[3-Fluoro-5-(3-pyridin-3-yl-ureido)-phenoxy]-piperidine-1-sulfonic acid dimethylamide;

(S)-1-{3-Fluoro-5-[3-(6-methyl-pyridin-3-yl)-ureido]-phenoxy}-piperidine-1-sulfonic acid dimethylamide;

(S)-1-[3-(1-Ethanesulfonyl-piperidin-3-yloxy)-5-fluorophenyl]-3-pyridin-3-yl-urea;

(S)-1-{3-Fluoro-5-[1-(propane-2-sulfonyl)-piperidin-3-yloxy]-phenyl}-3-pyridin-3-yl-urea;

(S)-1-[3-Fluoro-5-(3-pyridin-3-yl-ureido)-phenoxy]-piperidine-1-carboxylic acid methyl ester;

(S)-1-[3-Fluoro-5-(3-pyridin-3-yl-ureido)-phenoxy]-piperidine-1-carboxylic acid ethyl ester;

(S)-1-[3-(1-Ethanesulfonyl-piperidin-3-yloxy)-5-fluorophenyl]-3-(6-methyl-pydridin-3-yl)-urea;

(S)-1-{3-Fluoro-5-[1-(propane-2-sulfonyl)-piperidin-3-yloxy]-phenyl}-3-(6-methyl -pyridin-3-yl)-urea;

(S)-1-{3-Fluoro-5-[3-(6-methyl-pyridin-3-yl)-ureido]-phenoxy}-piperidine-1-carboxylic acid methyl ester;

(S)-1-{3-Fluoro-5-[3-(6-methyl-pyridin-3-y)-ureido]-phenoxy}-piperidine-1-carboxylic acid ethyl ester;

(R)-1-[3-Fluoro-5-(2-methyl-1,1-dioxo-hexahydro-1$\lambda^6$-thia-2,6a-diaza-pentalen-5-yloxy)phenyl]-3-pyridin-3-yl-urea;

(R)-3-[3-Fluoro-5-(3-pyridin-3-yl-ureido)-phenoxy]-pyrrolidine-1-sulfonic acid dimethylamide;

(R)-3-{3-Fluoro-5-[3-(6-methyl-pyridin-3-yl)-ureido]-phenoxy}-pyrrolidine-1-sulfonic acid dimethylamide;

(S)-3-{3-Fluoro-5-[3-(6-methyl-pyridin-3-yl)-ureido]-phenoxy}-pyrrolidin e-1-sulfonic acid dimethylamide;

1-[(R)-3-(1-Acetyl-(R)-5-methoxymethyl-pyrrolidin-3-yloxy)-5-fluoro-phenyl]-3-pyridin-3-yl-urea;

4-{3-fluoro-5-[(R)-3-(6-methyl-pyridin-3-yl)-ureido]phenoxy}-(R)-2-methoxymethyl -pyrrolidine-1-carboxylic acid methyl ester;

1-[(R)-3-(1-Acetyl-(R)-5-methoxymethyl-pyrrolidin-3-yloxy)-5-fluorophenyl]-3-(6-methyl-pyridin-3-yl)-urea; and (S)-1-[3-Fluoro-5-(1-methanesulfonyl-piperidin-3-yloxy)-phenyl]-3-pyridin-3-yl-urea, or a single stereoisomer, mixture of stereoisomers, pharmaceutically acceptable salt, solvate, or a solvate of a pharmaceutically acceptable salt thereof.

The following group of compounds are also further preferred (individually and collectively) as compounds of the present invention, and in connection with their formulations, methods of manufacture and use:

(S)-3-{3-Fluoro-5-[3-(6-methyl-pyridin-3-yl)-ureido]-phenoxy}-pyrrolidine-1-sulfonic acid dimethylamide;

(R)-3-{3-Fluoro-5-[3-(6-methyl-pyridin-3-yl)-ureido]-phenoxy}-pyrrolidine-1-sulfonic acid dimethylamide;

(S)-3-[3-Fluoro-5-(2-methyl-pyridin-5-yl-ureido)-phenoxy]-pyrrolidine-1-N,N-dimethyl-N-cyano -carboxamidine;

(R)-3-[3-Fluoro-5-(2-methyl-pyridin-5-yl-ureido)-phenoxy]-pyrrolidine-1-N,N-dimethyl-N-cyano -carboxamidine;

(S)-3-[3-Fluoro-5-(3-pyridin-3-yl-ureido)-phenoxy]-pyrrolidine-1-sulfonic acid dimethylamide;

(R)-3-[3-Fluoro-5-(3-pyridin-3-yl-ureido)-phenoxy]-pyrrolidine-1-sulfonic acid dimethylamide;

(S)-3-[3-Fluoro-5-(pyridin-2-yl-ureido)-phenoxy]-pyrrolidine-1-N,N-dimethyl-N-cyano-carboxamidine;

(R)-3-[3-Fluoro-5-(pyridin-2-yl-ureido)-phenoxy]-pyrrolidine-1-N,N-dimethyl-N-cyano-carboxamidine;
(S)-3-[3-Fluoro-5-(3-pyridin-3-yl-ureido)-phenoxy]-pyrrolidine-1-carboxylic acid methyl ester;
(R)-3-[3-Fluoro-5-(3-pyridin-3-yl-ureido)-phenoxy]-pyrrolidine-1-carboxylic acid methyl ester;
(S)-3-{3-Fluoro-5-[3-(6-methyl-pyridin-3-yl)-ureido]-phenoxy}-pyrrolidine-1-carboxylic acid methyl ester;
(R)-3-{3-Fluoro-5-[3-(6-methyl-pyridin-3-yl)-ureido]-phenoxy}-pyrrolidine-1-carboxylic acid methyl ester;
(S)-1-{3-Fluoro-5-[1-(propane-2-sulfonyl)-pyrrolidin-3-yloxy]-phenyl}-3-pyridin-3-yl-urea;
(R)-1-{3-Fluoro-5-[1-(propane-2-sulfonyl)-pyrrolidin-3-yloxy]-phenyl}-3-pyridin-3-yl-urea;
(S)-1-{3-Fluoro-5-[1-(propane-2-sulfonyl)-pyrrolidin-3-yloxy]-phenyl}-3-(6-methyl-pyridin-3-yl)-urea;
(R)-1-{3-Fluoro-5-[1-(propane-2-sulfonyl)-pyrrolidin-3-yloxy]-phenyl}-3-(6-methyl-pyridin-3-yl)-urea;
(S)-1-{3-Fluoro-5-[1-(ethane-2-sulfonyl)-pyrrolidin-3-yloxy]-phenyl}-3-pyridin-3-yl-urea;
(R)-1-{3-Fluoro-5-[1-(ethane-2-sulfonyl)-pyrrolidin-3-yloxy]-phenyl}-3-pyridin-3-yl-urea;
(S)-1-{3-Fluoro-5-[1-(ethane-2-sulfonyl)-pyrrolidin-3-yloxy]-phenyl}-3-(6-methyl-pyridin-3-yl)-urea;
(R)-1-{3-Fluoro-5-[1-(ethane-2-sulfonyl)-pyrrolidin-3-yloxy]-phenyl}-3-(6-methyl-pyridin-3-yl)-urea;
(S)-1-{3-Fluoro-5-[1-(methane-2-sulfonyl)-pyrrolidin-3-yloxy]-phenyl}-3-(6-methyl-pyridin-3-yl)-urea;
(R)-1-{3-Fluoro-5-[1-(methane-2-sulfonyl)-pyrrolidin-3-yloxy]-phenyl}-3-(6-methyl-pyridin-3-yl)-urea;
(S)-4-{3-Fluoro-5-[3-(6-methyl-pyridin-3-yl)-ureido]-phenoxy}-[(S)-2-methoxymethyl]-pyrrolidine-1-sulfonic acid dimethylamide;
(R)-4-{3-Fluoro-5-[3-(6-methyl-pyridin-3-yl)-ureido]-phenoxy}-[(R)-2-methoxymethyl]-pyrrolidine-1-sulfonic acid dimethylamide;
(S)-4-{3-Fluoro-5-[3-(6-methyl-pyridin-3-yl)-ureido]-phenoxy}-[(R)-2-methoxymethyl]-pyrrolidine-1-sulfonic acid dimethylamide;
(R)-4-{3-Fluoro-5-[3-(6-methyl-pyridin-3-yl)-ureido]-phenoxy}-[(S)-2-methoxymethyl]-pyrrolidine-1-sulfonic acid dimethylamide;
(S)-4-{3-Fluoro-5-[3-(6-methyl-pyridin-3-yl)-ureido]-phenoxy}-[(S)-2-methoxymethyl]-pyrrolidine-1-carboxylic acid methyl ester;
(R)-4-{3-Fluoro-5-[3-(6-methyl-pyridin-3-yl)-ureido]-phenoxy}-[(R)-2-methoxymethyl]-pyrrolidine-1-carboxylic acid methyl ester;
(S)-4-{3-Fluoro-5-[3-(6-methyl-pyridin-3-yl)-ureido]-phenoxy}-[(R)-2-methoxymethyl]-pyrrolidine-1-carboxylic acid methyl ester;
(R)-4-{3-Fluoro-5-[3-(6-methyl-pyridin-3-yl)-ureido]-phenoxy}-[(S)-2-methoxymethyl]-pyrrolidine-1-carboxylic acid methyl ester;
(S)-1-{3-(1-Ethanesulfonyl-[(S)-4-methoxy]-pyrrolidin-3-yloxy)-5-fluoro-phenyl}-3-(6-methyl-pyridin-3-yl)-urea;
(R)-1-{3-(1-Ethanesulfonyl-[(R)-4-methoxy]-pyrrolidin-3-yloxy)-5-fluoro-phenyl}-3-(6-methyl-pyridin-3-yl)-urea;
(S)-1-{3-(1-Ethanesulfonyl-[(R)-4-methoxy]-pyrrolidin-3-yloxy)-5-fluoro-phenyl}-3-(6-methyl-pyridin-3-yl)-urea;
(R)-1-{3-(1-Ethanesulfonyl-[(S)-4-methoxy]-pyrrolidin-3-yloxy)-5-fluoro-phenyl}-3-(6-methyl-pyridin-3-yl)-urea;
(S)-1-{3-(1-Ethanesulfonyl-[(S)-5-methoxymethyl]-pyrrolidin-3-yloxy)-5-fluoro-phenyl}-3-pyridin-3-yl-urea;
(R)-1-{3-(1-Ethanesulfonyl-[(R)-5-methoxymethyl]-pyrrolidin-3-yloxy)-5-fluoro-phenyl}-3-pyridin-3-yl-urea;
(S)-1-{3-(1-Ethanesulfonyl-[(R)-5-methoxymethyl]-pyrrolidin-3-yloxy)-5-fluoro-phenyl}-3-pyridin-3-yl-urea;
(R)-1-{3-(1-Ethanesulfonyl-[(S)-5-methoxymethyl]-pyrrolidin-3-yloxy)-5-fluoro-phenyl}-3-pyridin-3-yl-urea;
(S)-1-{3-(1-Ethanesulfonyl-[(S)-5-methoxymethyl]-pyrrolidin-3-yloxy)-5-fluoro-phenyl}-3-(6-methyl-pyridin-3-yl)-urea;
(R)-1-{3-(1-Ethanesulfonyl-[(R)-5-methoxymethyl]-pyrrolidin-3-yloxy)-5-fluoro-phenyl}-3-(6-methyl-pyridin-3-yl)-urea;
(S)-1-{3-(1-Ethanesulfonyl-[(R)-5-methoxymethyl]-pyrrolidin-3-yloxy)-5-fluoro-phenyl}-3-(6-methyl-pyridin-3-yl)-urea;
(R)-1-{3-(1-Ethanesulfonyl-[(S)-5-methoxymethyl]-pyrrolidin-3-yloxy)-5-fluoro-phenyl}-3-(6-methyl-pyridin-3-yl)-urea;
1-[3-Fluoro-5-(S)-(3-oxo-(S)-tetrahydro-pyrrolo[1,2-c]oxazol-6-yloxy)-phenyl]-3-pyridin-3-yl-urea;
1-[3-Fluoro-5-(R)-(3-oxo-(R)-tetrahydro-pyrrolo[1,2-c]oxazol-6-yloxy)-phenyl]-3-pyridin-3-yl-urea;
1-[3-Fluoro-5-(S)-(3-oxo-(R)-tetrahydro-pyrrolo[1,2-c]oxazol-6-yloxy)-phenyl]-3-pyridin-3-yl-urea;
1-[3-Fluoro-5-(R)-(3-oxo-(S)-tetrahydro-pyrrolo[1,2-c]oxazol-6-yloxy)-phenyl]-3-pyridin-3-yl-urea;
1-[3-Fluoro-5-(S)-(3-oxo-(S)-tetrahydro-pyrrolo[1,2-c]oxazol-6-yloxy)-phenyl]-3-(6-methyl-pyridin-3-yl)-urea;
1-[3-Fluoro-5-(R)-(3-oxo-(R)-tetrahydro-pyrrolo[1,2-c]oxazol-6-yloxy)-phenyl]-3-(6-methyl-pyridin-3-yl)-urea;
1-[3-Fluoro-5-(S)-(3-oxo-(R)-tetrahydro-pyrrolo[1,2-c]oxazol-6-yloxy)-phenyl]-3-(6-methyl-pyridin-3-yl)-urea; and
1-[3-Fluoro-5-(R)-(3-oxo-(S)-tetrahydro-pyrrolo[1,2-c]oxazol-6-yloxy)-phenyl]-3-(6-methyl-pyridin-3-yl)-urea, or a single stereoisomer, mixture of stereoisomers, pharmaceutically acceptable salt, solvate, or a solvate of a pharmaceutically acceptable salt thereof.

The following group of compounds are similarly preferred (individually and collectively) as compounds of the present invention, and in connection with their formulations, methods of manufacture and use:

(S)-3-{3-Fluoro-5-[3-(6-methyl-pyridin-3-yl)-ureido]-phenoxy}-pyrrolidine-1-sulfonic acid dimethylamide;
(R)-3-{3-Fluoro-5-[3-(6-methyl-pyridin-3-yl)-ureido]-phenoxy}-pyrrolidine-1-sulfonic acid dimethylamide;
(S)-3-[3-Fluoro-5-(2-methyl-pyridin-5-yl-ureido)-phenoxy]-pyrrolidine-1-N,N-dimethyl-N-cyano -carboxamidine;
(R)-3-[3-Fluoro-5-(2-methyl-pyridin-5-yl-ureido)-phenoxy]-pyrrolidine-1-N,N-dimethyl-N-cyano -carboxamidine;
(S)-3-[3-Fluoro-5-(3-pyridin-3-yl-ureido)-phenoxy]-pyrrolidine-1-sulfonic acid dimethylamide;
(S)-3-[3-Fluoro-5-(pyridin-2-yl-ureido)-phenoxy]-pyrrolidine-1-N,N-dimethyl-N-cyano-carboxamidine;
(R)-3-[3-Fluoro-5-(3-pyridin-3-yl-ureido)-phenoxy]-pyrrolidine-1-sulfonic acid dimethylamide;
(R)-3-[3-Fluoro-5-(pyridin-2-yl-ureido)-phenoxy]-pyrrolidine-1-N,N-dimethyl-N-cyano-carboxamidine;
(S)-3-[3-Fluoro-5-(3-pyridin-3-yl-ureido)-phenoxy]-pyrrolidine-1-carboxylic acid methyl ester;
(S)-3-{3-Fluoro-5-[3-(6-methyl-pyridin-3-yl)-ureido]-phenoxy}-pyrrolidine-1-carboxylic acid methyl ester;
(R)-3-{3-Fluoro-5-[3-(6-methyl-pyridin-3-yl)-ureido]-phenoxy}-pyrrolidine-1-carboxylic acid methyl ester;
(R)-3-[3-Fluoro-5-(3-pyridin-3-yl-ureido)-phenoxy]-pyrrolidine-1-carboxylic acid methyl ester;

(S)-1-{3-Fluoro-5-[1-(propane-2-sulfonyl)-pyrrolidin-3-yloxy]-phenyl}-3-pyridin-3-yl-urea;
(S)-1-{3-Fluoro-5-[1-(propane-2-sulfonyl)-pyrrolidin-3-yloxy]-phenyl}-3-(6-methyl-pyridin-3-yl)-urea;
(S)-1-{3-Fluoro-5-[1-(ethane-2-sulfonyl)-pyrrolidin-3-yloxy]-phenyl}-3-pyridin-3-yl-urea;
(S)-1-{3-Fluoro-5-[1-(ethane-2-sulfonyl)-pyrrolidin-3-yloxy]-phenyl}-3-(6-methyl-pyridin-3-yl)-urea;
(R)-1-{3-Fluoro-5-[1-(ethane-2-sulfonyl)-pyrrolidin-3-yloxy]-phenyl}-3-pyridin-3-yl-urea;
(S)-1-{3-Fluoro-5-[1-(methane-2-sulfonyl)-pyrrolidin-3-yloxy]-phenyl}-3-(6-methyl-pyridin-3-yl)-urea;
(R)-1-{3-Fluoro-5-[1-(ethane-2-sulfonyl)-pyrrolidin-3-yloxy]-phenyl}-3-(6-methyl-pyridin-3-yl)-urea;
(R)-1-{3-Fluoro-5-[1-(propane-2-sulfonyl)-pyrrolidin-3-yloxy]-phenyl}-3-(6-methyl-pyridin-3-yl)-urea;
(S)-4-{3-Fluoro-5-[3-(6-methyl-pyridin-3-yl)-ureido]-phenoxy}-[(S)-2-methoxymethyl]-pyrrolidine-1-sulfonic acid dimethylamide;
(S)-4-{3-Fluoro-5-[3-(6-methyl-pyridin-3-yl)-ureido]-phenoxy}-[(S)-2-methoxymethyl]-pyrrolidine-1-carboxylic acid methyl ester;
(R)-1-{3-(1-Ethanesulfonyl-[(R)-4-methoxy]-pyrrolidin-3-yloxy)-5-fluoro-phenyl}-3-(6-methyl-pyridin-3-yl)-urea;
(R)-1-{3-(1-Ethanesulfonyl-[(S)-5-methoxymethyl]-pyrrolidin-3-yloxy)-5-fluoro-phenyl}-3-pyridin-3-yl-urea;
(R)-1-{3-(1-Ethanesulfonyl-[(S)-5-methoxymethyl]-pyrrolidin-3-yloxy)-5-fluoro-phenyl}-3-(6-methyl-pyridin-3-yl)-urea;
1-[3-Fluoro-5-(R)-(3-oxo-(S)-tetrahydro-pyrrolo[1,2-c]oxazol-6-yloxy)-phenyl]-3-pyridin-3-yl-urea; and
1-[3-Fluoro-5-(R)-(3-oxo-(S)-tetrahydro-pyrrolo[1,2-c]oxazol-6-yloxy)-phenyl]-3-(6-methyl-pyridin-3-yl)-urea, or a single stereoisomer, mixture of stereoisomers, pharmaceutically acceptable salt, solvate, or a solvate of a pharmaceutically acceptable salt thereof.

The following group of compounds are particularly preferred (individually and collectively) as compounds of the present invention, and in connection with their formulations, methods of manufacture and use:

(R)-1-[3-(1-Acetyl-piperidin-3-yloxy)-5-fluoro-phenyl]-3-pyridin-3-yl-urea;
(R)-3-{3-Fluoro-5-[3-(6-methyl-pyridin-3-yl)-ureido]-phenoxy}-piperidine-1-carboxylic acid methyl ester;
(S)-3-{3-Fluoro-5-[3-(6-methyl-pyridin-3-yl)-ureido]-phenoxy}-piperidine-1-carboxylic acid methyl ester;
(S)-3-[3-Fluoro-5-(3-pyridin-3-yl-ureido)-phenoxy]-pyrrolidine-1-sulfonic acid dimethylamide;
1-[(R)-3-(1-Acetyl-(R)-5-methoxymethyl-pyrrolidin-3-yloxy)-5-fluoro-phenyl]-3-pyridin-3-yl-urea;
4-{3-fluoro-5-[(R)-3-(6-methyl-pyridin-3-yl)-ureido]phenoxy}-(R)-2-methoxymethyl -pyrrolidine-1-carboxylic acid methyl ester;
(S)-1-[3-(1-Ethanesulfonyl-piperidin-3-yloxy)-5-fluoro-phenyl]-3-(6-methyl-pydridin-3-yl)-urea;
(S)-1-{3-Fluoro-5-[3-(6-methyl-pyridin-3-yl)-ureido]-phenoxy}-piperidine-1-carboxylic acid methyl ester;
(R)-3-{3-Fluoro-5-[3-(6-methyl-pyridin-3-yl)-ureido]-phenoxy}-piperidine-1-carboxylic acid methyl ester;
(S)-1-[3-Fluoro-5-(1-methanesulfonyl-piperidin-3-yloxy)-phenyl]-3-pyridin-3-yl-urea;
(R)-3-[3-Fluoro-5-(3-pyridin-3-yl-ureido)-phenoxy]-pyrrolidine-1-sulfonic acid dimethylamide;
(R)-1-{3-Fluoro-5-[1-(ethane-2-sulfonyl)-pyrrolidin-3-yloxy]-phenyl}-3-(6-methyl-pyridin-3-yl)-urea;
(S)-4-{3-Fluoro-5-[3-(6-methyl-pyridin-3-yl)-ureido]-phenoxy}-[(S)-2-methoxymethyl]-pyrrolidine-1-sulfonic acid dimethylamide;
(S)-4-{3-Fluoro-5-[3-(6-methyl-pyridin-3-yl)-ureido]-phenoxy}-[(S)-2-methoxymethyl]-pyrrolidine-1-carboxylic acid methyl ester;
(R)-1-{3-(1-Ethanesulfonyl-[(S)-5-methoxymethyl]-pyrrolidin-3-yloxy)-5-fluoro-phenyl}-3-pyridin-3-yl-urea;
1-[3-Fluoro-5-(R)-(3-oxo-(S)-tetrahydro-pyrrolo[1,2-c]oxazol-6-yloxy)-phenyl]-3-pyridin-3-yl-urea; and
1-[3-Fluoro-5-(R)-(3-oxo-(S)-tetrahydro-pyrrolo[1,2-c]oxazol-6-yloxy)-phenyl]-3-(6-methyl-pyridin-3-yl)-urea, or a single stereoisomer, mixture of stereoisomers, pharmaceutically acceptable salt, solvate, or a solvate of a pharmaceutically acceptable salt thereof.

UTILITY, TESTING AND ADMINISTRATION

Utility

The compounds of the present invention are selective for and modulate the cardiac sarcomere, and are useful to bind to and/or potentiate the activity of cardiac myosin, increasing the rate at which myosin hydrolyzes ATP. As used in this context, "modulate" means either increasing or decreasing myosin activity, whereas "potentiate" means to increase activity. It has also been determined in testing representative compounds of the invention, that their administration can also increase the contractile force in cardiac muscle fiber.

The compounds, pharmaceutical formulations and methods of the invention are used to treat heart disease, including but not limited to: acute (or decompensated) congestive heart failure, and chronic congestive heart failure; particularly diseases associated with systolic heart dysfunction. Additional therapeutic utilities include administration to stabilize heart function in patients awaiting a heart transplant, and to assist a stopped or slowed heart in resuming normal function following use of a bypass pump.

Testing

ATP hydrolysis is employed by myosin in the sarcomere to produce force. Therefore, an increase in ATP hydrolysis would correspond to an increase in the force or velocity of muscle contraction. In the presence of actin, myosin ATPase activity is stimulated >100 fold. Thus, ATP hydrolysis not only measures myosin enzymatic activity but also its interaction with the actin filament. A compound that modulates the cardiac sarcomere can be identified by an increase or decrease in the rate of ATP hydrolysis by myosin, preferably exhibiting a 1.4 fold increase at concentrations less than 10 µM (more preferably, less than 1 µM). Preferred assays for such activity will employ myosin from a human source, although myosin from other organisms can also be used. Systems that model the regulatory role of calcium in myosin binding are also preferred.

Alternatively, a biochemically functional sarcomere preparation can be used to determine in vitro ATPase activity, for example, as described in U.S. Ser. No. 09/539,164, filed Mar. 29, 2000. The functional biochemical behavior of the sarcomere, including calcium sensitivity of ATPase hydrolysis, can be reconstituted by combining its purified individual components (particularly including its regulatory components and myosin). Another functional preparation is the in vitro motility assay. It can be performed by adding test compound to a myosin-bound slide and observing the velocity of actin filaments sliding over the myosin covered glass surface (Kron S J. (1991) Methods Enzymol. 196:399-416).

The in vitro rate of ATP hydrolysis correlates to myosin potentiating activity, which can be determined by monitoring the production of either ADP or phosphate, for example as described in Ser. No. 09/314,464, filed May 18, 1999. ADP production can also be monitored by coupling the ADP production to NADH oxidation (using the enzymes pyruvate kinase and lactate dehydrogenase) and monitoring the NADH level either by absorbance or fluorescence (Greengard, P., *Nature* 178 (Part 4534): 632-634 (1956); *Mol Pharmacol* 1970 January; 6(1):31-40). Phosphate production can be monitored using purine nucleoside phosphorylase to couple phosphate production to the cleavage of a purine analog, which results in either a change in absorbance (*Proc Natl Acad Sci USA* 1992 Jun. 1; 89(11):4884-7) or fluorescence (*Biochem J* 1990 March 1; 266(2):611-4). While a single measurement can be employed, it is preferred to take multiple measurements of the same sample at different times in order to determine the absolute rate of the protein activity; such measurements have higher specificity particularly in the presence of test compounds that have similar absorbance or fluorescence properties with those of the enzymatic readout.

Test compounds can be assayed in a highly parallel fashion using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

A preferred method uses a 384 well plate format and a 25 µL reaction volume. A pyruvate kinase/lactate dehydrogenase coupled enzyme system (Huang T G and Hackney D D. (1994) J Biol Chem 269(23):16493-16501) is used to measure the rate of ATP hydrolysis in each well. As will be appreciated by those in the art, the assay components are added in buffers and reagents. Since the methods outlined herein allow kinetic measurements, incubation periods are optimized to give adequate detection signals over the background. The assay is done in real time giving the kinetics of ATP hydrolysis, which increases the signal to noise ratio of the assay.

Modulation of cardiac muscle fiber contractile force can be measured using detergent permeabilized cardiac fibers (also referred to as skinned cardiac fibers), for example, as described by Haikala H, et al (1995) J Cardiovasc Pharmacol 25(5):794-801. Skinned cardiac fibers retain their intrinsic sarcomeric organization, but do not retain all aspects of cellular calcium cycling, this model offers two advantages: first, the cellular membrane is not a barrier to compound penetration, and second, calcium concentration is controlled. Therefore, any increase in contractile force is a direct measure of the test compound's effect on sarcomeric proteins. Tension measurements are made by mounting one end of the muscle fiber to a stationary post and the other end to a transducer that can measure force. After stretching the fiber to remove slack, the force transducer records increased tension as the fiber begins to contract. This measurement is called the isometric tension, since the fiber is not allowed to shorten. Activation of the permeabilized muscle fiber is accomplished by placing it in a buffered calcium solution, followed by addition of test compound or control. When tested in this manner, compounds of the invention caused an increase in force at calcium concentrations associated with physiologic contractile activity, but very little augmentation of force in relaxing buffer at low calcium concentrations or in the absence of calcium (the EGTA data point).

Selectivity for the cardiac sarcomere and cardiac myosin can be determined by substituting non-cardiac sarcomere components and myosin in one or more of the above-described assays and comparing the results obtained against those obtained using the cardiac equivalents.

A compound's ability to increase observed ATPase rate in an in vitro reconstituted sarcomere assay could result from the increased turnover rate of S1-myosin or, alternatively, increased sensitivity of a decorated actin filament to $Ca^{++}$-activation. To distinguish between these two possible modes of action, the effect of the compound on ATPase activity of S1 with undecorated actin filaments is initially measured. If an increase of activity is observed, the compound's effect on the Ca-responsive regulatory apparatus could be disproved. A second, more sensitive assay, can be employed to identify compounds whose activating effect on S1-myosin is enhanced in the presence of a decorated actin (compared to pure actin filaments). In this second assay activities of cardiac-S1 and skeletal-S1 on cardiac and skeletal regulated actin filaments (in all 4 permutations) are compared. A compound that displays its effect on cardiac-S1/cardiac actin and cardiac-S1/skeletal actin, but not on skeletal-S1/skeletal actin and skeletal-S1/cardiac actin systems, can be confidently classified as cardiac-S1 activator.

Initial evaluation of in vivo activity can be determined in cellular models of myocyte contractility, e.g., as described by Popping S, et al ((1996) Am. J. Physiol. 271: H357-H364) and Wolska B M, et al ((1996) Am. J. Physiol. 39:H24-H32). One advantage of the myocyte model is that the component systems that result in changes in contractility can be isolated and the major site(s) of action determined. Compounds with cellular activity (for example, selecting compounds having the following profile: >120% increase in fractional shortening over basal at 2 µM, limited changes in diastolic length (<5% change), and no significant decrease in contraction or relaxation velocities) can then be assessed in whole organ models, such as such as the Isolated Heart (Langendorff) model of cardiac function, in vivo using echocardiography or invasive hemodynamic measures, and in animal-based heart failure models, such as the Rat Left Coronary Artery Occlusion model. Ultimately, activity for treating heart disease is demonstrated in blinded, placebo-controlled, human clinical trials.

Administration

The compounds of Formula I are administered at a therapeutically effective dosage, e.g., a dosage sufficient to provide treatment for the disease states previously described. While human dosage levels have yet to be optimized for the compounds of the invention, generally, a daily dose is from about 0.05 to 100 mg/kg of body weight, preferably about 0.10 to 10.0 mg/kg of body weight, and most preferably about 0.15 to 1.0 mg/kg of body weight. Thus, for administration to a 70 kg person, the dosage range would be about 3.5 to 7000 mg per day, preferably about 7.0 to 700.0 mg per day, and most preferably about 10.0 to 100.0 mg per day. The amount of active compound administered will, of course, be dependent on the subject and disease state being treated, the severity of the affliction, the manner and schedule of administration and the judgment of the prescribing physician; for example, a likely dose range for oral administration would be about 70 to 700 mg per day, whereas for intravenous administration a likely dose range would be about 700 to 7000 mg per day, the active agents being selected for longer or shorter plasma half-lives, respectively.

Administration of the compounds of the invention or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the present invention.

Pharmaceutically acceptable compositions include solid, semi-solid, liquid and aerosol dosage forms, such as, e.g., tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see *Remington's Pharmaceutical Sciences*, Mack Publishing Company, Easton, Pa.

In addition, the compounds of the invention can be co-administered with, and the pharmaceutical compositions can include, other medicinal agents, pharmaceutical agents, adjuvants, and the like. Suitable additional active agents include, for example: therapies that retard the progression of heart failure by down-regulating neurohormonal stimulation of the heart and attempt to prevent cardiac remodeling (e.g., ACE inhibitors or β-blockers); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide).

In one preferred embodiment, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2-2% of the active agent in solution.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

Use in Screening

Generally, to employ the compounds of the invention in a method of screening for myosin binding, myosin is bound to a support and a compound of the invention is added to the assay. Alternatively, the compound of the invention can be bound to the support and the myosin added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like. See, e.g., U.S. Pat. No. 6,495,337, incorporated herein by reference.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

(R)-1-[3-(1-Acetyl-piperidin-3-yloxy)-5-fluoro-phenyl]-3-pyridin-3-yl-urea 1A. (R)-3-Hydroxypiperidine (S)-1-(+)-camphor-10-sulfonate salt. Four 50 L 3-neck RBF extractors equipped with a mechanical stirrer under nitrogen, were charged with 10.76 kg (46.14 mol) (S)-1-(+)-camphor-10-sulfonic acid, 23.3 L (2.5 vol) ethanol (absolute), and 9.34 kg (92.27 mol) 3-hydroxypiperidine. The solution was then brought to turbidity with the addition of 142 L MTBE. The solution was stirred overnight, and the solids were filtered and rinsed with 8 L (1:1) MTBE:EtOH, 8 L (2:1) MTBE:EtOH, and 8 L MTBE to afford 10.68 kg white solid (35% yield, 75.8% ee, these numbers are an average of the two lots). These solids were charged to a 22 L 3-neck RBF fitted with a mechanical stirrer, thermometer, and reflux condenser. The flasks were charged with 10.7 L (1 vol) ethanol (absolute), and the solution was warmed to 55° C. The heat was turned off, and the solution cooled to room temperature overnight. The solids were filtered and rinsed with 1.5 L (2×) (1:1) MTBE:EtOH, and 3 L (2×) MTBE to afford 6.95 kg of (R)-3-hydroxypiperidine (S)-1-(+)-camphor-10-sulfonate salt as a white solid in 22.6% yield (theoretical yield=30.79 kg, purity=97.2% ee).

1B. 1-((R)-3-Hydroxy-piperidin-1-yl)-ethanone. One 50 L and two 22 L extractors equipped with mechanical stirrers, stoppers, and nitrogen bubblers were purged with nitrogen for at least ten minutes. The extractors were charged with 3.21 kg (38.21 mol) sodium bicarbonate and 27.9 L (4 vol) water. (R)-3-Hydroxypiperidine (S)-1-(+)-camphor-10-sulfonate salt 6.95 kg (20.84 mol) was charged to the extractors, followed by the addition of 27.9 L (4 vol) dichloromethane. The solutions were stirred for 30 min, then 2.36 L (25.0 mol) acetic anhydride was added portion-wise for 2 hours to ensure slow off-gassing. The reaction was allowed to stir overnight and was deemed complete by TLC analysis of the aqueous and organic layers (100% methanol/ninhydrin stain). The reaction was concentrated, and 28 L toluene was used to assist the water removal. Once the solid was dry, it was divided between two 20 L round bottom flasks (5.8 kg/flask). 24 L (1:1) MTBE: DCM, 8 kg (1.2 mass eq) sodium sulfate, and 4 kg (47.61 mol) sodium bicarbonate were added, and the solution was stirred overnight (without vacuum). The solids were filtered and rinsed with 24 L (12 L per flask) dichloromethane. The filtrates were split into 4 L quantities per 20 L carboys and diluted with 1690 L (8 L per carboy) MTBE. The solutions sat for 12 hours, and the precipitated solids were filtered and concentrated to afford 2.92 kg 1-((R)-3-hydroxy-piperidin-1-yl)-ethanone in 98% yield as a yellow oil (theoretical yield=2.98 kg, purity=95.2% and 97.4% ee).

1C. 1-[(R)-3-(3-Fluoro-5-nitro-phenoxy)-piperidin-1-yl]-ethanone and 1-[(R)-3-(3,5-Difluoro-phenoxy)-piperidin-1-yl]-ethanone. Two 22 L 3-neck RBFs equipped with cooling baths, mechanical stirrers, thermowells, y-adapters, rubber septa, and nitrogen bubblers were purged with nitrogen for at least ten minutes. The flasks were charged with 0.884 kg (22.1 mol) sodium hydride (0.442 kg apiece) and 4.86 L (2 vol) NMP (2.43 L apiece). The flasks were cooled to 0±5° C. in an ice/brine bath. A solution of 2.43 kg (17 mol) 1-((R)-3-hydroxy-piperidin-1-yl)-ethanone (1.22 kg apiece) and 0.058 kg (0.85 mol) imidazole (0.029 kg apiece) in 4.86 L (2 vol) NMP (2.43 L apiece) was added dropwise over 1.5 hours to the flask, maintaining an internal temperature below 5±5° C. The solution stirred for 2 hours, then was cannulated into two 22 L 3-neck RBFs equipped with cooling baths, mechanical stirrers, thermowells, y-adapters, rubber septa, and nitrogen bubblers that were purged with nitrogen for at least ten minutes and charged with a solution of 2.70 kg (16.97 mol) 3,5-difluoronitrobenzene (1.35 L apiece) in 2.43 L (1 vol) NMP (1.22 L apiece) that was cooled to 0±5° C. in an ice/brine bath. The cannulation lasted for 2 hours, maintaining an internal temperature below 10±5° C. The solution was warmed to 70±5° C. for 11 hours, and was deemed complete by TLC (1:1 hexanes:acetone/PMA stain) and GC (IPC attached). The solution was cooled and poured into four 50 L extractors with 54 L MTBE and 54 L water. The layers were separated, and the aqueous layer was reextracted with 54 L MTBE. The combined organic layers were washed with 54 L (3×) water and 54 L brine. The organics were dried over sodium sulfate, filtered and concentrated to afford 4.54 kg of a mixture of 1-[(R)-3-(3-fluoro-5-nitro-phenoxy)-piperidin-1-yl]-ethanone and 1-[(R)-3-(3,5-difluoro-phenoxy)-piperidin-1-yl]-ethanone in 95% yield (theoretical yield=4.79 kg, purity=83.2% 1-[(R)-3-(3-fluoro-5-nitro-phenoxy)-piperidin-1-yl]-ethanone and 9.2% 1-[(R)-3-(3,5-difluoro-phenoxy)-piperidin-1-yl]-ethanone and 98.0% ee).

1D. 1-[(R)-3-(3-Amino-5-fluoro-phenoxy)-piperidin-1-yl]-ethanone. Three 22 L 3-neck RBFs equipped with heating mantles, mechanical stirrers, thermowells, condensers, and nitrogen bubblers were purged under nitrogen for at least ten minutes. The flasks were charged with 0.454 kg (10 wt %) Pd/C, and 13.62 L (3 vol) methanol. A solution of 4.54 kg (~16.1 mol) of a mixture of 1-[(R)-3-(3-fluoro-5-nitro-phenoxy) -piperidin-1-yl]-ethanone and 1-[(R)-3-(3,5-difluoro-phenoxy)-piperidin-1-yl]-ethanone in 4.54 L (1 vol) methanol was then charged to the flasks, and an additional 4.54 L (1 vol) methanol was added to the flasks. The solutions were warmed to a gentle reflux, and a solution of 5.07 kg (80.4 mol) ammonium formate in 3.63 L water was then added dropwise for 10 hours. The reactions were deemed complete by TLC (1:1 hexanes:acetone/PMA stain) and HPLC (IPC attached), and were filtered through celite and concentrated. The concentrate was transferred to two 50 L extractors, and was partitioned between 47.2 L MTBE and 17.7 L 3N HCl. The layers were separated, and the organics were extracted with 6 L (2×) 3N HCl. The aqueous layers were neutralized with 3.54 kg NaOH to pH ~7, then 9.6 L saturated sodium bicarbonate was added. The aqueous layers were then extracted with 6 L (3×) DCM. The combined organics were washed with 18 L brine, dried over sodium sulfate, filtered and concentrated to yield 3.06 kg of 1-[(R)-3-(3-amino-5-fluoro-phenoxy)-piperidin-1-yl]-ethanone in 75% yield as a thick brown oil (theoretical yield=4.06 kg, purity=90.7% and 95.4% ee).

1E. 1-[(R)-3-(3-Amino-5-fluoro-phenoxy)-piperidin-1-yl]-ethanone HCl salt. A 22 L 3-neck RBF equipped with a cooling bath, an addition funnel, mechanical stirrer, thermocouple and nitrogen bubbler was purged with nitrogen for at least ten minutes. The flask was charged with 0.612 kg (2.43 mol) 1-[(R)-3-(3-amino-5-fluoro-phenoxy)-piperidin-1-yl]-ethanone and 12.2 L (20 vol) ethyl acetate. The solution was cooled to 0±5° C. in an ice/brine bath, and 1.46 L (2.92 mol) 2M HCl in ether was added dropwise for 20 minutes, maintaining the internal temperature below 10° C. The solution stirred for 2 hours at 0±5° C., and the solid was filtered under a nitrogen atmosphere and rinsed with 6.0 L (10 vol) ethyl acetate. The solid was dried at 50±5° C. under vacuum for 2 days to afford 693 g of 1-[(R)-3-(3-amino-5-fluoro-phenoxy)-piperidin-1-yl]-ethanone HCl salt in 99% yield as an off-white solid (theoretical yield=0.700 kg, purity=94.2% and 97.6% ee).

1F. (R)-1-[3-(1-Acetyl-piperidin-3-yloxy)-5-fluoro-phenyl]-3-pyridin-3-yl-urea. A 22 L 3-neck RBF equipped with a cooling bath, mechanical stirrer, thermocouple, and nitrogen bubbler was purged with nitrogen for at least ten minutes. The flask was charged with 1.441 kg (4.990 mol) 1-[(R)-3-(3-amino-5-fluoro-phenoxy)-piperidin-1-yl]-ethanone HCl salt and 14.4 L (10 vol) dichloromethane. The solution was stirred, and 0.710 kg (5.489 mol) DIPEA was charged. The solution was cooled to 10±5° C. in an ice/brine bath. The reaction was charged with 0.659 kg (5.489 mol) 3-isocyanato-pyridine and the solution warmed to room temperature and stirred for three hours. The reaction was monitored by TLC (1:9 methanol:ethyl acetate/PMA stain) and HPLC (IPC attached). The reaction stirred at room temperature for five more hours, and another 0.009 kg (0.075 mol) 3-isocyanato-pyridine was added. The solution stirred for 15 more hours, and the reaction was deemed complete. The solution was poured into a 50 L extractor containing 14.4 L (10 vol) saturated sodium bicarbonate, and the flask was rinsed with an additional 1.44 L (1 vol) dichloromethane. The layers were separated, and the organic layer was washed with 14.4 L (2×10 vol) water. The organic layer was dried with 1.69 kg sodium sulfate for at least 20 minutes before proceeding to the next step.

1G. Purification of (R)-1-[3-(1-acetyl-piperidin-3-yloxy)-5-fluoro-phenyl]-3-pyridin-3-yl-urea. The DCM mixture from Example 1F was concentrated at 35±5° C. under reduced pressure until condensation ceased, then for one hour longer at 45±5° C. The contents were transferred to a 22 L 3-neck RBF equipped with a heating mantle, condenser, mechanical stirrer, thermocouple, and nitrogen bubbler that had been purged with nitrogen for at least ten minutes. The rotovap flask was rinsed with 14.5 L ethyl acetate, and the rinse was poured into the 22 L 3-neck RBF. The solution was warmed to 55±5° C., then was cooled to room temperature for ten minutes. The suspension was then heated to 60±5° C. for an hour. The heater was turned off and the solution gradually cooled to room temperature. The solids were filtered and washed with 8.7 L ethyl acetate, The crystals were dried at 45±5° C. for 13.5 hours. The crystals were then transferred to a 22 L 3-neck RBF equipped with a heating mantle, condenser, mechanical stirrer, thermocouple, and nitrogen bubbler that had been purged with nitrogen for at least ten minutes. The flask was then charged with 14.5 L water, and the suspension was heated to 50±5° C. for 34 hours. The solid was filtered and dried under vacuum at 45±5° C. to afford 2.46 kg of an off-white solid. The crystals were then transferred to a 22 L 3-neck RBF equipped with a heating mantle, condenser, mechanical stirrer, thermocouple, and nitrogen bubbler that had been purged with nitrogen for at least ten minutes. 11.6 L water was then charged, and the solution was warmed to 50±5° C. for 5 hours. The heat was turned off, and the solution was allowed to cool to room temperature. The solution was warmed to 50±5° C. for a second cycle of 20 hours. The solids were filtered and rinsed with 14.5 L water. They were then charged to a 22 L 3-neck RBF equipped with a heating mantle, condenser, mechanical stirrer, thermocouple, and nitrogen bubbler that had been purged with nitrogen for at least ten minutes, and 12.5 L water was added. The solution was warmed to 50±5° C. for 5.5 hours. The crystals were filtered and rinsed with 14.5 L water, and dried under vacuum at 50±5° C. to afford 2.38 kg off-white solid. The solid was then taken up in 8 L water, and was concentrated on the rotovap with a bath temperature of 50±5° C. 16 L Water was added to the flasks portionwise, and the solids were filtered and rinsed with 15.5 L water. The crystals were dried under vacuum at 50±5° C. to afford 2.28 kg of the purified title compound, (R)-1-[3-(1-acetyl-piperidin-3-yloxy)-5-fluorophenyl]-3-pyridin-3-yl-urea, in 61% yield as an off-white solid (mp=145° C., theoretical yield=3.74 kg, purity=98.7% and 99.2% ee).

Example 2

3-{3-Fluoro-5-[3-(6-methyl-pyridin-3-yl)-ureido]-phenoxy}-pyrrolidine-1-sulfonic Acid Dimethylamide 2A. (R)-t-butyl-3-(3-fluoro-5-nitrophenoxy)-pyrrolidine-1-carboxylate. A round bottom flask was charged with DMF (300 mL), and NaH (12.8 g, 320 mmol, 1.2 eq) and stirred in an ice bath. A solution of N-tert-butyl-(R)-3-hydroxypyrrolidine (50 g, 267 mmol, 1 eq) in DMF (100 mL) was added gradually into the flask and stirred for approximately 30 minutes. A solution of difluoronitrobenzene (51 g, 320 mmol, 1.2 eq) and DMF (50 mL) was added dropwise for approximately 30 minutes. The resulting solution was allowed to warm to room temperature and stirred for approximately 4 hours. Water was added to the reaction mixture. The reaction mixture was extracted with ethyl acetate. The organic layer was washed with water, saturated sodium bicarbonate and brine solutions. The organics were dried with sodium sulfate, filtered, and concentrated. The residue was purified by silica chromatography using dichloromethane and 5% methanol in dichloromethane as the elute to yield 39 g of (R)-tert-butyl-3-(3-nitro-5-fluorophenoxy)-pyrrolidine-1-carboxylate as an orange/yellow oil.

2B. (R)-t-butyl-3-(3-amino-5-fluorophenoxy)-pyrrolidine-1-carboxylate. A mixture of 45 g of (R)-tert-butyl-3-(3-amino-5-fluorophenoxy)-pyrrolidine-1-carboxylate and 4.5 g of palladium hydroxide (10% by weight) in 200 mL of MeOH under $H_2$ atm (55 psi) stirred for 16 hours. The heterogenous mixture was filtered through a pad of diatomaceous earth and rinsed with methanol, dichloromethane and then concentrated to reddish-brown, viscous oil of (R)-tert-butyl-3-(3-amino-5-fluorophenoxy)-pyrrolidine-1-carboxylate (89% yield).

2C. 3-{3-Fluoro-5-[3-(6-methyl-pyridin-3-yl)-ureido]-phenoxy}-pyrrolidine-1-carboxylic acid tert-butyl ester. A round bottom flask was charged with triphosgene (3 g, 10 mmol, 1 eq) and THF (33 mL) and chilled to 0° C. A solution of 5-amino-2-methylpyridine (3.3 g, 10 mmol, 3 eq), diisopropylethylamine (10.3 mL, 60 mmol, 6 eq) and THF (33 mL) was added dropwise to the triphosgene solution. The mixture was allowed to warm to room temperature and stirred for 30 minutes. A solution of (R)-tert-butyl-3-(3-amino-5-fluorophenoxy)-pyrrolidine-1-carboxylate (3.0 g, 10 mmol, 1 eq) in THF (33 mL) was added dropwise. The resultant reaction mixture was stirred overnight at room temperature. The reaction mixture was quenched with a saturated sodium bicarbonate solution and the THF was removed in vacuo. The mixture was extracted with dichloromethane. The dichloromethane solution was washed with saturated sodium bicarbonate and brine. The organic layers were dried with sodium sulfate, filtered and concentrated. The residue was purified by silica column chromatography with 500 mL of ethyl acetate, 500 mL of 2.5% methanol in ethyl acetate, 500 mL of 5% methanol in ethyl acetate, 500 mL 7.5% methanol in ethyl acetate, and 10% methanol in ethyl acetate as the gradient elute to yield 3.4 g of 3-{3-fluoro-5-[3-(6-methyl-pyridin-3-yl)-ureido]-phenoxy}-pyrrolidine-1-carboxylic acid tert-butyl ester as a light yellow solid.

2D. 1-[3-Fluoro-5-(pyrrolidin-3-yloxy)-phenyl]-3-(6-methyl-pyridin-3-yl)-urea. To 6.5 g of 3-{3-fluoro-5-[3-(6-methyl-pyridin-3-yl)-ureido]-phenoxy}-pyrrolidine-1-carboxylic acid tert-butyl ester was added 20 mL of a 1:1 mixture of trifluoroacetic acid and dichloromethane at room temperature and the resultant reaction mixture was stirred for 2 hours. The reaction mixture was concentrated. To the residue was added 5 mL of saturated brine solution and 1 N NaOH was added until a pH of 10 was observed. The mixture was extracted with ethyl acetate. The organics were dried with sodium sulfate, filtered, and concentrated to 1-[3-fluoro-5-(pyrrolidin-3-yloxy)-phenyl]-3-(6-methyl-pyridin-3-yl)-urea, a compound of Formula I, as an oil that was used directly in the subsequent reaction.

2E. 3-{3-Fluoro-5-[3-(6-methyl-pyridin-3-yl)-ureido]-phenoxy}-pyrrolidine-1-sulfonic acid dimethylamide. A round bottom flask was charged with the 1-[3-fluoro-5-(pyrrolidin-3-yloxy)-phenyl]-3-(6-methyl-pyridin-3-yl)-urea (3 g, 9.1 mmol, 1 eq), triethylamine (3.6 mL, 27 mmol, 3 eq), dimethylsufamoyl chloride (1.2 g, 11 mmol, 1.2 eq), and dichloromethane (20 mL). The reaction mixture was stirred at room temperature for 1 hour. To the reaction was added saturated sodium bicarbonate solution. The resultant mixture was extracted with ethyl acetate. The organics were washed with brine and concentrated. The residue was purified by silica column chromatography using 10% methanol in ethyl acetate as the elute to yield 2.8 g of the title compound, 3-{3-fluoro-5-[3-(6-methyl-pyridin-3-yl)-ureido]-phenoxy}-pyrrolidine-1-sulfonic acid dimethylamide as an off-white solid. MS (M+1) 438.

Example 3

(S)-1-{3-Fluoro-5-[1-(ethane-2-sulfonyl)-piperidin-3-yloxy]-phenyl}-3-pyridin-3-yl-urea and (S)-3-{3-Fluoro-5-[3-6-methyl-pyridin-3-yl)-ureido]-phenoxy}-piperidine-1-carboxylic Acid Methyl Ester 3A. (S)-3-Hydroxypiperidine (R)-1-(+)-camphor-10-sulfonate salt. Six 4 L Erlenmeyer flasks were charged with (R)-1-(−)-camphor-10-sulfonic acid (215.2 g), absolute ethanol (480 mL), and 3-hydroxypiperidine (186.8 g). The solutions were then brought to turbidity with addition of tert-butyl methyl ether (MTBE, 4.84 L). The solution was stirred for 48 hours, and the solids were combined, filtered and rinsed with (1:1) MTBE:EtOH (960 mL), (2:1) MTBE:EtOH (960 mL), MTBE (960 mL) to afford white solid (1.27 kg, 35% yield, 90.8% ee). The obtained solids were charged to a 4 L Erlenmeyer flask with 1.27 L absolute ethanol. The mixture was stirred and warmed to 60° C. for 1 hour until the solids were completely dissolved. The heat was turned off, and the solution cooled to room temperature and stirred overnight. The solids were filtered and rinsed with (1:1) MTBE:EtOH (2×180 mL), MTBE (2×360 mL) to afford the 850 g of (S)-3-hydroxypiperidine (R)-1-(+)-camphor-10-sulfonate salt desired product as a white solid (yield 23%, e.e. 99.2%).

3B. 3-Hydroxy-piperidine-1-carboxylic acid tert-butyl ester. To a mixture of sodium bicarbonate (403.3 g, 4.8 mol) and water (1.6 L) was added (S)-3-hydroxypiperidine (R)-1-(−)-camphor-10-sulfonic acid salt (3, 400.14 g, 1.2 mol) and dichloromethane (1.6 L). The mixture was stirred for 30 minutes and cooled by ice bath. To the mixture was added di-tert-butyl dicarbonate (288.1 g, 1.32 mol) portionwise in 30 minutes. The mixture was stirred at room temperature overnight. The mixture was diluted with dichloromethane (4.8 L) and H2O (4.8 L) and separated in separation funnel. The organic layer was washed with brine (2 L), dried ($Na_2SO_4$) and concentrated to give the desired product (S)-3-hydroxy-piperidine-1-carboxylic acid tert-butyl ester in quantitative yield (241.5 g).

3C. 3-(3-Fluoro-5-nitro-phenoxy)-piperidine-1-carboxylic acid tert-butyl ester. A 3 L 3-neck round bottom flask was charged with sodium hydride (60% in oil, 54.24 g, 1.356 mol) and DMF (1 L). The flask was cooled in an ice bath, a solution of (S)-3-hydroxy-piperidine-1-carboxylic acid tert-butyl ester alcohol (210 g, 1.043 mol) in DMF (500 mL) was added dropwise over 30 minutes to the flask, maintaining an internal temperature below 5° C. The solution was stirred for 1 hour, then was added via a canula into a 5 L 3-neck round bottom flask charged with a solution of 3,5-difluoronitrobenzene (169.25 g, 1.064 mol) that was cooled in an ice bath. The addition lasted for 1 hour, maintaining an internal temperature below 5° C. The reaction mixture was warmed to room temperature and stirred for 4 hours and diluted with 6 L ethyl acetate. The organic layer was washed with saturated ammonium chloride (4 L), sodium bicarbonate (2 L) and brine (2 L), dried ($Na_2SO_4$) and concentrated to afford the desired product (S)-3-(3-fluoro-5-nitro-phenoxy)-piperidine-1-carboxylic acid tert-butyl ester as an syrup (360 g, purity ~95%).

3D. 3-(5-Amino-3-fluoro-phenoxy)-piperidine-1-carboxylic acid tert-butyl ester. Four cylinders charged with (S)-3-(3-fluoro-5-nitro-phenoxy)-piperidine-1-carboxylic acid tert-butyl ester (50 g), 10% $Pd(OH)_2$/C (5.0 g) and MeOH (300 mL) were subjected to hydrogenation under 50 psi $H_2$. The mixture was stirred vigorously overnight. The mixture was filtered through a pad of diatomaceous earth and rinsed with methanol. The alcoholic solutions were combined and concentrated to give the aniline (S)-3-(5-amino-3-fluoro-phenoxy)-piperidine-1-carboxylic acid tert-butyl ester as syrup in quantitative yield.

3E. 3-{3-Fluoro-5-[3-(6-methyl-pyridin-3-yl)-ureido]-phenoxy}-piperidine-1-carboxylic acid tert-butyl ester. To a solution of (S)-3-(5-amino-3-fluoro-phenoxy)-piperidine-1-carboxylic acid tert-butyl ester (83.0 g, 0.267 mol) in dichloromethane (830 mL) cooled by ice bath was added 2-methyl-5-isocyanato-pyridine (73% in toluene, 46.67 g, 0.254 mol) dropwise. The mixture was warmed to room temperature and stirred for 1 hour. The mixture was loaded onto a silica gel pad (830 g), rinsed with dichloromethane (4 L) to remove impurities, then 4% MeOH in EtOAc (4 L) to elute the product. Concentration of the MeOH-EtOAc solution gave 3-{3-fluoro-5-[(S)3-(6-methyl-pyridin-3-yl)-ureido]-phenoxy}-piperidine-1-carboxylic acid tert-butyl ester as an amorphous solid (109.35 g, 92%).

3F. 1-[3-Fluoro-5-(piperidin-(S)-3-yloxy)-phenyl]-3-(6-methyl-pyridin-3-yl)-urea. To a solution of 3-{3-fluoro-5-[(S)3-(6-methyl-pyridin-3-yl)-ureido]-phenoxy}-piperidine-1-carboxylic acid tert-butyl ester (65.15 g, 147 mmol) in MeOH (147 mL) cooled by ice bath was added a solution of 4M HCl/1,4-dioxane (147 mL, 588 mmol) dropwise. The mixture was warmed to room temperature and stirred for 3 hours. After concentration, 1-[3-fluoro-5-(piperidin-(S)-3-yloxy)-phenyl]-3-(6-methyl-pyridin-3-yl)-urea was obtained as a pale yellow solid. The product (also a compound of Formula I) was used directly for the next step reaction.

3G. Preparation of 1-{3-Fluoro-5-[1-(ethane-2-sulfonyl)-piperidin-3-(S)-yloxy]-phenyl}-3-pyridin-3-yl-urea. To a mixture of 1-[3-fluoro-5-(piperidin-(S)-3-yloxy)-phenyl]-3-(6-methyl-pyridin-3-yl)-urea (147 mmol), dichloromethane (650 mL) and triethylamine (80 mL, 586 mmol) cooled by ice bath was added ethanesulfonyl chloride (13.89 mL, 147 mmol) dropwise. The mixture was warmed to room temperature and stirred for 2 hours. The mixture was then washed with saturated sodium bicarbonate (500 mL) and brine (500 mL), dried ($Na_2SO_4$) and concentrated. The obtained residue was purified by silica gel column chromatography using hexane-acetone (3:2) as eluant to afford 1-{3-fluoro-5-[1-(ethane-2-sulfonyl)-piperidin-(S)-3-yloxy]-phenyl}-3-pyridin-3-yl-urea as a white solid (50.2 g, 78.4%).

3H(S)-3-{3-Fluoro-5-[3-(6-methyl-pyridin-3-yl)-ureido]-phenoxy}-piperidine-1-carboxylic acid methyl ester. 1-[3-Fluoro-5-(piperidin-(S)-3-yloxy)-phenyl]-3-(6-methyl-pyridin-3-yl)-urea (19.6 g) in THF (400 mL) was treated sequentially with triethylmine (38 mL, 277 mmol), then slowly with methylchloroformate (5.1 mL, 66.6 mmol). After stirring for 2 hours, 50 mL of saturated $NaHCO_3$ solution was added and the mixture was stirred for 30 min. After evaporation, the residue was dissolved in EtOAc and washed with saturated ammonium chloride and water, dried ($Na_2SO_4$) and evaporated. Flash chromatography eluting with 70% acetone/hexane afforded (S)-3-{3-fluoro-5-[3-(6-methyl-pyridin-3-yl)-ureido]-phenoxy}-piperidine-1-carboxylic acid methyl ester as a white foam (17.5 g, 92%).

Example 4

Starting Materials and Intermediates for Other Compounds of Formula I 4A. (R)-4-Hydroxy-pyrrolidine-1,(S)-2-dicarboxylic acid 1-t-butyl ester. A round-bottom flask was charged with 20 g of (R)-4-hydroxy-pyrrolidine-(S)-2-carboxylic acid, 100 mL THF, and 60 mL H₂O. To the reaction mixture was added 36 mL of 20% aqueous solution of NaOH and the mixture was cooled to 0° C. To the mixture was added 40 g of Boc₂O (182 mmol, 1.2 equiv.) and the resultant mixture was allowed to warm to room temperature overnight. The reaction mixture was concentrated and adjusted to pH 2 by the addition of approximately 45 mL 4N HCl. The mixture was extracted with 200 mL EtOAC three times. The organic layer was washed with brine, water, dried over MgSO₄, filtered, and concentrated to yield (R)-4-hydroxy-pyrrolidine-1,(S)-2-dicarboxylic acid 1-tert-butyl ester (100% yield).

4B. (R)-4-Hydroxy-(S)-2-hydroxymethyl-pyrrolidine-1-carboxylic acid tert-butyl ester. A round-bottomed flask was charged with 6.53 g of LiBH₄ in 200 mL THF and the mixture was cooled to 0° C. To this mixture was added 65 g of TMSCI (600 mmol, 4 equiv.) under nitrogen. The reaction mixture was stirred at 0° C. for 30 minutes and then it was allowed to warm up to room temperature for an additional 30 minutes. The mixture was cooled down to 0° C. and 35 g of (R)₄-hydroxy-pyrrolidine-1,(S)-2-dicarboxylic acid 1-tert-butyl ester in 150 mL THF was added over one hour. The reaction was stirred for 2 hours followed by the sequential addition of 25 mL of MeOH and 12 mL of H₂O. The mixture was adjusted to pH 7 by the addition of approximately 75 mL of 4N NaOH. The mixture was concentrated to remove the THF and extracted twice with 500 mL of EtOAc. The combined organic layers were dried and concentrated to yield (R)₄-hydroxy-(S)-2-hydroxymethyl-pyrrolidine-1-carboxylic acid tert-butyl ester (90% yield).

4C. (S)-2-(tert-Butyl-dimethyl-silanyloxymethyl)-(R)4-hydroxy-pyrrolidine-1-carboxylic acid tert-butyl ester. A round-bottomed flask was charged with 29.3 g of (R)-4-hydroxy-(S)-2-hydroxymethyl-pyrrolidine-1-carboxylic acid tert-butyl ester in 270 mL DMF and the solution cooled to 0° C. To the solution was added sequentially 23 g of imidazole and 24.4 g of TBDMSCI in several portions. The reaction mixture was allowed to warm up to room temperature and stir for 2 hours. To the reaction mixture was added 500 mL of saturated NH₄Cl and 500 ml EtOAc. The organic layer was removed and washed with 500 mL saturated NH₄Cl, dried over MgSO₄, filtered and concentrated, to afford (S)-2-(tert-butyl-dimethyl-silanyloxymethyl)-(R)-4-hydroxy-pyrrolidine-1-carboxylic acid tert-butyl ester in quantitative yield.

4D. (S)-2-(tert-Butyl-dimethyl-silanyloxymethyl)-(R)-4-hydroxy-pyrrolidine-1-carboxylic acid tert-butyl ester. To 33 g of (S)-2-(tert-butyl-dimethyl-silanyloxymethyl)-(R)-4-hydroxy-pyrrolidine-1-carboxylic acid tert-butyl ester in 150 mL anhydrous DMF under nitrogen at 0° C. was added 4.8 g of 60% NaH in portions. The above mixture was then added via cannula into 19.1 g of 3,5-difluoronitrobenzene in 50 mL DMF at 0° C. The temperature was kept below 10° C. and the mixture was stirred for one hour. To the reaction mixture at 0° C. was added 400 mL saturated NH₄Cl and 400 mL EtOAc. The organic layer was removed and the aqueous layer was extracted with 400 mL EtOAc. The combined organic layers dried over MgSO₄, filtered, and concentrated. The residue was purified by column chromatography over silica with 1 EtOAC:10 hexane as the elute to yield 30 g (S)-2-(tert-butyl-dimethyl-silanyloxymethyl)-(R)-4-hydroxy-pyrrolidine-1-carboxylic acid tert-butyl ester as a yellow solid.

4E. (R)-4-(3-Fluoro-5-nitro-phenoxy)-(S)-2-hydroxymethyl-pyrrolidine-1-carboxylic acid tert-butyl ester. To 30 g of (S)-2-(tert-butyl-dimethyl-silanyloxymethyl)-(R)-4-hydroxy-pyrrolidine-1-carboxylic acid tert-butyl ester in 240 mL MeOH at 0° C. was added 2.6 mL of 1N HCl, dropwise. The reaction mixture was warmed up to room temperature and stirred for an additional 4 hours. After cooling to 0° C., to the reaction mixture was added 5 g of NaHCO₃ and the mixture was extracted with EtOAc. The combined organic layers were dried over MgSO₄, filtered and concentrated to afford 22.7 g of (R)-4-(3-fluoro-5-nitro-phenoxy)-(S)-2-hydroxymethyl-pyrrolidine-1-carboxylic acid tert-butyl ester.

4F. (R)-4-(3-Fluoro-5-nitro-phenoxy)-(S)-2-methoxymethyl-pyrrolidine-1-carboxylic acid tert-butyl ester. To 22.7 g of (R)4-(3-fluoro-5-nitro-phenoxy)-(S)-2-hydroxymethyl-pyrrolidine-1-carboxylic acid tert-butyl ester, 250 mL of anhydrous DMF, and 36.3 g of MeI at 0° C. was added 3.1 g of 60% NaH, in several portions. The reaction mixture was stirred for 2 hours at room temperature. The reaction mixture was concentrated to remove excess MeI then diluted with H₂O. The mixture was diluted with 500 mL of saturated NH₄Cl and extracted 3 times with 500 mL of EtOAc. The combined organic layers were dried and concentrated to yield 23 g of (R)-4-(3-fluoro-5-nitro-phenoxy)-(S)-2-methoxymethyl-pyrrolidine-1-carboxylic acid tert-butyl ester.

4G. (R)-4-(3-amino-5-fluoro-phenoxy)-(S)-2-methoxymethyl-pyrrolidine-1-carboxylic acid tert-butyl ester. A mixture of 23 g of (R)-4-(3-fluoro-5-nitro-phenoxy)-(S)-2-methoxymethyl-pyrrolidine-1-carboxylic acid tert-butyl ester, 100 mL MeOH and 2 g of Pd(OH)₂/C was stirred for 2 hours under a 50 psi hydrogen atmosphere. The mixture was filtered off through a pad of diatomaceous earth and concentrated to give a quantitative yield of (R)-4-(3-amino-5-fluoro-phenoxy)-(S)-2-methoxymethyl-pyrrolidine-1-carboxylic acid tert-butyl ester.

4H. [(S)-4-((R)-3-fluoro-5-nitro-phenoxy)-pyrrolidin-2-yl]-methanol. To 2.0 g of (R)-4-(3-amino-5-fluoro-phenoxy)-(S)-2-methoxymethyl-pyrrolidine-1-carboxylic acid tert-butyl ester in 5 mL of dichloromethane was added 10 mL of TFA. The mixture was stirred for 0.5 hours at room temperature and then solvents were removed in vacuo. The resulting residue was dissolved in 50 mL of EtOAc and washed with aq. NaOH (3×25 mL) and brine (25 mL). The organic layer was then dried over Na₂SO₄, filtered, and concentrated to give 1.29 g (90%) of [(S)-4-((R)-3-fluoro-5-nitro-phenoxy)-pyrrolidin-2-yl]-methanol as a thick yellow oil, which was used directly in the following reaction.

4I. (R)-6-(3-Fluoro-5-nitro-phenoxy)-tetrahydro-pyrrolo[1,(S)-2-c]-oxazol-3-one. To a solution of 1.29 g of [(S)-4-((R)-3-fluoro-5-nitro-phenoxy)-pyrrolidin-2-yl]-methanol in 20 mL of anhydrous dichloromethane was added in one portion 0.82 g of 1,1'-carbonyldiimidazole and the resultant mixture stirred at room temperature under N₂ for 3 hours. The reaction mixture was diluted with 30 mL of dichloromethane and washed with H₂O (2×25 mL) and brine (25 mL). The organic layer was dried over Na₂SO₄, filtered, and concentrated to give 1.82 g of a light yellow solid. Purification over silica gel resulted in 0.825 g of (R)-6-(3-Fluoro-5-nitro-phenoxy)-tetrahydro-pyrrolo[1,(S)-2-c]oxazol-3-one as a white solid.

Example 5

4-{3-fluoro-5-[(R)3-(6-methyl-pyridin-3-yl)-ureido]-phenoxy}-(R)2-methoxymethyl -pyrrolidine-1-carboxylic Acid Methyl Ester HCl Salt 5A. (R)-4-Hydroxy-pyrrolidine-(R)-2-carboxylic acid. 150 g (1.15 mol) of (R)-4-Hydroxy-pyrrolidine-(S)-2-carboxylic acid was dissolved in 2 L of AcOH and treated with 1 L of acetic anhydride. The mixture was heated at 150° C. for 5.5 h. The mixture was concentrated to an oil. This oil was treated with 1 L of 2N HCl and heated to reflux for 1 h. The mixture was concentrated and the solid crystallized from 350 ml of EtOH. Drying in vacuo afforded 95.7 g (60%) of (R)-4-hydroxy-pyrrolidine-(R)-2-carboxylic acid as a white solid.

5B. (R)-4-hydroxy-pyrrolidine-1,(R)-2-dicarboxylic acid 1-tert-butyl ester sodium salt. To a clean, dry 3-neck, 3-L reactor equipped with mechanical stirring, thermocouple, and nitrogen inlet and bubbler was charged 500 mL MeOH. With stirring, to this was added 100.0 g (0.762 mol) of (R)-4-hydroxy-pyrrolidine-(R)-2-carboxylic acid, and 153.64 g NaHCO₃ (1.83 mol; 2.4 eq). The solution was then cooled in an ice bath to 0° C., and 199.60 g (0.914 mol; 1.2 eq) of carbonic anhydride di-tert-butyl ester was added in a single portion. The ice bath was removed, and the reaction was allowed to warm to room temperature overnight. To the mixture was added an additional 0.4 eq. of carbonic anhydride di-tert-butyl ester. After stirring for 5 additional hours 500 mL MTBE (5 vol) was added, and the solution was filtered through a coarse frit, rinsing with a minimal amount of MTBE. The filtrates were then concentrated to afford a clear, light yellow oil which was triturated with 700 mL MTBE (7 vol). The solids were filtered through a coarse frit to afford 173.16 g (90%) of (R)-4-hydroxy-pyrrolidine-1,(R)-2-dicarboxylic acid 1-tert-butyl ester sodium salt as a white solid.

5C. 4-(3-Fluoro-5-nitro-(R)-phenoxy)-pyrrolidine-1,(R)-2-dicarboxylic acid 1-tert-butyl ester. (R)-4-Hydroxy-pyrrolidine-1,(R)-2-dicarboxylic acid 1-tert-butyl ester sodium salt and 1.42 ml (3.2 g, 12.6 mmol) and 12.6 mmol of difluoronitrobenzene in 100 ml of DMF was treated with 757 mg (18.9 mmol) of 60% sodium hydride in mineral oil and the resultant mixture was stirred overnight. The mixture was concentrated to an oil. To this oil was added EtOAc. The EtOAc mixture was washed with sat. citric acid solution/sat. ammonium chloride solution, dried (Na₂SO₄), and concentrated to afford 4.1 g (88%) of thick oil that was used in the next step without further purification.

5D. 4-(3-Fluoro-5-nitro-(R)-phenoxy)-(R)-2-hydroxymethyl-pyrrolidine-1-carboxylic acid tert-butyl ester. 4-(3-Fluoro-5-nitro-(R)-phenoxy)-pyrrolidine-1,(R)-2-dicarboxylic acid 1-tert-butyl ester (4.1 g,11.08 mmol) in 75 ml of THF was treated with 24 ml (24 mmol) of 1M borane-THF and the mixture was heated to reflux for 2 h. The mixture was cooled to 0° C. and MeOH was carefully added. The mixture was concentrated to an oil. To this oil was added EtOAc. The EtOAc mixture was washed with sat. Rochelle's salt solution, dried (Na₂SO₄), and concentrated to an oil. This oil was used in the next step without further purification.

5E. 4-(3-fluoro-5-nitro-(R)-phenoxy)-(R)-2-methoxymethyl-pyrrolidine-1-carboxylic acid tert-butyl ester. 4-(3-Fluoro-5-nitro-(R)-phenoxy)-(R)-2-hydroxymethyl-pyrrolidine-1-carboxylic acid tert-butyl ester in 75 ml DMF was treated with 1.4 ml (22.7 mmol, ~2 eq) of MeI and 908 mg (22.7 mmol, ~2 eq) of 60% sodium hydride in mineral oil. The mixture was stirred 2 h, treated with 10 ml MeOH, stirred for 30 min, concentrated, and purified by flash chromatography (30% EtOAc/Hexanes) to afford 1.81 g (44% over 2 steps) of 4-(3-fluoro-5-nitro-(R)-phenoxy)-(R)-2-methoxymethyl-pyrrolidine-1-carboxylic acid tert-butyl ester as an oil.

5F. 4-(3-Fluoro-5-amino-(R)-phenoxy)-(R)-2-methoxymethyl-pyrrolidine-1-carboxylic acid tert-butyl ester. 4-(3-Fluoro-5-nitro-(R)-phenoxy)-(R)-2-methoxymethyl-pyrrolidine-1-carboxylic acid tert-butyl ester (1.81 g, 4.89 mmol) in 50 ml of MeOH was treated with a catalytic amount of 20% Pd(OH)₂ under 60 psi of hydrogen overnight. The mixture was filtered (Celite) and evaporated affording 1.56 g (97%) of 4-(3-fluoro-5-amino-(R)-phenoxy)-(R)-2-methoxymethyl-pyrrolidine-1-carboxylic acid tert-butyl ester as an oil.

5G. 4-{3-Fluoro-5-[(R)-3-(6-methyl-pyridin-3-yl)-ureido]-phenoxy}-(R)-2-methoxymethyl-pyrrolidine-1-carboxylic acid tert-butyl ester. 4-(3-Fluoro-5-amino-(R)-phenoxy)-(R)-2-methoxymethyl-pyrrolidine-1-carboxylic acid tert-butyl ester (1.56 g, 4.59 mmol) of amine in 50 ml of THF were treated with 677 mg (5.05 mmol) of 2-methylpyridyl-5-isocyanate and the mixture was stirred at 50° C. for 1 h. The mixture was concentrated to a solid. This solid was used in the next step without purification.

5H. 4-{3-Fluoro-5-[(R)-3-(6-methyl-pyridin-3-yl)-ureido]-phenoxy}-(R)-2-methoxymethyl-pyrrolidine-1-carboxylic acid methyl ester HCl salt. 4-{3-Fluoro-5-[(R)-3-(6-methyl-pyridin-3-yl)-ureido]-phenoxy}-(R)-2-methoxymethyl-pyrrolidine-1-carboxylic acid tert-butyl ester in 10 ml of MeOH was treated with 5 ml of 4N HCl in Dioxane. The mixture was stirred at 50 deg for 15 min and concentrated to an oil. This oil was treated with 30 ml DCM, 4.52 ml (32.5 mmol) of TEA, and 597 µL of methylchloroformate and the mixture was stirred for 1 h at rt. The mixture was concentrated and purified by flash chromatography (6% MeOH/DCM) to afford 1.07 g (54% over 2 steps) of a white solid. A portion of the solid was dissolved in EtOH, treated with 1.2 eq of 4N HCl in dioxane, concentrated, treated with a few drops of EtOH, heated to 80° C., and treated with the minimal amount of EtOH needed to dissolve the solid. Upon cooling, the white solid of 4-{3-fluoro-5-[(R)-3-(6-methyl-pyridin-3-yl)-ureido]-phenoxy}-(R)-2-methoxymethyl -pyrrolidine-1-carboxylic acid methyl ester HCl salt was isolated by filtration (mp=205° C.).

Example 6

Other Compounds of Formula I

Similarly, by following the procedures illustrated in Examples 1 to 4 and with respect to Reaction Schemes 1 to 5, the following compounds corresponding to Formula 6 were obtained:

Formula 6

| | X | R¹·³ | R² |
|---|---|---|---|
| 6.01 | O | Cyano | Methoxyphenyl |
| 6.02 | O | 1H-Imidazolyl- | Methoxyphenyl |
| 6.03 | O | Ethoxycarbonyl | Methoxyphenyl |
| 6.04 | O | 5-Oxo-2,5-dihydro-[1,2,4]oxadiazole-3-yl | Methoxyphenyl |
| 6.05 | O | Ethoxycarbonyl | Pyridinyl |
| 6.06 | O | Ethoxycarbonyl | Isoxazol-3-yl |
| 6.07 | O | Methyl | Pyridinyl |
| 6.08 | —SO— | Nitro | Methoxyphenyl |
| 6.09 | O | Formyl | Methoxyphenyl |
| 6.10 | O | Fluoro | Fluorophenyl |
| 6.11 | O | Pyridinyl | Fluorophenyl |
| 6.12 | O | Ethynyl | Fluorophenyl |
| 6.13 | O | Oxazol-2-yl | Fluorophenyl |
| 6.14 | O | Thiazol-2-yl | Fluorophenyl |
| 6.15 | O | Trifluoromethyl | Fluorophenyl |
| 6.16 | O | Cyano | Fluorophenyl |

-continued

Formula 6

| X | R<sup>1.3</sup> | R<sup>2</sup> |
|---|---|---|
| 6.17 | O | Pyrazin-2-yl | Fluorophenyl |
| 6.18 | O | Ethoxycarbonyl | Fluorophenyl |
| 6.19 | O | NO₂ | Fluorophenyl- |
| 6.20 | O | NO₂ | Chlorophenyl- |
| 6.21 | O | NO₂ | Difluorophenyl- |
| 6.22 | S | NO₂ | Methoxyphenyl- |
| 6.23 | —SO₂— | NO₂ | Methoxyphenyl- |
| 6.24 | —OCH₂— | NO₂ | Methoxyphenyl- |
| 6.25 | O | NO₂ | Methoxyphenyl |
| 6.26 | O | NO₂ | Cyanophenyl |
| 6.27 | O | NO₂ | Phenyl |

Example 7

Other Compounds of Formula I

Similarly, by following the procedures illustrated in Examples 1 to 4 and with respect to Reaction Schemes 1 to 5, the following compounds were obtained:

Formula I

| | R¹ | R² |
|---|---|---|
| 7.01 | Pyridinyl | 3-Nitro-5-(4-fluorophenoxy)-phenyl |
| 7.02 | Pyridinyl | 3-Nitro-5-phenoxy-phenyl |
| 7.03 | 3-Fluoro-5-hydroxyphenyl | 2-Methyl-3-chlorophenyl |
| 7.04 | 3,5-Dichlorophenyl | 3-Hydroxyphenyl |
| 7.05 | Naphthyl- | 3-Acetylaminophenyl- |
| 7.06 | 3-Hydroxyphenyl | 2,5-Difluorophenyl |
| 7.07 | 2-Methoxy-5-chlorophenyl | 3-Hydroxyphenyl |
| 7.08 | 3-Hydroxyphenyl | 2-Chloro-6-methylphenyl |
| 7.09 | 2-Methyl-3-chlorophenyl | 3-Hydroxyphenyl |
| 7.10 | 3-Chlorophenyl | 3-Hydroxyphenyl |
| 7.11 | 3-Hydroxyphenyl | 2,3-Dichlorophenyl |
| 7.12 | 3-Hydroxyphenyl | 2-Methyl-5-fluorophenyl |
| 7.13 | 3-Hydroxyphenyl | 2,3-Dimethylphenyl |
| 7.14 | 3-Hydroxyphenyl | 2-Methyl-5-cyanophenyl |
| 7.15 | 3-Hydroxyphenyl | 3-Trifluoromethyl phenyl |
| 7.16 | 3-Hydroxyphenyl | 2-methyl-5-chlorophenyl |
| 7.17 | 3-Hydroxyphenyl | 3-Chloro-4-methylphenyl |
| 7.18 | 3-Hydroxyphenyl | 4-Carbamoylphenyl |
| 7.19 | 3-Hydroxy-5-fluoro-phenyl | 2-Methyl-3-chlorophenyl |
| 7.20 | 3-Hydroxyphenyl | 2-Trifluoromethoxyphenyl |
| 7.21 | 3-Hydroxyphenyl | Naphthyl |
| 7.22 | 3-Hydroxyphenyl | 3,5-Bis-Trifluoromethylphenyl |
| 7.23 | 3-Hydroxyphenyl | 2-Fluoro-3-chlorophenyl |
| 7.24 | 3-Hydroxyphenyl | 3-Isopropoxyphenyl |
| 7.25 | 3-Hydroxyphenyl | 3-isopropylphenyl |
| 7.26 | 3-Hydroxyphenyl | 3-nitrophenyl |
| 7.27 | 3-Hydroxyphenyl | 3-bromophenyl |
| 7.28 | 3-Hydroxyphenyl | 3,5-dichlorophenyl |
| 7.29 | 3-Hydroxyphenyl | 2,-methyl-3-bromophenyl |
| 7.30 | 3-Hydroxyphenyl | 3-fluorophenyl |
| 7.31 | 3-Hydroxyphenyl | 3-iodophenyl |

-continued

Formula I

| | R¹ | R² |
|---|---|---|
| 7.32 | 3-Hydroxyphenyl | 2-methyl-3-cyanophenyl |
| 7.33 | Naphthyl | 3-methylsulfonylaminophenyl |
| 7.34 | 2-methyl-3-chloro | 3-methylsulfonylaminophenyl |
| 7.35 | 3-Hydroxyphenyl | 2-cyano-3-chlorophenyl |
| 7.36 | 3-Hydroxyphenyl | 2-cyano-3-methylphenyl |
| 7.37 | 3-Hydroxyphenyl | 2-cyano-3-fluorophenyl |
| 7.38 | 3-Hydroxyphenyl | 2-chloro-5-methoxyphenyl |
| 7.39 | 3-Hydroxyphenyl | 3-nitro-naphth-1-yl |
| 7.40 | 3-Hydroxyphenyl | 5,6,7,8-tetrahydronaphth-1-yl |
| 7.41 | 3-Hydroxyphenyl | Isoquinoline-5-yl |
| 7.42 | 4-Carbamoylphenyl | 2-methyl-3-chlorophenyl |
| 7.43 | 3-Hydroxyphenyl | 2-chloro-3-methylphenyl |
| 7.44 | 6-methyl-pyridin-3-yl | 3-Fluoro-5-(6-oxo-piperidin-3-yloxy)-phenyl |
| 7.45 | 6-methyl-pyridin-3-yl | 3-Fluoro-5-(2-oxo-piperidin-3-yloxy)-phenyl |
| 7.46 | 6-methyl-pyridin-3-yl | 3-Fluoro-5-[1-(morpholine-4-carbonyl)-piperidin-3-yloxy]-phenyl |
| 7.47 | pyridin-3-yl | 3-Fluoro-5-(6-oxo-piperidin-3-yloxy)-phenyl |
| 7.48 | Methoxyphenyl | 3-(Ethynyl)-5-(Pyridin-3-yl)oxy-phenyl |

Example 8

Other Compounds of Formula I

Similarly, by following the procedures illustrated in Examples 1 to 4 and with respect to Reaction Schemes 1 to 5, the following compounds corresponding to Formula 8 were obtained:

Formula 8

| | R<sup>1.1</sup> |
|---|---|
| 8.1 | (3-acetylpiperidinyl) |
| 8.2 | (pyridin-3-ylmethyl) |

-continued
Formula 8
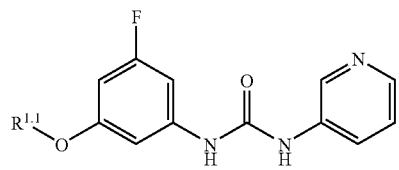
| | $R^{1.1}$ |
|---|---|
| 8.3 | 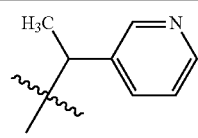 |
| 8.4 | 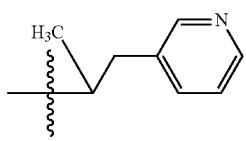 |
| 8.5 | 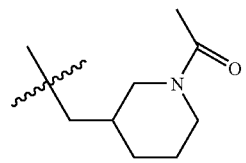 |
| 8.6 | 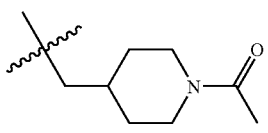 |
| 8.7 | 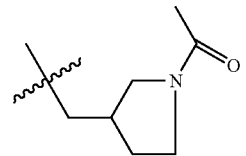 |
| 8.8 | 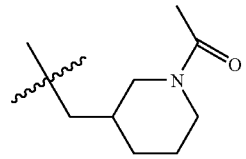 |
| 8.9 | 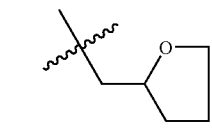 |
| 8.10 | 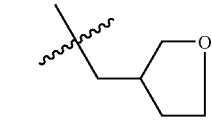 |
| 8.11 | 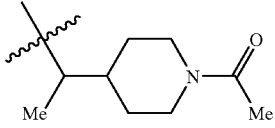 |
-continued
Formula 8
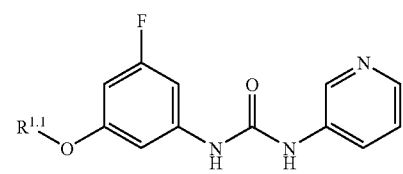
| | $R^{1.1}$ |
|---|---|
| 8.12 | 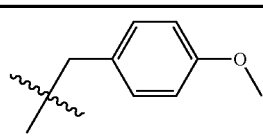 |
| 8.13 | 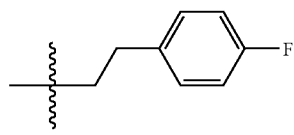 |
| 8.14 | 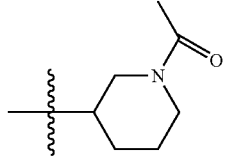 |
| 8.15 | 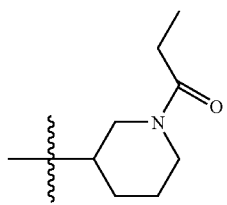 |
| 8.16 | 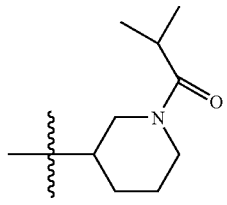 |
| 8.17 | 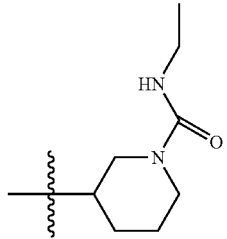 |
| 8.18 | 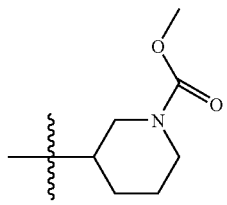 |

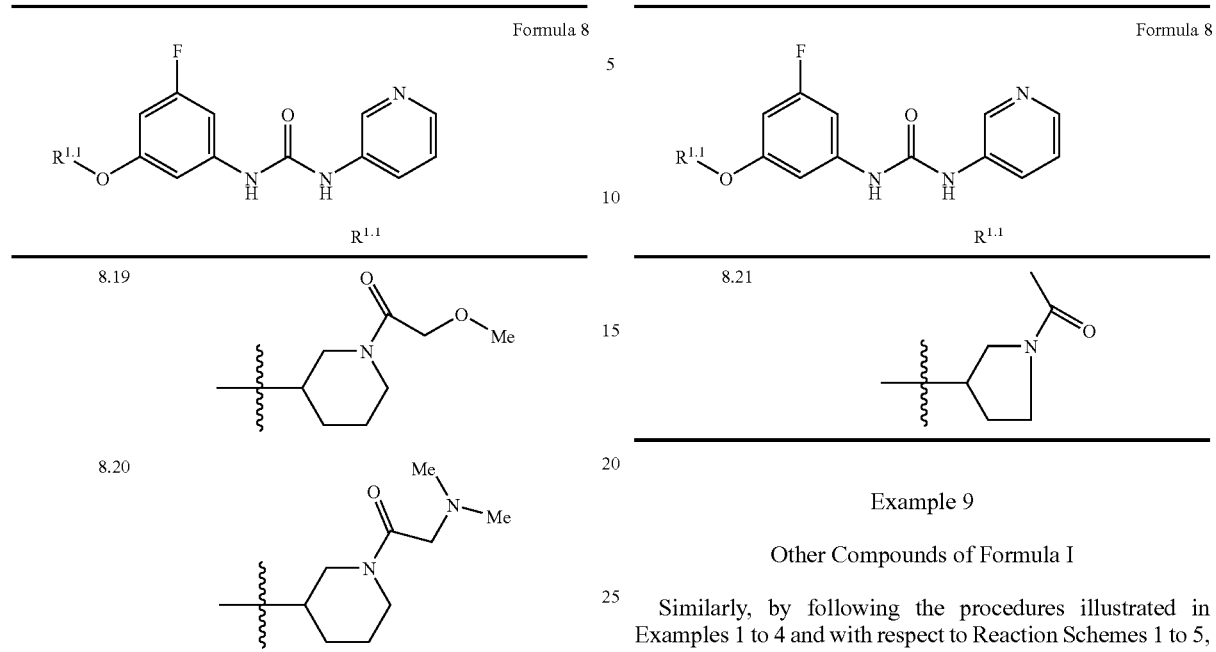

Example 9

Other Compounds of Formula I

Similarly, by following the procedures illustrated in Examples 1 to 4 and with respect to Reaction Schemes 1 to 5, the following compounds corresponding to Formula 9 were obtained:

| | $R^1$ | $R^{2.1}$ |
|---|---|---|
| 9.001 | 2-chlorophenyl- | 3-methoxyphenyl- |
| 9.002 | 2-chlorophenyl- | 3-hydroxy-4-sulfamoyl-phenyl- |
| 9.003 | 6-methyl-pyridin-3-yl- | 2-ethyl-phenyl- |
| 9.004 | 6-methyl-pyridin-3-yl- | 2,3-dimethyl-phenyl- |
| 9.005 | 6-methyl-pyridin-3-yl- | 2-methyl-3-methoxy-phenyl- |
| 9.006 | 6-methyl-pyridin-3-yl- | 3-methyl-2-methoxy-phenyl- |
| 9.007 | 6-methyl-pyridin-3-yl- | 3-methyl-2-chloro-phenyl- |
| 9.008 | 6-methyl-pyridin-3-yl- | 2-chloro-6-methoxy-phenyl- |
| 9.009 | 3-hydroxyphenyl- | phenyl |
| 9.010 | 3-hydroxyphenyl- | 2-chlorophenyl- |
| 9.011 | 3-hydroxyphenyl- | 2-fluorophenyl- |
| 9.012 | 3-hydroxyphenyl- | 2-methoxyphenyl- |
| 9.013 | 3-hydroxyphenyl- | 3-fluorophenyl- |
| 9.014 | 3-hydroxyphenyl- | 4-fluorophenyl- |
| 9.015 | 3-hydroxyphenyl- | 4-methylphenyl- |
| 9.016 | Pyridinyl- | 2-chlorophenyl- |
| 9.017 | 6-methyl-pyridin-3-yl- | 2-chlorophenyl- |
| 9.018 | 3-hydroxy-4-methyl-phenyl- | 2-chlorophenyl- |
| 9.019 | Phenyl | 2-chlorophenyl- |
| 9.020 | 3-fluorophenyl- | 2-chlorophenyl- |
| 9.021 | 3-Aminosulfonylphenyl- | 2-chlorophenyl- |
| 9.022 | 5-Hydroxy-pyridin-3-yl | 2-chlorophenyl- |
| 9.023 | 6-trifluoromethyl-pyridin-3-yl- | 2-chlorophenyl- |
| 9.024 | 3-acetoxyphenyl- | 3-chlorophenyl- |
| 9.025 | 3-acetoxyphenyl- | 3-methoxyphenyl- |
| 9.026 | 3-acetoxyphenyl- | 4-methoxyphenyl- |
| 9.027 | 3-hydroxyphenyl- | 3-methoxyphenyl- |
| 9.028 | 3-hydroxyphenyl- | 4-methoxyphenyl- |
| 9.029 | 3-acetoxyphenyl- | 2,6-dichlorophenyl- |
| 9.030 | 3-hydroxyphenyl- | 2,6-dichlorophenyl- |
| 9.031 | 3-acetoxyphenyl- | 4-chlorophenyl- |
| 9.032 | 3-hydroxyphenyl- | 4-chlorophenyl- |
| 9.033 | 3-acetoxyphenyl- | 2-methylphenyl- |
| 9.034 | 3-hydroxyphenyl- | 2-methylphenyl- |

-continued

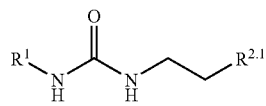

Formula 9

| | R¹ | R²·¹ |
|---|---|---|
| 9.035 | 3-acetoxyphenyl- | 2,3-dimethoxyphenyl- |
| 9.036 | 3-hydroxyphenyl- | 2,3-dimethoxyphenyl- |
| 9.037 | Pyridin-4-yl | 2-chlorophenyl- |
| 9.038 | 6-ethyl-pyridin-3-yl | 2-chlorophenyl- |
| 9.039 | 6-methyl-pyridin-3-yl | 2-methylphenyl- |
| 9.040 | 6-methyl-pyridin-3-yl | 2,6-dichlorophenyl- |
| 9.041 | 6-methyl-pyridin-3-y | 2,3-dimethoxyphenyl- |
| 9.042 | 3-hydroxy-4-chlorophenyl- | 2-chlorophenyl- |
| 9.043 | 6-methoxy-pyridin-3-yl | 2-chlorophenyl- |
| 9.044 | 6-carbamoyl-pyridin-3-yl | 2-chlorophenyl- |
| 9.045 | 6-methoxy-pyridin-3-yl | 2-methoxyphenyl- |
| 9.046 | 3-acetoxyphenyl- | pyridin-4-yl |
| 9.047 | 3-hydroxyphenyl- | pyridin-4-yl |
| 9.048 | 4-cyanophenyl- | 2-chlorophenyl- |
| 9.049 | 4-carbamoylphenyl- | 2-chlorophenyl- |
| 9.050 | 6-methyl-pyridin-3-yl | 2,4-dimethylphenyl- |
| 9.051 | 6-methyl-pyridin-3-yl | 2,5-dimethylphenyl- |
| 9.052 | 6-methyl-pyridin-3-yl | 2,6-dimethylphenyl- |
| 9.053 | 6-methyl-pyridin-3-yl | 2,3-dichlorophenyl- |
| 9.054 | 6-methyl-pyridin-3-yl | 2,4-dichlorophenyl- |
| 9.055 | 6-methyl-pyridin-3-yl | 2,5-dichlorophenyl- |
| 9.056 | 3-hydroxy-phenyl- | 2,4-dimethylphenyl- |
| 9.057 | 3-acetoxyphenyl- | 2,5-dimethylphenyl- |
| 9.058 | 3-hydroxy-phenyl- | 2,5-dimethylphenyl- |
| 9.059 | 3-acetoxyphenyl- | 2,6-dimethylphenyl- |
| 9.060 | 3-hydroxy-phenyl- | 2,6-dimethylphenyl- |
| 9.061 | 3-acetoxyphenyl- | 2,3-dichlorophenyl- |
| 9.062 | 3-hydroxy-phenyl- | 2,3-dichlorophenyl- |
| 9.063 | 3-acetoxyphenyl- | 2,4-dichlorophenyl- |
| 9.064 | 3-hydroxy-phenyl- | 2,4-dichlorophenyl- |
| 9.065 | 3-acetoxyphenyl- | 2,5-dichlorophenyl- |
| 9.066 | 3-hydroxy-phenyl- | 2,5-dichlorophenyl- |
| 9.067 | 3-hydroxy-4-chloro-phenyl- | 2,6-dichlorophenyl- |
| 9.068 | 6-methyl-pyridin-3-yl | 2-chloro-6-fluoro-phenyl- |
| 9.069 | 6-methyl-pyridin-3-yl | 2,6-difluorophenyl- |
| 9.070 | 3-acetoxyphenyl- | 2-chloro-6-fluoro-phenyl- |
| 9.071 | 3-hydroxy-phenyl- | 2-chloro-6-fluoro-phenyl- |
| 9.072 | 3-acetoxyphenyl- | 2,6-difluorophenyl- |
| 9.073 | 3-hydroxy-phenyl- | 2,6-difluorophenyl- |
| 9.074 | 6-methyl-pyridin-3-yl | 2-ethoxyphenyl- |
| 9.075 | 3-acetoxyphenyl- | 2-ethoxyphenyl- |
| 9.076 | 3-hydroxy-phenyl- | 2-ethoxyphenyl- |
| 9.077 | 6-cyano-pyridin-3-yl | 2-chlorophenyl- |
| 9.078 | 6-methoxycarbonyl-pyridin-3-yl | 2-chlorophenyl- |
| 9.079 | 3-hydroxy-phenyl- | 2-isopropoxyphenyl- |
| 9.080 | 6-methyl-pyridin-3-yl | 2-trifluoromethylphenyl- |
| 9.081 | 3-acetoxyphenyl- | 2-trifluoromethylphenyl- |
| 9.082 | 3-acetoxyphenyl- | 2-trifluoromethoxyphenyl- |
| 9.083 | 3-hydroxy-phenyl- | 2-trifluoromethylphenyl- |
| 9.084 | 3-hydroxy-phenyl- | 2-trifluoromethoxyphenyl- |
| 9.085 | 6-methyl-pyridin-3-yl | 2-methoxyphenyl- |
| 9.086 | 6-methyl-pyridin-3-yl | 2-trifluoromethoxyphenyl- |
| 9.087 | 3-hydroxymethyl-4-fluorophenyl- | 2-chlorophenyl- |
| 9.088 | 3-hydroxy-4-fluorophenyl- | 2-chlorophenyl- |
| 9.089 | 6-acetyl-pyridin-3-yl | 2-chlorophenyl- |
| 9.090 | 6-(1-hydroxyethyl)-pyridin-3-yl | 2-chlorophenyl- |
| 9.091 | 3-acetoxyphenyl- | 3,4-dichlorophenyl- |
| 9.092 | 3-hydroxy-phenyl- | 3,4-dichlorophenyl- |
| 9.093 | 3-acetoxyphenyl- | 2,6-dimethoxyphenyl- |
| 9.094 | 3-hydroxy-phenyl- | 2,6-dimethoxyphenyl- |
| 9.095 | 3-acetoxyphenyl- | 2,3-methylenedioxyphenyl- |
| 9.096 | 3-hydroxy-phenyl- | 2,3-methylenedioxyphenyl- |
| 9.097 | 3-acetoxyphenyl- | 2-chloro-6-methoxyphenyl- |
| 9.098 | 3-hydroxy-phenyl- | 2-chloro-6-methoxyphenyl- |
| 9.099 | 3-acetoxyphenyl- | 2-methyl-3-methoxyphenyl- |

-continued

Formula 9

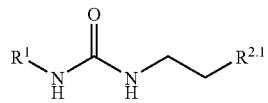

| | $R^1$ | $R^{2.1}$ |
|---|---|---|
| 9.100 | 3-hydroxy-phenyl- | 2-methyl-3-methoxyphenyl- |
| 9.101 | 3-hydroxy-6-methylphenyl- | 2-chlorophenyl- |
| 9.102 | 3-acetoxyphenyl- | 2-bromophenyl- |
| 9.103 | 3-hydroxy-phenyl- | 3,5-dimethoxyphenyl- |
| 9.104 | 3-hydroxy-phenyl- | 2-bromophenyl- |
| 9.105 | 5-acetamido-pyridin-3-yl | 2-chlorophenyl- |
| 9.106 | 3-hydroxy-phenyl- | 2-methyl-3-chlorophenyl- |
| 9.107 | 3-hydroxy-phenyl- | 2-methoxy-3-methylphenyl- |
| 9.108 | 3-hydroxy-phenyl- | 2-cyanophenyl- |
| 9.109 | 3-acetoxyphenyl- | 2,5-dimethoxyphenyl- |
| 9.110 | 3-hydroxy-phenyl- | 2,5-dimethoxyphenyl- |
| 9.111 | 3-hydroxy-phenyl- | 2-phenoxyphenyl- |
| 9.112 | 3-fluoro-5-hydroxyphenyl- | 2-chlorophenyl- |
| 9.113 | 6-methyl-pyridin-3-yl | 2,5-dimethoxyphenyl- |
| 9.114 | 6-methyl-pyridin-3-yl | 2-phenoxyphenyl- |
| 9.115 | 3-hydroxy-4-fluorophenyl- | 2-chloro-6-methoxyphenyl- |
| 9.116 | 3-hydroxy-4-fluorophenyl- | 2-methyl-3-chlorophenyl- |
| 9.117 | 3-hydroxy-4-fluorophenyl- | 2-methoxy-3-methylphenyl- |
| 9.118 | 3-hydroxy-4-fluorophenyl- | 2-methyl-3-methoxyphenyl- |
| 9.119 | 3-hydroxy-4-fluorophenyl- | 2,3-dimethylphenyl- |
| 9.120 | 3-hydroxy-4-fluorophenyl- | 2,6-dimethylphenyl- |
| 9.121 | 2-fluoro-3-hydroxyphenyl- | 2-chlorophenyl- |
| 9.122 | 6-hydroxymethyl-pyridin-3-yl | 2-chlorophenyl- |
| 9.123 | 6-methyl-pyridin-3-yl | 2-chloro-6-methoxyphenyl- |
| 9.124 | 6-methyl-pyridin-3-yl | 2-methyl-3-chlorophenyl- |
| 9.125 | 6-methyl-pyridin-3-yl | 2-methoxy-3-methylphenyl- |
| 9.126 | 6-methyl-pyridin-3-yl | 3-methoxy-2-methylphenyl- |
| 9.127 | 6-methyl-pyridin-3-yl | 2,3-dimethylphenyl- |
| 9.128 | 6-methyl-pyridin-3-yl | 2-ethylphenyl- |
| 9.129 | 3-hydroxy-4-aminosulfonylphenyl- | 2-chlorophenyl- |
| 9.130 | 3-methoxyphenyl- | 2-chlorophenyl- |
| 9.131 | 6-methyl-pyridin-3-yl | 2-benzyloxyphenyl- |
| 9.132 | 6-methyl-pyridin-3-yl | 2-(trifluoromethylsulfanyl)phenyl- |
| 9.133 | 3-acetoxyphenyl- | 2-benzyloxyphenyl- |
| 9.134 | 3-acetoxyphenyl- | 2-(trifluoromethylsulfanyl)phenyl- |
| 9.135 | 3-hydroxy-phenyl- | 2-benzyloxyphenyl- |
| 9.136 | 3-hydroxy-phenyl- | 2-(trifluoromethylsulfanyl)phenyl- |
| 9.137 | 3-hydroxy-4-acetyl-phenyl- | 2-chlorophenyl- |
| 9.138 | 3-hydroxy-phenyl- | 2-ethylphenyl- |
| 9.139 | 3-hydroxy-phenyl- | 2-cyclopropylmethoxy-phenyl- |
| 9.140 | 3-acetoxyphenyl- | 2-cyclopropylmethoxy-phenyl- |
| 9.141 | 6-methyl-pyridin-3-yl | 2-cyclopropylmethoxy-phenyl- |
| 9.142 | 3-hydroxy-4-carbamoyl-phenyl- | 2-chlorophenyl- |
| 9.143 | 3-hydroxy-4-methylcarbamoyl-phenyl | 2-chlorophenyl- |
| 9.144 | 3-hydroxy-4-dimethylcarbamoyl-phenyl | 2-chlorophenyl- |
| 9.145 | 3-hydroxy-phenyl- | 2-(2-methylpropoxy)-phenyl- |
| 9.146 | 3-acetoxyphenyl- | 2-(2-methylpropoxy)-phenyl- |
| 9.147 | 6-methyl-pyridin-3-yl | 2-(2-methylpropoxy)-phenyl- |
| 9.148 | 3-hydroxy-phenyl- | 2-(2,2,2-trifluoroethoxy)-phenyl- |
| 9.149 | 3-acetoxyphenyl- | 2-(2,2,2-trifluoroethoxy)-phenyl- |
| 9.150 | 6-methyl-pyridin-3-yl | 2-(2,2,2-trifluoroethoxy)-phenyl- |
| 9.151 | 3-hydroxy-4-methoxycarbonyl-phenyl- | 2-chlorophenyl- |
| 9.152 | 6-(2-hydroxyethyl)-pyridin-3-yl | 2-chlorophenyl- |
| 9.153 | 6-(Methoxycarbonylmethyl)-pyridin-3-yl | 2-chlorophenyl- |
| 9.154 | 6-methyl-pyridin-3-yl | 1H-Indol-3-yl |
| 9.155 | 1H-indazol-6-yl | 2-chlorophenyl- |
| 9.156 | 3-acetoxyphenyl- | 1H-Indol-3-yl |
| 9.157 | 3-hydroxy-phenyl- | 1H-Indol-3-yl |
| 9.158 | 3-hydroxy-phenyl- | 2-bromophenyl- |
| 9.159 | Quinolin-3-yl | 2-chlorophenyl- |
| 9.160 | 1H-benzoimidazol-2-yl | 2-chlorophenyl- |
| 9.161 | 2-methyl-pyridine 1-oxide-5-yl | 2-chlorophenyl- |
| 9.162 | 6-(5-Oxo-4,5-dihydro-[1,2,4]oxadiazol-3-yl)-pyridin-3-yl | 2-chlorophenyl- |
| 9.163 | 5-Methyl-[1,2,4]oxadiazole-3-yl | 2-chlorophenyl- |

Example 10

Other Compounds of Formula I

Similarly, by following the procedures illustrated in Examples 1 to 4 and with respect to Reaction Schemes 1 to 5, the following compounds corresponding to Formula 10 were obtained:

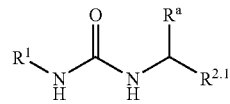

Formula 10

| | R¹ | Rᵃ | R²·¹ |
|---|---|---|---|
| 10.00 | 2-fluorophenyl- | H | 3-hydroxyphenyl- |
| 10.01 | 3-hydroxyphenyl- | H | 2-methoxy-phenyl- |
| 10.02 | 3-hydroxyphenyl- | H | 2-methyl-phenyl- |
| 10.03 | 3-hydroxyphenyl- | H | 3-chloro-phenyl- |
| 10.04 | 3-hydroxy-phenyl- | H | 3-methoxy-phenyl- |
| 10.05 | 3-hydroxy-phenyl- | H | 3-methyl-phenyl- |
| 10.06 | 3-hydroxyphenyl- | H | 4-hydroxyphenyl- |
| 10.07 | 3-hydroxyphenyl- | H | 4-fluorophenyl- |
| 10.08 | 3-hydroxyphenyl- | H | 3-methoxy-phenyl- |
| 10.09 | 3-hydroxyphenyl | H | 4-methylphenyl- |
| 10.10 | 3-hydroxyphenyl | H | 2-chlorophenyl- |
| 10.11 | 3-hydroxyphenyl | Methyl | Phenyl |
| 10.12 | 3-hydroxyphenyl | Methyl | 4-chlorophenyl |
| 10.13 | 3-hydroxyphenyl | Methyl | 4-fluorophenyl |
| 10.14 | 3-hydroxyphenyl | Methyl | 4-methoxyphenyl |
| 10.15 | 3-hydroxyphenyl | H | Phenyl |
| 10.16 | 3-hydroxyphenyl | H | 4-chlorophenyl |
| 10.17 | 3-hydroxyphenyl | H | 4-methoxyphenyl |
| 10.18 | 3-hydroxyphenyl | H | 4-methylphenyl |
| 10.19 | 3-hydroxyphenyl | Methyl | 3-methoxyphenyl- |
| 10.20 | 3-hydroxyphenyl | H | 2-hydroxyphenyl- |
| 10.21 | 3-hydroxyphenyl | H | 3-hydroxyphenyl |
| 10.22 | 3-hydroxyphenyl | H | 4-hydroxyphenyl |
| 10.23 | 3-Acetoxyphenyl- | Methyl | 2-chlorobenzyl- |
| 10.24 | 3-hydroxyphenyl | Methyl | 2-chlorobenzyl- |
| 10.25 | 3-Acetoxyphenyl- | H | 2-chlorobenzyl- |
| 10.26 | 3-hydroxyphenyl | H | 2-chlorobenzyl- |
| 10.27 | 6-methyl-pyridin-3-yl | Methyl | 2-chlorobenzyl- |
| 10.28 | Cyclohexyl- | Methyl | 3-hydroxyphenyl |
| 10.29 | Cyclohexyl- | H | 3-hydroxyphenyl |
| 10.30 | Tetrahydro-pyranyl- | H | 3-hydroxyphenyl |
| 10.31 | pyridin-3-yl | Methyl | 3-(1-Acetyl-piperidin-3-yloxy)-5-fluoro-phenyl |
| 10.32 | 6-methyl-pyridin-3-yl | Methyl | 3-(1-Acetyl-piperidin-3-yloxy)-5-fluoro-phenyl |
| 10.33 | 6-ethyl-pyridin-3-yl | H | 3-(1-Acetyl-piperidin-3-yloxy)-5-fluoro-phenyl |
| 10.34 | 6-methyl-pyridin-3-yl | H | 3-Fluoro-5-(1-formyl-piperidin-3-yloxy)-phenyl- |
| 10.35 | 6-Ethynyl-pyridin-3-yl | H | 3-(1-Acetyl-piperidin-3-yloxy)-5-fluoro-phenyl |
| 10.36 | 6-methyl- pyridin-3-yl | H | 3-(1-Acetyl-piperidin-3-yloxy)-5-fluoro-phenyl |
| 10.37 | 3-(pyridin-2-yl)-5-(pyridin-3-yloxy)-phenyl | H | Pyridin-3-yl |
| 10.38 | 3-Fluoro-5-(pyridin-3-yloxy)-phenyl | H | Imidazol-1-yl |
| 10.39 | 3-(pyridin-2-yl)-5-(pyridin-3-yloxy)-phenyl | H | 4-Methoxyphenyl |
| 10.40 | 3-Fluoro-5-(pyridin-3-yloxy)-phenyl | H | 1-Methyl-1H-pyrazole-4-yl |

Example 11

Other Compounds of Formula I

Similarly, by following the procedures illustrated in Examples 1 to 4 and with respect to Reaction Schemes 1 to 5, the following compounds corresponding to Formula III were obtained:

Formula III

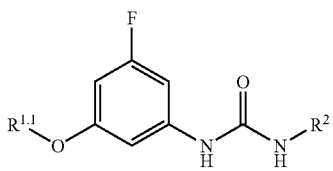

| | R¹·¹ | R² |
|---|---|---|
| 11.1 | (3-acetylpiperidin-1-yl) | (6-methylpyridin-3-yl) |

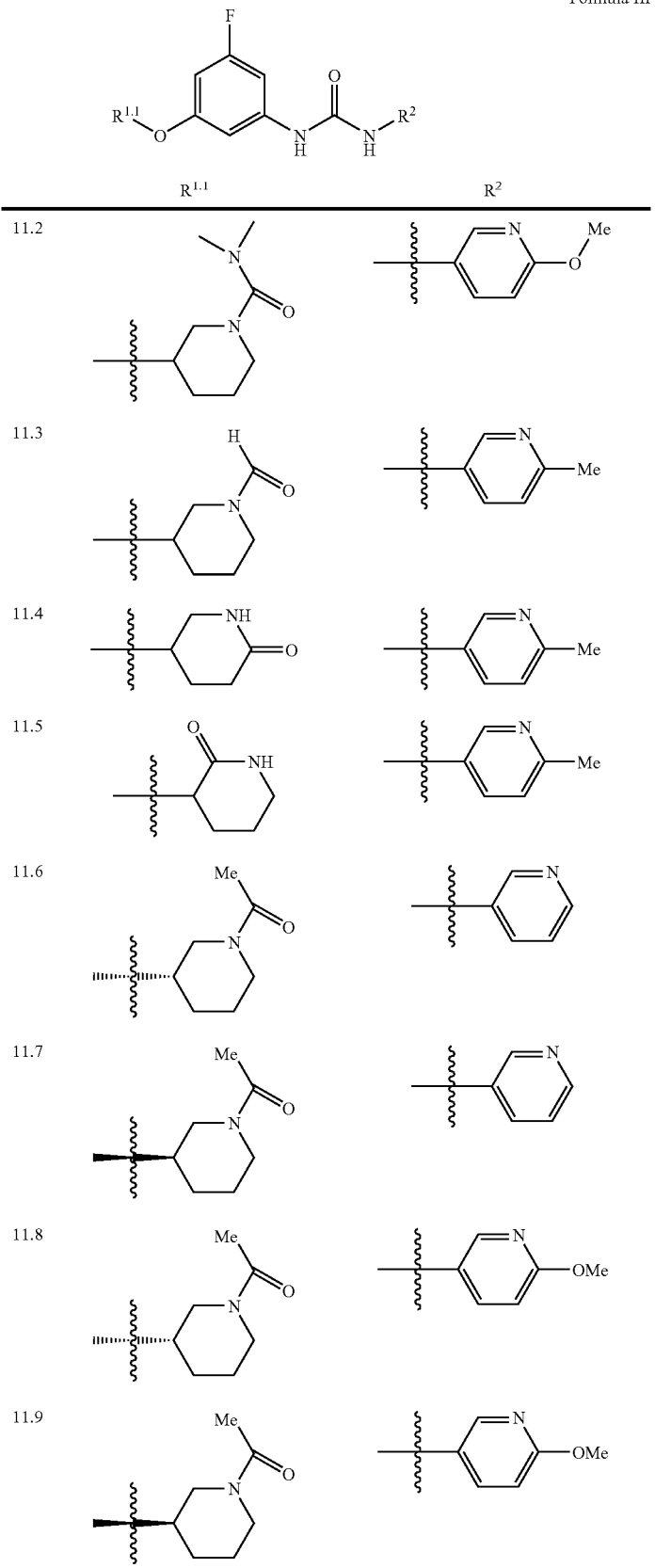

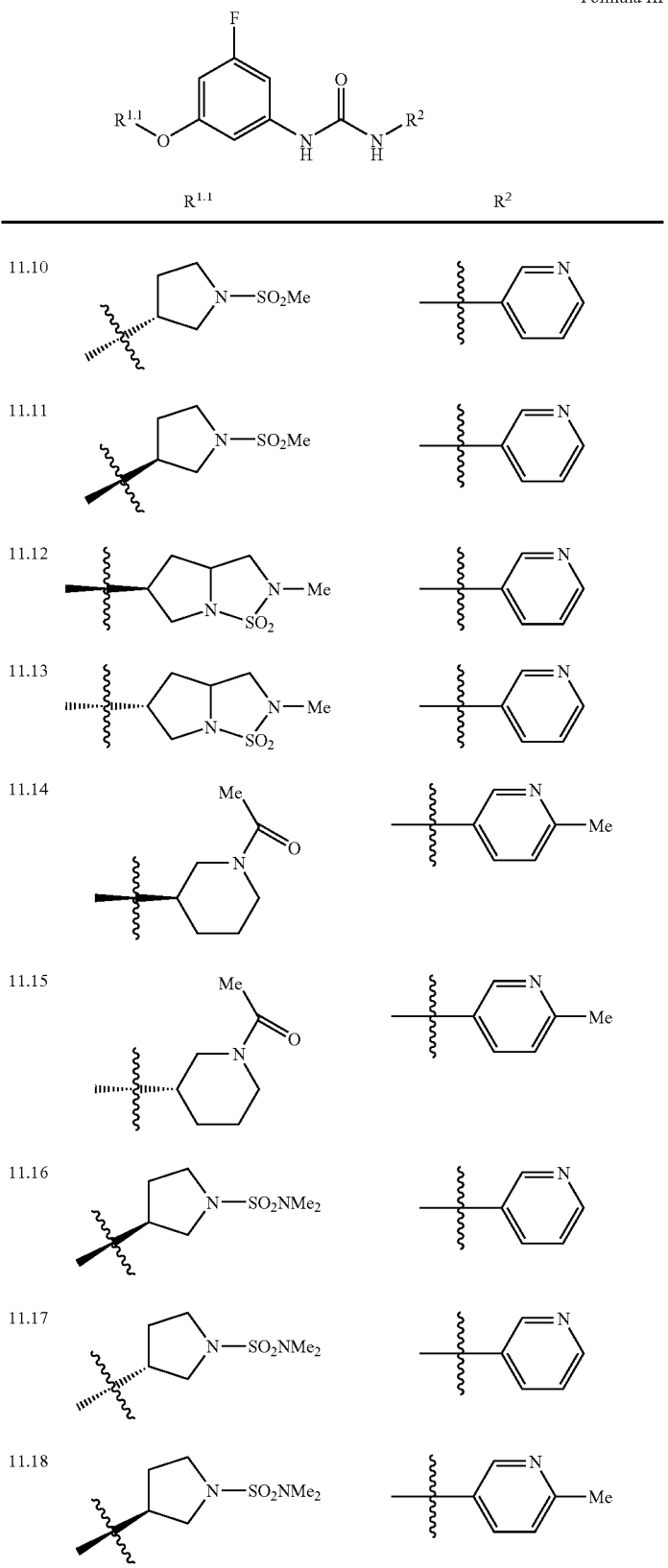

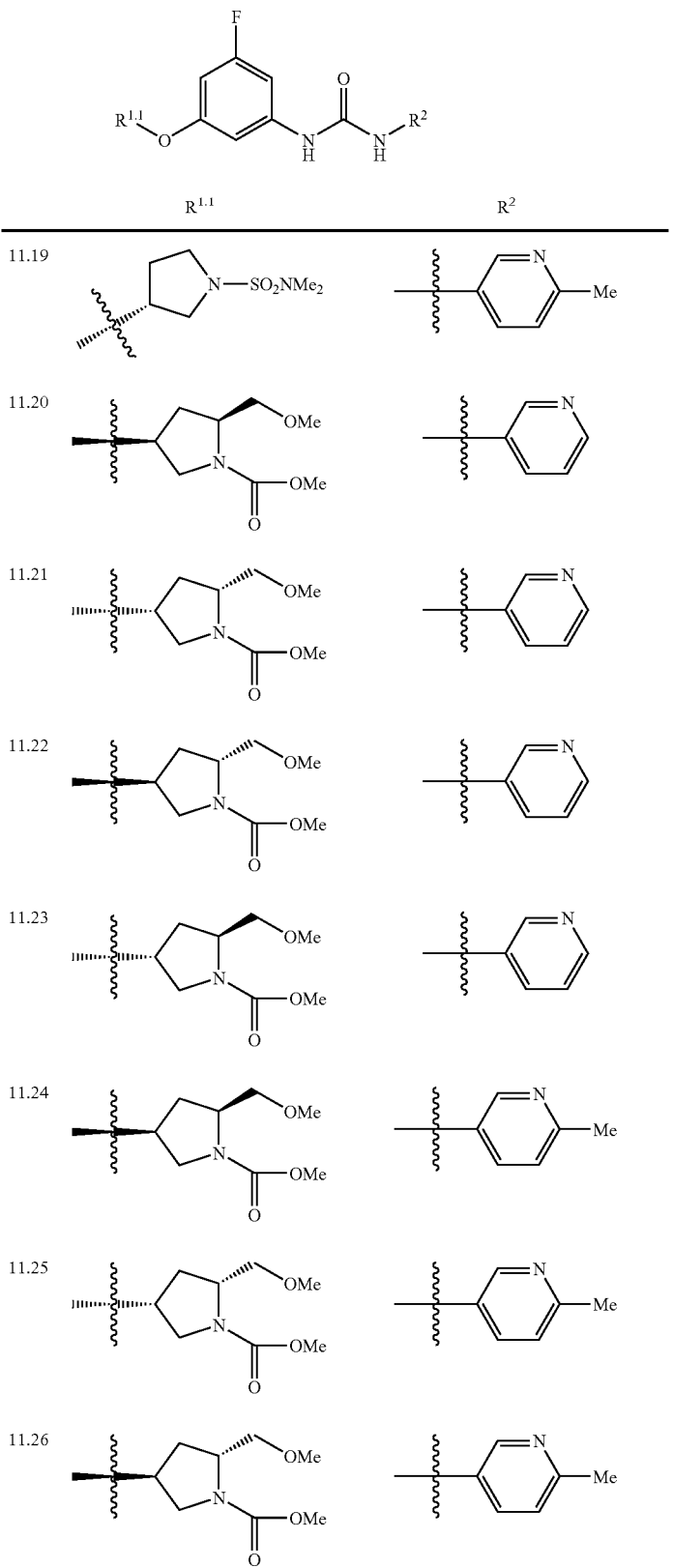

-continued

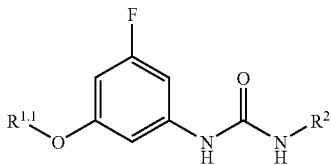

Formula III

| | $R^{1.1}$ | $R^2$ |
|---|---|---|
| 11.27 | 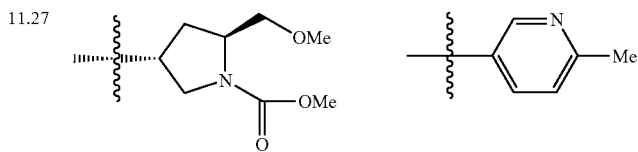 | |

Example 12

Other Compounds of Formula I

Similarly, by following the procedures illustrated in Examples 1 to 4 and with respect to Reaction Schemes 1 to 5, the following compounds were obtained:

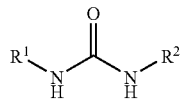

Formula I

| | $R^1$ | $R^2$ |
|---|---|---|
| 12.1 | Indan-1-yl | 3-hydroxy-phenyl- |
| 12.2 | Indan-1-yl | 3-Acetylamino-phenyl- |
| 12.3 | Indan-2-yl | 3-Acetylamino-phenyl- |
| 12.4 | Indan-1-yl | 3-Methanesulfonyl-amino-phenyl- |
| 12.5 | 1,2,3,4-Tetrahydro-naphthalene-1-yl | 3-Hydroxy-phenyl- |
| 12.6 | Indan-1-yl | 3-Carbamoylphenyl- |
| 12.7 | Indan-1-yl | 2-Methyl-3-hydroxyphenyl- |
| 12.8 | Indan-1-yl | 3-Hydroxy-4-methylphenyl- |
| 12.9 | Indan-1-yl | Pyridinyl |
| 12.10 | Indan-1-yl | Methoxypyridinyl- |
| 12.11 | 1,2,3,4-Tetrahydro-naphthalene-1-yl | Pyridinyl- |
| 12.12 | Indan-1-yl | 3-Hydroxy-5-fluorophenyl- |
| 12.13 | 4-methyl-indan-1-yl- | 3-Hydroxy-phenyl- |
| 12.14 | Indan-1-yl | 3-Methoxy-phenyl- |
| 12.15 | Indan-1-yl | 3-chloro-phenyl- |
| 12.16 | Indan-1-yl | Phenyl |
| 12.17 | Indan-1-yl | 3-fluoro-phenyl- |
| 12.18 | Indan-1-yl | 4-Methoxycarbonylphenyl- |
| 12.19 | Indan-1-yl | 3-Hydroxy-4-methylphenyl- |
| 12.20 | Indan-1-yl | Methylpyridinyl- |
| 12.21 | Indan-1-yl | 3-Carboxyphenyl- |
| 12.22 | Indan-1-yl | 3-Methoxy-4-chlorophenyl- |
| 12.23 | 1,2,3,4-Tetrahydro-naphthalene-1-yl | 3-Hydroxy-4-methylphenyl- |
| 12.24 | Indan-1-yl | 3-Aminosulfonylphenyl- |
| 12.25 | Indan-1-yl | 3-(Methylamino-sulfonyl)phenyl- |
| 12.26 | Indan-1-yl | Pyridinyl- |
| 12.27 | Indan-1-yl | 6-cyano-pyridin-3-yl |
| 12.28 | 1,2,3,4-Tetrahydro-naphthalene-1-yl | 3-Hydroxy-4-methoxyphenyl- |
| 12.29 | Indan-1-yl | 2-chloro-4-hydroxyphenyl- |
| 12.30 | 1,2,3,4-Tetrahydro-8-chloro-naphthalene-2-yl | 3-hydroxyphenyl- |
| 12.31 | 1,2,3,4-Tetrahydro-8-chloro-naphthalene-2-yl | 6-methyl-pyridin-3-yl |
| 12.32 | 1,2,3,4-Tetrahydro-naphthalene-1-yl | 6-methyl-pyridin-3-yl |
| 12.33 | Indan-1-yl | 6-methoxycarbonyl-pyridin-3-yl |
| 12.34 | Indan-1-yl | 6-carboxy-pyridin-3-yl |
| 12.35 | 6-methoxy-indan-1-yl | 3-hydroxyphenyl- |
| 12.36 | 1,2,3,4-Tetrahydro-naphthalene-2-yl | 3-hydroxyphenyl- |
| 12.37 | 4-chloro-indan-1-yl | 3-hydroxyphenyl- |
| 12.38 | 5-fluoro-indan-1-yl | 3-hydroxyphenyl- |
| 12.39 | 6-methyl-indan-1-yl | 3-hydroxyphenyl- |
| 12.40 | Indan-1-yl | 3-hydroxy-4-fluorophenyl- |
| 12.41 | Indan-1-yl | 3-hydroxy-4-chlorophenyl- |
| 12.42 | 1,2,3,4-Tetrahydro-naphthalene-1-yl | 3-acetoxy-phenyl |
| 12.43 | Indan-1-yl | 6-carbamoyl-pyridin-3-yl |
| 12.44 | Indan-1-yl | 6-trifluoromethyll-pyridin-3-yl |
| 12.45 | Indan-1-yl | Quinolin-3-yl |
| 12.46 | Indan-1-yl | 1H-Benzoimidazol-2-yl |
| 12.47 | 5,6,7,8-tetrahydro-isoquinolin-5-yl | 3-hydroxyphenyl- |
| 12.48 | 5,6,7,8-tetrahydro-isoquinolin-5-5-yl | 6-methyl-pyridin-3-yl |
| 12.49 | Indan-1-yl | 6-Oxo-1,6-dihydro-pyridine-3-yl |
| 12.50 | 6,7,8,9-tetrahydro-5H-benzocyclohepten-6-yl | 3-hydroxyphenyl- |
| 12.51 | Indan-1-yl | 5-Methyl-oxazole-2-yl |
| 12.52 | Indan-1-yl | oxazole-2-yl |
| 12.53 | Indan-1-yl | Isoxazole-3-yl |
| 12.54 | Indan-1-yl | 3-(2-Oxo-2,3-dihydro-1H-imidazol-4-yl)-phenyl- |
| 12.55 | Indan-1-yl | 5-Methyl-isoxazole-3-yl |
| 12.56 | Indan-1-yl | 3-Methyl-isoxazole-5-yl |
| 12.57 | Indan-1-yl | 3-(2-Amino-oxazol-4-yl)-phenyl |
| 12.58 | 6,7,8,9-tetrahydro-5H-benzocyclohepten-6-yl | 6-methyl-pyridin-3-yl |

Example 13

Other Compounds of Formula I

Similarly, by following the procedures illustrated in Examples 1 to 4 and with respect to Reaction Schemes 1 to 5, the following compounds corresponding to Formula III were obtained:

Formula III

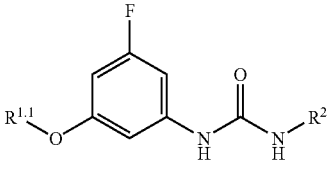

| | $R^{1.1}$ | $R^2$ |
|---|---|---|
| 13.1 | azepan-1-sulfonic acid dimethyl amide | pyridin-3-yl |
| 13.2 | azepan-1-carboxylic acid methyl ester | pyridin-3-yl |
| 13.3 | 3-oxo-tetrahydro-pyrrolo-pyridin-3-yl [1,2-c]-oxazol-6-yl | |
| 13.4 | 3-oxo-tetrahydro-pyrrolo-[1,2-c]-oxazol-6-yl | 6-methyl-pyridin-3-yl |
| 13.5 | 1-ethanesulfonyl-pyrrolidin-3-yl | 6-methyl-pyridin-3-yl |
| 13.6 | 1-propane-1-sulfonyl-pyrrolidin-3-yl | 6-methyl-pyridin-3-yl |
| 13.7 | 1-propane-2-sulfonyl-pyrrolidin-3-yl | 6-methyl-pyridin-3-yl |
| 13.8 | cyclopropane-sulfonyl-pyrrolidin-3-yl | 6-methyl-pyridin-3-yl |
| 13.9 | azepan-1-carboxylic acid t-butyl ester | 6-methyl-pyridin-3-yl |
| 13.10 | azepan-1-sulfonic acid dimethyl amide | 6-methyl-pyridin-3-yl |
| 13.11 | azepan-1-carboxylic acid methyl ester | 6-methyl-pyridin-3-yl |
| 13.12 | 1-methanesulfonyl-piperidin-3-yl | pyridin-3-yl |
| 13.13 | azepan-1-sulfonic acid dimethyl amide | pyridin-3-yl |

Example 14

Other Compounds of Formula I

Similarly, by following the procedures illustrated in Examples 1 to 4 and with respect to Reaction Schemes 1 to 5, the following compounds corresponding to Formula 14 were obtained:

Formula 14

| | $R^{1.1}$ | X | $R^2$ |
|---|---|---|---|
| 14.001 | (S)-1-acetyl-piperidin-3-yl | O | 6-(5-oxo-4,5-dihydro-[1,2,4]oxadiazol-3-yl)-pyridin-3-yl |
| 14.002 | (R)-1-acetyl-piperidin-3-yl | O | oxazol-2-yl |
| 14.003 | (R)-1-methoxycarbonyl-piperidin-3-yl | O | carbamoyl-pyridin-3-yl |
| 14.004 | (R)-1-dimethylamino-carbonyl-piperidin-3-yl | O | pyridine-2-carboxylic acide amide |
| 14.005 | (R)-1-acetyl-piperidin-3-yl | O | 2-methyl-pyridin-3-yl |
| 14.006 | (R)-1-acetyl-piperidin-3-yl | O | 6-ethyl-pyridin-3-yl |
| 14.007 | 1-methyl-2-oxo-piperidin-3-yl | O | pyridin-3-yl |
| 14.008 | 1-methyl-2-oxo-piperidin-3-yl | O | 6-methyl-pyridin-3-yl |
| 14.009 | (R)-1-acetyl-piperidin-3-yl | O | 1-methyl-6-oxo-1,6-dihydropyridin-3-yl |
| 14.010 | 1-acetyl-piperidin-3-yl | O | 2-methyl-pyrimidin-4-yl |
| 14.011 | (R)-1-formyl-piperidin-3-yl | O | 6-methyl-pyridin-3-yl |

-continued

Formula 14

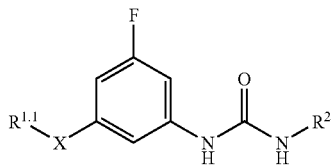

| | R[1.1] | X | R[2] |
|---|---|---|---|
| 14.012 | (R)-1-formyl-piperidin-3-yl | O | 6-ethyl-pyridin-3-yl |
| 14.013 | (R)-1-acetyl-piperidin-3-yl | O | 5-methyl-[1,3,4]-thiadiazol-2-yl |
| 14.014 | (R)-1-acetyl-piperidin-3-yl | O | pyridine-2-carboxylic acide amide |
| 14.015 | (R)-1-acetyl-piperidin-3-yl | O | 6-methyl-pyridin-3-yl |
| 14.016 | (R)-1-acetyl-piperidin-3-yl | O | 6-ethynyl-pyridin-3-yl |
| 14.017 | (R)-1-formyl-piperidin-3-yl | O | 6-isopropyl-pyridin-3-yl |
| 14.018 | (R)-1-acetyl-piperidin-3-yl | O | 6-isopropyl-pyridin-3-yl |
| 14.019 | (R)-1-acetyl-piperidin-3-yl | O | oxazol-5-yl |
| 14.020 | 2-oxo-piperidin-1-yl | $CH_2$—$CH_2$—O | pyridin-3-yl |
| 14.021 | (R)-1-methoxycarbonyl-piperidin-3-yl | O | pyridazin-4-yl |
| 14.022 | 2-oxo-piperidin-1-yl | $CH_2$—$CH_2$—O | 6-methoxy-pyridin-3-yl |
| 14.023 | 2-oxo-piperidin-1-yl | $CH_2$—$CH_2$—O | 6-methyl-pyridin-3-yl |
| 14.024 | (R)-1-dimethylamino-carbonyl-piperidin-3-yl | O | pyridazin-4-yl |
| 14.025 | (R)-1-formyl-piperidin-3-yl | O | 6-formyl-pyridin-3-yl |
| 14.026 | (R)-1-methylsulfonyl-piperidin-3-yl | O | 6-formyl-pyridin-3-yl |
| 14.027 | (R)-1-tert-butoxycarbonyl-piperidin-3-yl | O | pyridazin-4-yl |
| 14.028 | (R)-1-(morpholine-4-carbonyl)-piperidin-3-yl | O | 6-methyl-pyridin-3-yl |
| 14.029 | (R)-piperidine-1-carbonyl-amino acetic acid ethyl ester | O | 6-methyl-pyridin-3-yl |
| 14.030 | (R)-6-oxo-1-(tert-butoxycarbonyl)-piperidin-3-yl | O | 6-methyl-pyridin-3-yl |
| 14.031 | 6-oxo-piperidin-3-yl | O | 6-methyl-pyridin-3-yl |
| 14.032 | 2-oxo-piperidin-1-yl | $CH_2$—$CH(CH_3)$—O | pyridin-3-yl |
| 14.033 | 2-oxo-piperidin-1-yl | $CH_2$—$CH(CH_3)$—O | 6-methoxy-pyridin-3-yl |
| 14.034 | 2-oxo-piperidin-1-yl | $CH_2$—$CH(CH_3)$—O | 6-methyl-pyridin-3-yl |
| 14.035 | 3-oxo-morpholin-4-yl | $CH_2$—$CH(CH_3)$—O | pyridin-3-yl |
| 14.036 | 3-oxo-morpholin-4-yl | $CH_2$—$CH(CH_3)$—O | 6-methoxy-pyridin-3-yl |
| 14.037 | 3-oxo-morpholin-4-yl | $CH_2$—$CH(CH_3)$—O | 6-methyl-pyridin-3-yl |
| 14.038 | (R)-1-acetyl-piperidin-3-yl | O | pyridine-2-sulfonic acid amide |
| 14.039 | (R)-1-acetyl-piperidin-3-yl | O | pyridine-2-yl-N,N-dimethyl acetamide |
| 14.040 | (R)-1-acetyl-piperidin-3-yl | O | pyridine-2-yl-N-methyl acetamide |
| 14.041 | 1-acetyl-piperidin-3-yl | O | 6-methyl-pyridin-3-yl |
| 14.042 | (R)-1-acetyl-piperidin-3-yl | O | pyridin-2-yl acetamide |
| 14.043 | (R)-1-formyl-piperidin-3-yl | O | pyridin-2-ylmethyl acetamide |
| 14.044 | (R)-1-acetyl-piperidin-3-yl | O | pyridin-2-ylmethyl acetamide |
| 14.045 | (R)-1-dimethylamino-carbonyl-piperidin-3-yl | O | pyridin-2-ylmethyl acetamide |
| 14.046 | piperidin-3-yl | O | 4-fluoro-phenyl |
| 14.047 | piperidin-3-yl | O | 2-methyl-phenyl |
| 14.048 | piperidin-3-yl | O | 3-methyl-phenyl |
| 14.049 | piperidin-3-yl | O | 4-methyl-phenyl |
| 14.050 | piperidin-3-yl | O | 2-fluoro-phenyl |
| 14.051 | piperidin-3-yl | O | 3-fluoro-phenyl |
| 14.052 | (R)-1-ethylamino-carbonyl-piperidin-3-yl | O | 6-methyl-pyridin-3-yl |
| 14.053 | (R)-1-tert-butoxycarbonyl-piperidin-3-yl | O | 6-methoxymethyl-pyridin-3-yl |
| 14.054 | (R)-1-formyl-piperidin-3-yl | O | 6-methoxymethyl-pyridin-3-yl |
| 14.055 | (R)-1-dimethylamino-carbonyl-piperidin-3-yl | O | 6-benzyloxy-pyridin-3-yl |
| 14.056 | (R)-1-acetyl-piperidin-3-yl | O | 6-methoxymethyl-pyridin-3-yl |
| 14.057 | (R)-1-methoxycarbonyl-piperidin-3-yl | O | 6-methoxymethyl-pyridin-3-yl |
| 14.058 | (R)-1-dimethylamino-carbonyl-piperidin-3-yl | O | 6-methoxymethyl-pyridin-3-yl |
| 14.059 | (R)-1-methylsulfonyl-piperidin-3-yl | O | 6-methoxymethyl-pyridin-3-yl |

-continued

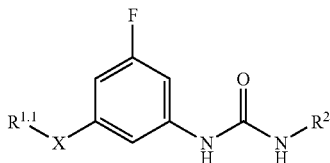

Formula 14

| | R[1.1] | X | R[2] |
|---|---|---|---|
| 14.060 | piperidin-3-yl | O | phenyl |
| 14.061 | (R)-1-formyl-piperidin-3-yl | O | 6-oxo-1,6-dihydro-pyridin-3-yl |
| 14.062 | (R)-1-dimethylamino-carbonyl-piperidin-3-yl | O | 6-oxo-1,6-dihydro-pyridin-3-yl |
| 14.063 | (R)-1-methoxycarbonyl-piperidin-3-yl | O | 6-oxo-1,6-dihydro-pyridin-3-yl |
| 14.064 | 1-acetyl-piperidin-3-yl | O | 2-hydroxymethyl-pyridin-3-yl |
| 14.065 | (R)-1-acetyl-piperidin-3-yl | O | 6-[1,3,4]-oxadiazol-2-yl-methyl-pyridin-3-yl |
| 14.066 | (R)-1-methoxycarbonyl-piperidin-3-yl | O | pyridin-2-ylmethyl acetamide |
| 14.067 | (R)-1-H-acetyl-piperidin-3-yl | O | pyridin-3-yl |
| 14.068 | (R)-piperidine-1-carbonyl-piperazine carboxylic acid ethyl ester | O | 6-methyl-pyridin-3-yl |
| 14.069 | (R)-1-formyl-piperidin-3-yl | O | 6-cyanomethyl-pyridin-3-yl |
| 14.070 | (R)-1-acetyl-piperidin-3-yl | O | 6-cyanomethyl-pyridin-3-yl |
| 14.071 | (R)-1-(1,1-dioxo-1λ6-thiomorpholine-4-carbonyl)-piperidin-3-yl | O | 6-methyl-pyridin-3-yl |
| 14.072 | (R)-1-methoxycarbonyl-piperidin-3-yl | O | 6-cyanomethyl-pyridin-3-yl |
| 14.073 | (R)-1-dimethylamino-carbonyl-piperidin-3-yl | O | 6-cyanomethyl-pyridin-3-yl |
| 14.074 | (R)-1-methylsulfonyl-piperidin-3-yl | O | 6-cyanomethyl-pyridin-3-yl |
| 14.075 | (R)-1-(4-pyridin-2-yl-piperazin-1-carbonyl)-piperidin-3-yl | O | 6-methyl-pyridin-3-yl |
| 14.076 | (R)-1-acetyl-piperidin-3-yl | O | 6-aminomethyl-pyridin-3-yl |
| 14.077 | (R)-1-methylsulfonyl-pyrrolidin-3-yl | O | 6-methyl-pyridin-3-yl |
| 14.078 | (S)-1-(cyclopropylsulfonyl)-piperidin-3-yl | O | pyridin-3-yl |
| 14.079 | (S)-1-(cyclopropylsulfonyl)-piperidin-3-yl | O | 6-methyl-pyridin-3-yl |
| 14.080 | (R)-1-acetyl-piperidin-3-yl | O | pyridin-2-ylmethyl-N-methyl formamide |
| 14.081 | (R)-1-acetyl-piperidin-3-yl | O | 6-ethyl-pyridin-3-yl |
| 14.082 | (R)-1-tert-butoxycarbonyl-piperidin-3-yl | O | pyridine-2-carboxamidine |
| 14.083 | 1-acetyl-azetidin-3-yl | $CH_2$—O | pyridin-3-yl |
| 14.084 | (R)-1-acetyl-piperidin-3-yl | O | pyridin-3-yl |
| 14.085 | (R)-1-acetyl-piperidin-3-yl | O | 6-methyl-pyridin-3-yl |
| 14.086 | (R)-1-[(R)-tetrahydro-furan-2-carbonyl]-piperidin-3-yl | O | pyridin-3-yl |
| 14.087 | (R)-1-[(4-ethoxycarbonyl-piperidn-1-yl)-carbonyl]-piperidin-3-yl | O | 6-methyl-pyridin-3-yl |
| 14.088 | (R)-1-(1,4-dioxa-8-aza-spiro[4.5]decane-8-carbonyl)-piperidin-3-yl | O | 6-methyl-pyridin-3-yl |
| 14.089 | (R)-4-hydroxy-piperidine-1-carbonyl-piperidin-3-yl | O | 6-methyl-pyridin-3-yl |
| 14.090 | (R)-1-[(4-formyl-piperidn-1-yl)-carbonyl]-piperidin-3-yl | O | 6-methyl-pyridin-3-yl |
| 14.091 | (R)-piperidine-1-carbonyl-piperidine-4-carboxylic acid methylamide | O | 6-methyl-pyridin-3-yl |
| 14.092 | (R)-1-acetyl-piperidin-3-yl | O | pyridin-2-ylmethyl-N-methyl formamide |
| 14.093 | (R)-1-[(S)-tetrahydro-furan-2-carbonyl]-piperidin-3-yl | O | pyridin-3-yl |
| 14.094 | (R)-1-(tetrahydro-furan-2-carbonyl)-piperidin-3-yl | O | pyridin-3-yl |
| 14.095 | (R)-1-[(R)-tetrahydro-furan-2-carbonyl]-piperidin-3-yl | O | 6-methyl-pyridin-3-yl |

-continued

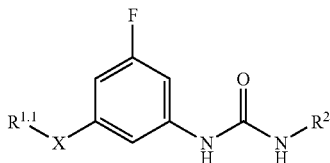

Formula 14

| | R¹·¹ | X | R² |
|---|---|---|---|
| 14.096 | (R)-1-[(S)-tetrahydro-furan-2-carbonyl]-piperidin-3-yl | O | 6-methyl-pyridin-3-yl |
| 14.097 | (R)-1-(tetrahydro-furan-2-carbonyl)-piperidin-3-yl | O | 6-methyl-pyridin-3-yl |
| 14.098 | (R)-1-[(S)-tetrahydro-furan-2-carbonyl-piperidin-3-yl | O | 6-ethyl-pyridin-3-yl |
| 14.099 | (R)-1-(tetrahydro-furan-2-carbonyl)-piperidin-3-yl | O | 6-ethyl-pyridin-3-yl |
| 14.100 | (R)-1-acetyl-piperidin-3-yl | O | 1H-imidazol-2-yl |
| 14.101 | (R)-1-dimethylamino-carbonyl-piperidin-3-yl | O | 1H-imidazol-2-yl |
| 14.102 | (R)-1-(4-tert-butoxycarbonyl-piperazine-carbonyl)-piperidin-3-yl | O | 6-methyl-pyridin-3-yl |
| 14.103 | (R)-[(R)-3-tert-butyl-dimethyl-silanyloxy]piperidine-1-carboxylic acid dimethylamide | O | 6-methyl-pyridin-3-yl |
| 14.104 | 1-(4-phenyl-piperazine-1-carbonyl)-piperidin-3-yl | O | 6-methyl-pyridin-3-yl |
| 14.105 | (R)-1-acetyl-piperidin-3-yl | O | pyridin-3-yl |
| 14.106 | (R)-1-acetyl-piperidin-3-yl | O | 6-methyl-pyridin-3-yl |
| 14.107 | (R)-1-acetyl-piperidin-3-yl | O | 6-ethyl-pyridin-3-yl |
| 14.108 | (R)-1-dimethylamino-carbonyl-piperidin-3-yl | O | pyridin-3-yl |
| 14.109 | (R)-1-dimethylamino-carbonyl-piperidin-3-yl | O | 6-methyl-pyridin-3-yl |
| 14.110 | (R)-1-dimethylamino-carbonyl-piperidin-3-yl | O | 6-ethyl-pyridin-3-yl |
| 14.111 | (R)-3-[(R)-tert-butyl-dimethyl-silanyloxy]piperidine-1-carboxylic acid dimethylamide | O | 6-methyl-pyridin-3-yl |
| 14.112 | (R)-piperidin-1-yl-2-oxoethyl-carbamic acid t-butyl ester | O | 6-methyl-pyridin-3-yl |
| 14.113 | (R)-1-acetyl-piperidin-3-yl | O | pyridine-2-carboxamidine |
| 14.114 | (R)-1-acetyl-[(R)-5-hydroxy]-piperidin-3-yl | O | 6-methyl-pyridin-3-yl |
| 14.115 | (R)-1-dimethylamino-carbonyl-[(R)-5-hydroxyl-piperidin-3-yl | O | 6-methyl-pyridin-3-yl |
| 14.116 | (R)-1-acetyl-[(R)-5-hydroxy]-piperidin-3-yl | O | pyridin-3-yl |
| 14.117 | (R)-1-dimethylamino-carbonyl-[(R)-5-hydroxy]-piperidin-3-yl | O | pyridin-3-yl |
| 14.118 | 2-oxo-pyrrolidin-1-yl | CH₂—CH(CH₃)—O | pyridin-3-yl |
| 14.119 | 2-oxo-pyrrolidin-1-yl | CH₂—CH(CH₃)—O | 6-methyl-pyridin-3-yl |
| 14.120 | 2-oxo-pyrrolidin-1-yl | CH₂—CH(CH₃)—O | 6-ethyl-pyridin-3-yl |
| 14.121 | (R)-1-acetyl-piperidin-3-yl | O | N-hydroxy-pyridine-2-carboxamidine |
| 14.122 | 2-oxo-piperidin-1-yl | CH₂—CH(CH₃)—O | 6-methyl-pyridin-3-yl |
| 14.123 | 1-methyl-6-oxo-piperidin-3-yl | O | pyridin-3-yl |
| 14.124 | (R)-N-(2-piperidin-1-yl)-2-oxo-ethyl acetamide | O | 6-methyl-pyridin-3-yl |
| 14.125 | (R)-2-[3-(piperidin-1-yl)-2-oxo-ethyl]-carbamic acid methyl ester | O | 6-methyl-pyridin-3-yl |
| 14.126 | (R)-1-[2-(3,3-dimethyl-ureido)-acetyl]-piperidin-3-yl | O | 6-methyl-pyridin-3-yl |
| 14.127 | (R)-morpholine-4-carboxylic acid [2-(piperidin-l-yl)-2-oxo-ethyl)-amide | O | 6-methyl-pyridin-3-yl |
| 14.128 | (R)-1-dimethylamino-carbonyl-[(R)-5-hydroxyl-piperidin-3-yl | O | 6-methoxymethyl-pyridin-3-yl |
| 14.129 | (R)-1-acetyl-[(R)-5-hydroxy]-piperidin-3-yl | O | 6-methyl-pyridin-3-yl |
| 14.130 | (R)-1-dimethylamino-carbonyl-[(R)-5-hydroxyl-piperidin-3-yl | O | 6-methyl-pyridin-3-yl |
| 14.131 | (R)-1-acetyl-[(R)-5-hydroxy]-piperidin-3-yl | O | pyridin-3-yl |

-continued

Formula 14

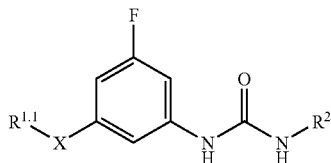

| | R$^{1.1}$ | X | R$^2$ |
|---|---|---|---|
| 14.132 | (R)-1-acetyl-piperidin-3-yl | O | N,N-dimethyl-pyridine-2-carboxamidine |
| 14.133 | 2-oxo-piperidin-1-yl | CH$_2$—CH(CH$_3$)—O | 6-methyl-pyridin-3-yl |
| 14.134 | 2-oxo-pyrrolidin-1-yl | CH$_2$—CH(CH$_3$)—O | pyridin-3-yl |
| 14.135 | 2-oxo-pyrrolidin-i-yl | CH$_2$—CH(CH$_3$)—O | 6-methyl-pyridin-3-yl |
| 14.136 | 2-oxo-pyrrolidin-1-yl | CH$_2$—CH(CH$_3$)—O | 6-ethyl-pyridin-3-yl |
| 14.137 | 2-oxo-piperidin-1-yl | CH$_2$—CH(CH$_3$)—O | pyridin-3-yl |
| 14.138 | 2-oxo-piperidin-1-yl | CH$_2$—CH(CH$_3$)—O | 6-ethyl-pyridin-3-yl |
| 14.139 | 1-methyl-6-oxo-piperidin-3-yl | O | 6-methyl-pyridin-3-yl |
| 14.140 | 1-methyl-6-oxo-piperidin-3-yl | O | 6-ethyl-pyridin-3-yl |
| 14.141 | 1-ethyl-6-oxo-piperidin-3-yl | O | pyridin-3-yl |
| 14.142 | 1-ethyl-6-oxo-piperidin-3-yl | O | 6-methyl-pyridin-3-yl |
| 14.143 | 1-ethyl-6-oxo-piperidin-3-yl | O | 6-ethyl-pyridin-3-yl |
| 14.144 | (R)-1-dimethylamino-carbonyl-[(R)-5-hydroxyl-piperidin-3-yl | O | pyridin-3-yl |
| 14.145 | (R)-1-acetyl-piperidin-3-yl | O | N-methyl-pyridine-2-carboxamidine |
| 14.146 | (R)-1-tert-butoxycarbonyl-piperidin-3-yl | O | pyridin-3-yl |
| 14.147 | (R)-1-(morpholine-4-carbonyl)-piperidin-3-yl | O | pyridin-3-yl |
| 14.148 | (R)-piperidine-1-carboxylic acid dimethylamide | O | 5-chloro-pyridin-3-yl |
| 14.149 | (R)-N-1-methyl-piperidine-1-carboxamidine | O | 6-methyl-pyridin-3-yl |
| 14.150 | (R)-1-(N$^2$-cyano-N$^1$,N$^1$-dimethyamidino)-piperidine-3-yl | O | 6-methyl-pyridin-3-yl |
| 14.151 | (R)-1-(N$^2$-cyano-amidino)-piperidin-3-yl | O | 6-methyl-pyridin-3-yl |
| 14.152 | (R)-1-acetyl-piperidin-3-yl | O | 6-guanidinocarbonyl-pyridin-3-yl |
| 14.153 | (R)-1-acetyl-piperidin-3-yl | O | pyridine-2-carboxylic acid dimethyl amide |
| 14.154 | (R)-1-acetyl-piperidin-3-yl | O | 5-chloro-pyridin-3-yl |
| 14.155 | (R)-1-(N$^2$-cyano-N$^1$-methyamidino)-piperidine-3-yl | O | 6-methyl-pyridin-3-yl |
| 14.156 | (R)-1-(N$^2$-cyano-amidino)-piperidin-3-yl | O | pyridin-3-yl |
| 14.157 | (R)-1-(tetrahydro-pyran-4-carbonyl)-piperidin-3-yl | O | 6-methyl-pyridin-3-yl |
| 14.158 | (R)-1-(N$^2$-cyano-N$^1$,N$^1$-dimethyamidino)-piperidine-3-yl | O | pyridin-3-yl |
| 14.159 | (R)-1-(N$^2$-cyano-N$^1$-methyamidino)-piperidine-3-yl | O | pyridin-3-yl |
| 14.160 | (R)-1-(N$^2$-cyano-N$^1$-methyamidino)-piperidine-3-yl | O | 6-methoxy-pyridin-3-yl |
| 14.161 | (R)-1-(N$^2$-cyano-amidino)-piperidin-3-yl | O | 6-methoxy-pyridin-3-yl |
| 14.162 | (R)-1-acetyl-piperidin-3-yl | O | 6-(N'-iminomethyl-N,N-dimethyl-guanidinomethyl)pyridin-3-yl |
| 14.163 | (R)-1-acetyl-piperidin-3-yl | O | 5-fluoro-pyridin-3-yl |
| 14.164 | (R)-1-(N$^2$-cyano-N$^1$,N$^1$-dimethyamidino)-piperidine-3-yl | O | 6-methoxy-pyridin-3-yl |
| 14.165 | (R)-1-(piperidine-4-carbonyl)-piperidin-3-yl | O | pyridin-3-yl |
| 14.166 | (R)-1-(pyrrolidine-1-carbonyl)-piperidin-3-yl | O | pyridin-3-yl |
| 14.167 | (R)-1-(azetidine-1-carbonyl)-piperidin-3-yl | O | pyridin-3-yl |
| 14.168 | (R)-1-methoxycarbonyl-piperidin-3-yl | O | 5-chloro-pyridin-3-yl |
| 14.169 | (R)-1-(cyanoimino-morpholin-4-yl-methyl)-piperidin-3-yl | O | 6-methoxy-pyridin-3-yl |
| 14.170 | (R)-1-(cyanoimino-morpholin-4- | O | pyridin-3-yl |
| 14.171 | (R)-1-tert-butoxycarbonyl- | O | 5-methyl-pyridin-3-yl |

-continued

Formula 14

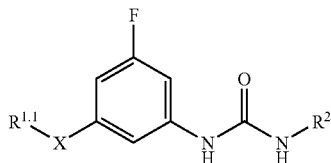

| | $R^{1.1}$ | X | $R^2$ |
|---|---|---|---|
| 14.172 | (R)-1-dimethylamino-carbonyl-piperidin-3-yl | O | 5-methyl-pyridin-3-yl |
| 14.173 | (R)-1-(cyanoimino-pyrrolidin-1-yl-methyl)-piperidin-3-yl | O | pyridin-3-yl |
| 14.174 | (R)-1-(cyanoimino-piperidin-1-yl-methyl-piperidin-3-yl | O | pyridin-3-yl |
| 14.175 | (R)-1-acetyl-piperidin-3-yl | O | 5-methyl-pyridin-3-yl |
| 14.176 | (R)-1-(1-imino-ethyl)-piperidin-3-yl | O | 6-methyl-pyridin-3-yl |
| 14.177 | (R)-1-(1-imino-ethyl)-piperidin-3-yl | O | pyridin-3-yl |
| 14.178 | (R)-1-acetyl-piperidin-3-yl | O | pyridin-2-yl |
| 14.179 | (R)-1-propionyl-1-piperidin-3-yl | O | pyridin-3-yl |
| 14.180 | (R)-1-isobutyryl-1-pineridin-3-yl | O | pyridin-3-yl |
| 14.181 | (R)-1-(2-methoxy-acetyl)-piperidin-3-yl | O | pyridin-3-yl |
| 14.182 | (R)-1-cyclopropanecarbonyl-1-piperidin-3-yl | O | pyridin-3-yl |
| 14.183 | (R)-1-(2-methoxy-propionyl)-piperidin-3-yl | O | pyridin-3-yl |
| 14.184 | 1-methyl-2-oxo-piperidin-3-yl | O | 6-methyl-pyridin-3-yl |
| 14.185 | 1-ethyl-2-oxo-piperidin-3-yl | O | 6-methyl-pyridin-3-yl |
| 14.186 | (R)-1-($N^1$-azetidin-1-yl-$N^2$-cyano-amidino)-piperidin-3-yl | O | 6-methyl-pyridin-3-yl |
| 14.187 | 1-dimethylamino-carbonyl-piperidin-4-yl | $CH_2$—$CH_2$—O | 6-methyl-pyridin-3-yl |
| 14.188 | (R)-1-($N^2$-cyano-$N^1$,$N^1$-dimethyamidino)-piperidine-3-yl | O | isoxazol-4-yl |
| 14.189 | (R)-1-($N^2$-cyano-$N^1$,$N^1$-dimethyamidino)-piperidine-3-yl | O | isoxazol-3-yl |
| 14.190 | (R)-1-($N^2$-cyano-$N^1$,$N^1$-dimethyamidino)-piperidine-3-yl | O | isoxazol-5-yl |
| 14.191 | (R)-1-(1-methyl-4,5-dihydro-1H-imidazol-2-yl)-piperidin-3-yl | O | pyridin-3-yl |
| 14.192 | (R)-1-methoxycarbonyl-piperidin-3-yl | O | 5-methyl-pyridin-3-yl |
| 14.193 | (R)-1-ethoxycarbonyl-piperidin-3-yl | O | pyridin-3-yl |
| 14.194 | (R)-1-iso-propoxycarbonyl-piperidin-3-yl | O | pyridin-3-yl |
| 14.195 | (R)-1-(cyanoimino-morpholin-4-yl-methyl)-piperidin-3-yl | O | isoxazol-3-yl |
| 14.196 | (R)-1-($N^1$-azetidin-1-yl-$N^2$-cyano-amidino)-piperidin-3-yl | O | isoxazol-3-yl |
| 14.197 | (R)-1-(1-acetyl-4,5-dihydro-1H-imidazol-2-yl)-piperidin-3-yl | O | pyridin-3-yl |
| 14.198 | (R)-1-(1-methylsulfonyl-4,5-dihydro-1H-imidazol-2-yl)-piperidin-3-yl | O | pyridin-3-yl |
| 14.199 | (R)-1-($N^2$-cyano-$N^1$-methoxyethyl-$N^1$-methylamidino)-piperidine-3-yl | O | pyridin-3-yl |
| 14.200 | (R)-1-methoxycarbonyl-piperidin-3-yl | O | 5-methoxy-pyridin-3-yl |
| 14.201 | (R)-1-acetyl-piperidin-3-yl | O | 5-methoxy-pyridin-3-yl |
| 14.202 | (R)-1-(1-methyl-4-oxo-4,5-dihydro-1H-imidazol-2-yl)-piperidin-3-yl | O | pyridin-3-yl |
| 14.203 | (R)-1-(1-methyl-4-oxo-4,5-dihydro-1H-imidazol-2-yl)-piperidin-3-yl | O | 6-methoxy-pyridin-3-yl |
| 14.204 | (R)-1-($N^1$-azetidin-1-yl-$N^2$-cyano-amidino)-piperidin-3-yl | O | pyridin-3-yl |
| 14.205 | (R)-1-[$N^2$-cyano-$N^1$-(pyrrolidin-2-yl carboxylic acid methyl ester]-amidino-piperidin-3-yl | O | pyridin-3-yl |

-continued

Formula 14

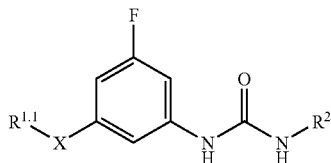

| | R[1.1] | X | R[2] |
|---|---|---|---|
| 14.206 | (R)-1-(N[2]-cyano-N[1]-methoxyethyl-N[1]-methylamidino)-piperidine-3-yl | O | 6-methyl-pyridin-3-yl |
| 14.207 | (R)-1-(dimethylaminosulfonyl)-piperidin-3-yl | O | pyridin-3-yl |
| 14.208 | (R)-1-(N[1]-azetidin-1-yl-N[2]-cyano-amidino)-piperidin-3-yl | O | 1-methyl-1H-pyrazol-3-yl |
| 14.209 | (R)-1-methoxycarbonyl-piperidin-3-yl | O | 1-methyl-1H-pyrazol-3-yl |
| 14.210 | (R)-1-cyano-piperidin-3-yl | O | pyridin-3-yl |
| 14.211 | (R)-1-(1H-tetrazol-5-yl)-piperidin-3-yl | O | pyridin-3-yl |
| 14.212 | (R)-1-(N[2]-cyano-N[1],N[1]-dimethylamidino)-piperidine-3-yl | O | 1-methyl-1H-pyrazol-3-yl |
| 14.213 | (R)-1-(2-methoxy-dicarbonyl)-piperidin-3-yl | O | pyridin-3-yl |
| 14.214 | (R)-1-(N[1]-azetidin-1-yl-N[2]-cyano-amidino)-piperidin-3-yl | O | 3-methyl-isoxazol-5-yl |
| 14.215 | (R)-1-(N[2]-cyano-N[1],N[1]-dimethylamidino)-piperidine-3-yl | O | 3-methyl-isoxazol-5-yl |
| 14.216 | (R)-1-(N[2]-cyano-N[1],N[1]-dimethylamidino)-piperidine-3-yl | O | 3-methyl-isoxazol-5-yl |
| 14.217 | (R)-1-(N[1]-azetidin-1-yl-N[2]-cyano-amidino)-piperidin-3-yl | O | 3-methyl-isoxazol-5-yl |
| 14.218 | (R)-1-(N[2]-cyano-N[1],N[1]-dimethylamidino)-piperidine-3-yl | O | 4-methyl-isoxazol-2-yl |
| 14.219 | (R)-1-(N[1]-azetidin-1-yl-N[2]-cyano-amidino)-piperidin-3-yl | O | 4-methyl-isoxazol-2-yl |
| 14.220 | (R)-1-(1-methyl-tetrazol-5-yl)-piperidin-3-yl | O | pyridin-3-yl |
| 14.221 | (R)-1-(N[1]-azetidin-1-yl-N[2]-cyano-amidino)-piperidin-3-yl | O | 6-methoxymethyl-pyridin-3-yl |
| 14.222 | (R)-1-(N[2]-cyano-N[1],N[1]-dimethylamidino)-piperidine-3-yl | O | 6-methoxymethyl-pyridin-3-yl |
| 14.223 | (R)-1-[N[2]-cyano-N[1]-(methyl-N[1]-methoxy-2-oxoethyl)amidino)-piperidine-3-yl | O | pyridin-3-yl |
| 14.224 | (R)-1-methoxyethoxycarbonyl-piperidin-3-yl | O | pyridin-3-yl |
| 14.225 | (R)-1-(dimethylaminosulfonyl)-piperidin-3-yl | O | 6-methyl-pyridin-3-yl |
| 14.226 | (R)-1-cyano-piperidin-3-yl | O | 6-methyl-pyridin-3-yl |
| 14.227 | (R)-1-(N[2]-cyano-N[1],N[1]-dimethylamidino)-piperidine-3-yl | O | isoxazol-2-yl |
| 14.228 | (R)-1-(N[1]-azetidin-1-yl-N[2]-cyano-amidino)-piperidin-3-yl | O | isoxazol-2-yl |
| 14.229 | (R)-1-(N[2]-cyano-N[1],N[1]-dimethylamidino)-piperidine-3-yl | O | 6-cyanomethyl-pyridin-3-yl |
| 14.230 | (R)-1-(N[1]-azetidin-1-yl-N[2]-cyano-amidino)-piperidin-3-yl | O | 6-cyanomethyl-pyridin-3-yl |
| 14.231 | (R)-1-(dimethylaminosulfonyl)-[(S)-5-methoxyl-piperidin-3-yl | O | 6-methyl-pyridin-3-yl |
| 14.232 | (R)-1-(N[2]-cyano-N[1],N[1]-dimethylamidino)-[(S)-5-methoxyl-piperidine-3-yl | O | 6-methyl-pyridin-3-yl |
| 14.233 | 1-(dimethylaminosulfonyl)-morpholin-2-yl | CH$_2$—O | pyridin-3-yl |
| 14.234 | 1-(dimethylaminosulfonyl)-morpholin-2-yl | CH$_2$—O | 6-methyl-pyridin-3-yl |
| 14.235 | 1-(N[2]-cyano-N[1],N[1]-dimethylamidino)-morpholin-2-yl | CH$_2$—O | pyridin-3-yl |
| 14.236 | 1-(N[2]-cyano-N[1],N[1]-dimethylamidino)-morpholin-2-yl | CH$_2$—O | 6-methyl-pyridin-3-yl |
| 14.237 | (R)-1-(tert-butoxy-carbonylaminosulfonyl)-piperidin-3-yl | O | pyridin-3-yl |

-continued

Formula 14

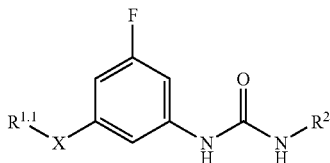

| | R[1.1] | X | R[2] |
|---|---|---|---|
| 14.238 | (R)-1-aminocarbonyl-piperidin-3-yl | O | pyridin-3-yl |
| 14.239 | (R)-1-aminosulfonyl-piperidin-3-yl | O | pyridin-3-yl |
| 14.240 | 1-(dimethylaminosulfonyl)-piperidin-4-yl | O | 6-methyl-pyridin-3-yl |
| 14.241 | 1-(N[2]-cyano-N[1],N[1]-dimethyamidino)-piperidine-4-yl | O | 6-methyl-pyridin-3-yl |
| 14.242 | (S)-1-(dimethylaminosulfonyl)-pyrrolidin-3-yl | O | 6-methyl-pyridin-3-yl |
| 14.243 | (R)-1-(dimethylaminosulfonyl)-pyrrolidin-3-yl | O | 6-methyl-pyridin-3-yl |
| 14.244 | (S)-1-(N[2]-cyano-N[1],N[1]-dimethyamidino)-pyrrolidin-3-yl | O | 6-methyl-pyridin-3-yl |
| 14.245 | (R)-1-(N[2]-cyano-N[1],N[1]-dimethyamidino)-pyrrolidin-3-yl | O | 6-methyl-pyridin-3-yl |
| 14.246 | 1-(dimethylaminosulfonyl)-piperidin-4-yl | O | pyridin-3-yl |
| 14.247 | 1-(N[2]-cyano-N[1],N[1]-dimethyamidino)-piperidine-4-yl | O | pyridin-3-yl |
| 14.248 | (S)-1-(dimethylaminosulfonyl)-pyrrolidin-3-yl | O | pyridin-3-yl |
| 14.249 | (S)-1-(N[2]-cyano-N[1],N[1]-dimethyamidino)-pyrrolidin-3-yl | O | pyridin-3-yl |
| 14.250 | (R)-1-(dimethylaminosulfonyl)-pyrrolidin-3-yl | O | pyridin-3-yl |
| 14.251 | (R)-1-(M-cyano-N[1],N[1]-dimethyamidino)-pyrrolidin-3-yl | O | pyridin-3-yl |
| 14.252 | (R)-1-(dimethylaminosulfonyl)-[(S)-5-methoxymethoxy]-piperidin-3-yl | O | pyridin-3-yl |
| 14.253 | (R)-1-(N[2]-cyano-N[1],N[1]-dimethyamidino)-[(S)-5-methoxymethoxy]-piperidine-3-yl | O | pyridin-3-yl |
| 14.254 | (R)-1-(dimethylaminosulfonyl)-piperidin-3-yl | O | 6-methoxymethyl-pyridin-3-yl |
| 14.255 | 2-cyanoimino-hexahydro-pyrimidin-5-yl | O | pyridin-3-yl |
| 14.256 | (R)-1-(methylaminosulfonyl)-piperidin-3-yl | O | pyridin-3-yl |
| 14.257 | (R)-1-methoxyethoxycarbonyl-piperidin-3-yl | O | 6-methyl-pyridin-3-yl |
| 14.258 | 1-methoxycarbonyl-piperidin-3-yl | O | pyridin-3-yl |
| 14.259 | 1-methoxycarbonyl-piperidin-3-yl | O | 6-methyl-pyridin-3-yl |
| 14.260 | (S)-1-methoxycarbonyl-pyrrolidin-3-yl | O | pyridin-3-yl |
| 14.261 | (S)-1-methoxycarbonyl-pyrrolidin-3-yl | O | 6-methyl-pyridin-3-yl |
| 14.262 | (R)-1-methoxycarbonyl-pyrrolidin-3-yl | O | 6-methyl-pyridin-3-yl |
| 14.263 | (R)-1-methoxycarbonyl-pyrrolidin-3-yl | O | pyridin-3-yl |
| 14.264 | 1-(N[2]-cyano-N[1],N[1]-dimethyamidino)-azetidin-3-yl | O | pyridin-3-yl |
| 14.265 | 1-acetyl-azetidin-3-yl | O | pyridin-3-yl |
| 14.266 | 1-dimethylamino-sulfonyl-azetidin-3-yl | O | pyridin-3-yl |
| 14.267 | (R)-1-[(N-methoxyethyl-N-methyl)-aminosulfonyl]-piperidin-3-yl | O | pyridin-3-yl |
| 14.268 | (R)-1-[(N-methoxyethyl-N-methyl)-aminosulfonyl]-piperidin-3-yl | O | 6-methyl-pyridin-3-yl |

-continued

Formula 14

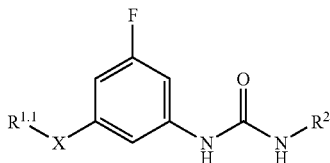

| | R$^{1.1}$ | X | R$^2$ |
|---|---|---|---|
| 14.269 | 1-methoxycarbonyl-azetidin-3-yl | O | pyridin-3-yl |
| 14.270 | 1-methoxycarbonyl-azetidin-3-yl | O | 6-methyl-pyridin-3-yl |
| 14.271 | 1-acetyl-azetidin-3-yl | O | 6-methyl-pyridin-3-yl |
| 14.272 | 1-dimethylamino-sulfonyl-azetidin-3-yl | O | 6-methyl-pyridin-3-yl |
| 14.273 | 1-(N$^2$-cyano-N$^1$,N$^1$-dimethyamidino)-azetidin-3-yl | O | 6-methyl-pyridin-3-yl |
| 14.274 | (R)-1-(isopropylsulfonyl)-piperidin-3-yl | O | pyridin-3-yl |
| 14.275 | (R)-1-(isopropylsulfonyl)-piperidin-3-yl | O | 6-methyl-pyridin-3-yl |
| 14.276 | (R)-[(R)-5-methoxy]-1-methoxycarbonyl-piperidin-3-yl | O | pyridin-3-yl |
| 14.277 | (R)-1-azetidin-1-ylsulfonyl-piperidin-3-yl | O | pyridin-3-yl |
| 14.278 | 1-ethoxycarbonyl-azetidin-3-yl | O | pyridin-3-yl |
| 14.279 | 1-ethoxycarbonyl-azetidin-3-yl | O | 6-methyl-pyridin-3-yl |
| 14.280 | 1-iso-propoxycarbonyl-azetidin-3-yl | O | pyridin-3-yl |
| 14.281 | 1-iso-propoxycarbonyl-azetidin-3-yl | O | 6-methyl-pyridin-3-yl |
| 14.282 | (R)-1-(2-dimethylamino-3,4-dioxo-cyclobut-1-enyl)-piperidin-3-yl | O | 6-methyl-pyridin-3-yl |
| 14.283 | (R)-1-(2-azetidin-1-yl-3,4-dioxo-cyclobut-1-enyl)-piperidin-3-yl | O | 6-methyl-pyridin-3-yl |
| 14.284 | (R)-1-(ethylsulfonyl)-piperidin-3-yl | O | pyridin-3-yl |
| 14.285 | (R)-1-(ethylsulfonyl)-piperidin-3-yl | O | 6-methyl-pyridin-3-yl |
| 14.286 | (R)-1-(dimethylaminosulfonyl)-[(S)-5-methoxyl-piperidin-3-yl | O | pyridin-3-yl |
| 14.287 | (R)-1-(N$^2$-cyano-N$^1$,N$^1$-dimethyamidino)-[(R)-5-methoxy]-piperidin-3-yl | O | pyridin-3-yl |
| 14.288 | (R)-1-(dimethylaminosulfonyl)-[(R)-5-methoxy]-piperidin-3-yl | O | pyridin-3-yl |
| 14.289 | (R)-1-(dimethylaminosulfonyl)-[(R)-5-methoxy]-piperidin-3-yl | O | 6-methyl-pyridin-3-yl |
| 14.290 | (R)-[(R)-5-methoxy]-1-methoxycarbonyl-piperidin-3-yl | O | 6-methyl-pyridin-3-yl |
| 14.291 | (R)-1-[(N-cyanomethyl-N-methyl)-aminosulfonyl]-piperidin-3-yl | O | pyridin-3-yl |
| 14.292 | (R)-1-(N$^2$-cyano-N$^1$,N$^1$-dimethyamidino)-piperidin-3-yl | O | pyridine-2-yl-N,N-dimethyl acetamide |
| 14.293 | (R)-1-(N$^1$-azetidin-1-yl-N$^2$-cyano-amidino)-piperidin-3-yl | O | pyridine-2-yl-N,N-dimethyl acetamide |
| 14.294 | (R)-1-(dimethylaminosulfonyl)-piperidin-3-yl | O | pyridine-2-yl-N,N-dimethyl acetamide |
| 14.295 | (S)-[1-methoxycarbonyl-(S)-2-methoxycarbonyl]-pyrrolidin-4-yl | O | pyridin-3-yl |
| 14.296 | (S)-[1-methoxycarbonyl-(R)-2-methoxycarbonyl]-pyrrolidin-4-yl | O | pyridin-3-yl |
| 14.297 | (S)-[1-methoxycarbonyl-(S)-2-methoxycarbonyl]-pyrrolidin-4-yl | O | 6-methyl-pyridin-3-yl |
| 14.298 | (S)-[1-methoxycarbonyl-(R)-2-methoxycarbonyl]-pyrrolidin-4-yl | O | 6-methyl-pyridin-3-yl |
| 14.299 | (S)-1-dimethylaminosulfonyl-2-methoxycarbonyl-pyrrolidin-4-yl | O | pyridin-3-yl |
| 14.300 | (S)-(N$^2$-cyano-N$^1$,N$^1$-dimethyamidino)-2-methoxycarbonyl-pyrrolidin-4-yl | O | pyridin-3-yl |
| 14.301 | (R)-1-acetyl-[(S)-5-methoxy]-piperidin-3-yl | O | 6-methyl-pyridin-3-yl |
| 14.302 | (R)-[(S)-5-methoxy]-1-methoxycarbonyl-piperidin-3-yl | O | 6-methyl-pyridin-3-yl |

-continued

Formula 14

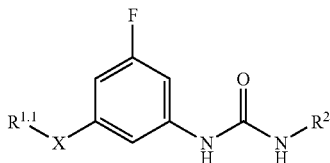

| | $R^{1.1}$ | X | $R^2$ |
|---|---|---|---|
| 14.303 | (S)-1-ethoxycarbonyl-pyrrolidin-4-yl | O | pyridin-3-yl |
| 14.304 | (S)-1-ethoxycarbonyl-pyrrolidin-4-yl | O | 6-methyl-pyridin-3-yl |
| 14.305 | (S)-1-iso-propoxycarbonyl-pyrrolidin-4-yl | O | pyridin-3-yl |
| 14.306 | (S)-1-iso-propoxycarbonyl-pyrrolidin-4-yl | O | 6-methyl-pyridin-3-yl |
| 14.307 | (S)-1-iso-propylsulfonyl-pyrrolidin-4-yl | O | pyridin-3-yl |
| 14.308 | (S)-1-iso-propylsulfonyl-pyrrolidin-4-yl | O | 6-methyl-pyridin-3-yl |
| 14.309 | (R)-1-(propylsulfonyl)-piperidin-3-yl | O | pyridin-3-yl |
| 14.310 | (R)-1-(propylsulfonyl)-piperidin-3-yl | O | 6-methyl-pyridin-3-yl |
| 14.311 | (S)-1-dimethylaminosulfonyl-pyrrolidin-2-yl | $CH_2$—O | pyridin-3-yl |
| 14.312 | (S)-1-methoxycarbonyl-pyrrolidin-2-yl | $CH_2$—O | pyridin-3-yl |
| 14.313 | (S)-1-dimethylaminosulfonyl-pyrrolidin-2-yl | $CH_2$—O | 6-methyl-pyridin-3-yl |
| 14.314 | (S)-1-methoxycarbonyl-pyrrolidin-2-yl | $CH_2$—O | 6-methyl-pyridin-3-yl |
| 14.315 | (R)-1-(ethylsulfonyl)-piperidin-3-yl | O | pyridine-2-yl-N,N-dimethyl acetamide |
| 14.316 | (R)-1-(isopropylsulfonyl)-piperidin-3-yl | O | pyridine-2-yl-N,N-dimethyl acetamide |
| 14.317 | (R)-1-methoxycarbonyl-piperidin-3-yl | O | pyridine-2-yl-N,N-dimethyl acetamide |
| 14.318 | (R)-1-ethoxycarbonyl-piperidin-3-yl | O | pyridine-2-yl-N,N-dimethyl acetamide |
| 14.319 | (R)-1-iso-propoxycarbonyl-piperidin-3-yl | O | pyridine-2-yl-N,N-dimethyl acetamide |
| 14.320 | (S)-1-dimethylaminosulfonyl-pyrrolidin-3-yl | $CH_2$—O | pyridin-3-yl |
| 14.321 | (S)-1-isopropylsulfonyl-pyrrolidin-3-yl | $CH_2$—O | pyridin-3-yl |
| 14.322 | (S)-1-ethylsulfonyl-pyrrolidin-3-yl | $CH_2$—O | pyridin-3-yl |
| 14.323 | (S)-1-methoxycarbonyl-pyrrolidin-3-yl | $CH_2$—O | pyridin-3-yl |
| 14.324 | (S)-1-iso-propoxycarbonyl-pyrrolidin-3-yl | $CH_2$—O | pyridin-3-yl |
| 14.325 | 1-ethoxycarbonyl-piperidin-4-yl | O | 6-methyl-pyridin-3-yl |
| 14.326 | 1-iso-propoxycarbonyl-piperidin-4-yl | O | 6-methyl-pyridin-3-yl |
| 14.327 | 1-(ethylsulfonyl)-piperidin-4-yl | O | 6-methyl-pyridin-3-yl |
| 14.328 | 1-(propylsulfonyl)-piperidin-4-yl | O | 6-methyl-pyridin-3-yl |
| 14.329 | 1-(isopropylsulfonyl)-piperidin-4-yl | O | 6-methyl-pyridin-3-yl |
| 14.330 | 1-(ethylsulfonyl)-piperidin-4-yl | O | pyridin-3-yl |
| 14.331 | 1-(isopropylsulfonyl)-piperidin-4-yl | O | pyridin-3-yl |
| 14.332 | 1-(propylsulfonyl)-piperidin-4-yl | O | pyridin-3-yl |
| 14.333 | 1-ethoxycarbonyl-piperidin-4-yl | O | pyridin-3-yl |
| 14.334 | 1-iso-propoxycarbonyl-piperidin-4-yl | O | pyridin-3-yl |
| 14.335 | (S)-1-($N^2$-cyano-$N^1,N^1$-dimethyamidino)-piperidin-3-yl | O | pyridin-3-yl |
| 14.336 | (R)-1-(dimethylsulfonyl)-[(S)-5-hydroxyl-piperidin-3-yl | O | 6-methyl-pyridin-3-yl |
| 14.337 | (S)-1-($N^2$-cyano-$N^1,N^1$-dimethyamidino)-piperidin-3-yl | O | 6-methyl-pyridin-3-yl |
| 14.338 | (S)-1-(dimethylsulfonyl)-piperidin-3-yl | O | pyridin-3-yl |

-continued

Formula 14

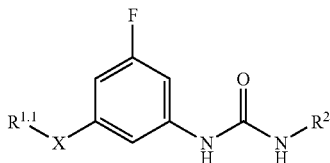

| | R^{1.1} | X | R^2 |
|---|---|---|---|
| 14.339 | (S)-1-(dimethylsulfonyl)-piperidin-3-yl | O | 6-methyl-pyridin-3-yl |
| 14.340 | (S)-[1-dimethylaminosulfonyl-(S)-2-methoxymethyl]-pyrrolidin-4-yl | O | pyridin-3-yl |
| 14.341 | (S)-[1-methoxycarbonyl-(S)-2-methoxymethyl]-pyrrolidin-4-yl | O | pyridin-3-yl |
| 14.342 | (S)-[1-dimethylaminosulfonyl-(S)-2-methoxymethyl]-pyrrolidin-4-yl | O | 6-methyl-pyridin-3-yl |
| 14.343 | (S)-[1-methoxycarbonyl-(S)-2-methoxymethyl]-pyrrolidin-4-yl | O | 6-methyl-pyridin-3-yl |
| 14.344 | 1-[(N-methoxyethyl-N-methyl)-aminosulfonyl]-piperidin-4-yl | O | 6-methyl-pyridin-3-yl |
| 14.345 | 1-[(N-methoxyethyl-N-methyl)-aminosulfonyl]-piperidin-4-yl | O | pyridin-3-yl |
| 14.346 | (R)-1-dimethylsulfonyl-pyrrolidin-4-yl | CH$_2$—O | pyridin-3-yl |
| 14.347 | (R)-1-methoxycarbonyl-pyrrolidin-4-yl | CH$_2$—O | pyridin-3-yl |
| 14.348 | (R)-1-dimethylsulfonyl-pyrrolidin-4-yl | CH$_2$—O | 6-methyl-pyridin-3-yl |
| 14.349 | (R)-1-methoxycarbonyl-pyrrolidin-4-yl | CH$_2$—O | 6-methyl-pyridin-3-yl |
| 14.350 | (R)-1-(dimethylsulfonyl)-oiperidin-3-yl | O | 6-methoxy-pyridin-3-yl |
| 14.351 | (S)-1-dimethylaminosulfonyl-pyrrolidin-3-yl | CH$_2$—O | 6-methyl-pyridin-3-yl |
| 14.352 | (S)-1-iso-propylsulfonyl-pyrrolidin-3-yl | CH$_2$—O | 6-methyl-pyridin-3-yl |
| 14.353 | (S)-1-ethylsulfonyl-pyrrolidin-3-yl | CH$_2$—O | 6-methyl-pyridin-3-yl |
| 14.354 | (S)-1-methoxycarbonyl-pyrrolidin-3-yl | CH$_2$—O | 6-methyl-pyridin-3-yl |
| 14.355 | (S)-1-iso-propoxycarbonyl-pyrrolidin-3-yl | CH$_2$—O | 6-methyl-pyridin-3-yl |
| 14.356 | (R)-[(R)-3-methoxy]-piperidin-5-yl | O | 6-methyl-pyridin-3-yl |
| 14.357 | (S)-1-(ethylsulfonyl)-piperidin-3-yl | O | pyridin-3-yl |
| 14.358 | (S)-1-(dimethylsulfonyl)-piperidin-3-yl | O | pyridin-3-yl |
| 14.359 | (S)-1-(propylsulfonyl)-piperidin-3-yl | O | pyridin-3-yl |
| 14.360 | (S)-1-methoxycarbonyl-piperidin-3-yl | O | pyridin-3-yl |
| 14.361 | (S)-1-ethoxycarbonyl-piperidin-3-yl | O | pyridin-3-yl |
| 14.362 | (S)-1-iso-propoxycarbonyl-piperidin-3-yl | O | pyridin-3-yl |
| 14.363 | (S)-1-(ethylsulfonyl)-piperidin-3-yl | O | 6-methyl-pyridin-3-yl |
| 14.364 | 1-(dimethylsulfonyl)-4-methoxy-piperidin-3-yl | O | pyridin-3-yl |
| 14.365 | (S)-1-(isopropylsulfonyl)-piperidin-3-yl | O | 6-methyl-pyridin-3-yl |
| 14.366 | (R)-[(S)-4-methoxy]-1-methoxycarbonyl-piperidin-3-yl | O | pyridin-3-yl |
| 14.367 | (S)-1-(propylsulfonyl)-piperidin-3-yl | O | 6-methyl-pyridin-3-yl |
| 14.368 | (S)-1-methoxycarbonyl-piperidin-3-yl | O | 6-methyl-pyridin-3-yl |
| 14.369 | (R)-1-(dimethylsulfonyl)-[(S)-4-methoxyl-piperidin-3-yl | O | 6-methyl-pyridin-3-yl |
| 14.370 | (S)-1-ethoxycarbonyl-piperidin-3-yl | O | 6-methyl-pyridin-3-yl |

-continued

Formula 14

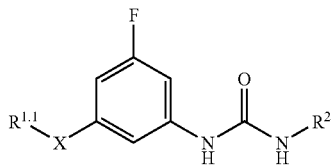

| | R[1.1] | X | R[2] |
|---|---|---|---|
| 14.371 | (R)-[(S)-4-methoxy]-1-methoxycarbonyl-piperidin-3-yl | O | 6-methyl-pyridin-3-yl |
| 14.372 | (S)-1-iso-propoxycarbonyl-piperidin-3-yl | O | 6-methyl-pyridin-3-yl |
| 14.373 | (R)-[1-dimethylaminosulfonyl-(R)-3-methoxyl-pyrrolidin-4-yl | O | 6-methyl-pyridin-3-yl |
| 14.374 | (R)-[(R)-3-methoxy-1-methoxycarbonyl]-pyrrolidin-4-yl | O | 6-methyl-pyridin-3-yl |
| 14.375 | (R)-[1-iso-propylsulfonyl-(R)-3-methoxyl-pyrrolidin-4-yl | O | 6-methyl-pyridin-3-yl |
| 14.376 | (R)-[(R)-5-(2,2,2-trifluoroethoxy)]-piperidin-3-yl | O | pyridin-3-yl |
| 14.377 | (S)-1-ethoxysulfonyl-pyrrolidin-4-yl | O | pyridin-3-yl |
| 14.378 | (S)-1-ethoxysulfonyl-pyrrolidin-4-yl | O | 6-methyl-pyridin-3-yl |
| 14.379 | (S)-1-propoxysulfonyl-pyrrolidin-4-yl | O | pyridin-3-yl |
| 14.380 | (S)-1-propoxysulfonyl-pyrrolidin-4-yl | O | 6-methyl-pyridin-3-yl |
| 14.381 | (R)-1-iso-propylsulfonyl-[(S)-2-methoxyethyl]-pyrrolidin-4-yl | O | pyridin-3-yl |
| 14.382 | (R)-[(S)-2-dimethylaminocarbonyl-1-dimethylaminosulfonyl]-pyrrolidin-4-yl | O | pyridin-3-yl |
| 14.383 | (R)-[1-dimethylaminocarbonyl-(S)-2-dimethylaminosulfonyl]-pyrrolidin-4-yl | O | pyridin-3-yl |
| 14.384 | (R)-[1-dimethylaminocarbonyl-(S)-2-dimethylaminosulfonyl]-pyrrolidin-4-yl | O | 6-methyl-pyridin-3-yl |
| 14.385 | (R)-[(S)-2-dimethylaminosulfonyl-1-methoxycarbonyl]-pyrrolidin-4-yl | O | 6-methyl-pyridin-3-yl |
| 14.386 | (S)-1-cyclopropylsulfonyl-pyrrolidin-4-yl | O | pyridin-3-yl |
| 14.387 | (S)-1-cyclopropylsulfonyl-pyrrolidin-4-yl | O | 6-methyl-pyridin-3-yl |
| 14.388 | (R)-(1-cyclopropylsulfonyl-(R)-3-methoxyl-pyrrolidin-4-yl | O | 6-methyl-pyridin-3-yl |
| 14.389 | (R)-[1-ethylsulfonyl-(R)-3-methoxyl-pyrrolidin-4-yl | O | 6-methyl-pyridin-3-yl |
| 14.390 | (R)-1-ethylsulfonyl-pyrrolidin-4-yl | O | pyridin-3-yl |
| 14.391 | (R)-1-propylsulfonyl-pyrrolidin-4-yl | O | pyridin-3-yl |
| 14.392 | (R)-1-cyclopropylsulfonyl-pyrrolidin-4-yl | O | pyridin-3-yl |
| 14.393 | (R)-1-(cyclopropylsulfonyl)-piperidin-3-yl | O | pyridin-3-yl |
| 14.394 | (R)-1-(cyclopropylsulfonyl)-piperidin-3-yl | O | 6-methyl-pyridin-3-yl |
| 14.395 | azepan-4-yl | O | pyridin-3-yl |
| 14.396 | 1-dimethylsulfonyl-azepan-4-yl | O | pyridin-3-yl |
| 14.397 | 1-methoxycarbonyl-azepan-4-yl | O | pyridin-3-yl |
| 14.398 | (R)-[1-ethylsulfonyl-(S)-2-methoxymethyl]-pyrrolidin-4-yl | O | pyridin-3-yl |
| 14.399 | (R)-[1-cyclopropylsulfonyl-(S)-2-methoxymethyl]-pyrrolidin-4-yl | O | pyridin-3-yl |
| 14.400 | (R)-[1-ethylsulfonyl-(S)-2-methoxymethyl]-pyrrolidin-4-yl | O | 6-methyl-pyridin-3-yl |
| 14.401 | (R)-[1-cyclopropylsulfonyl-(S)-2-methoxymethyl]-pyrrolidin-4-yl | O | 6-methyl-pyridin-3-yl |

Example 15

Other Compounds of Formulas I

Similarly, by following the procedures illustrated in Examples 1 to 4 and with respect to Reaction Schemes 1 to 5, the following compounds corresponding to Formula III were obtained:

Formula III

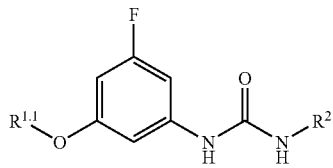

| | R$^{1.1}$ | R$^2$ |
|---|---|---|
| 15.1 | Pyridinyl | Fluorophenyl |
| 15.2 | Pyridinyl | Methylphenyl |
| 15.3 | Pyridinyl | Phenyl |
| 15.4 | Pyridinyl | Dimethylacetamido-phenyl- |
| 15.5 | Pyridinyl | Ethoxycarbonyl-pyridinyl- |
| 15.6 | Pyridinyl | Ethylenedioxy-phenyl- |
| 15.7 | Pyridinyl | Imidazolyl- |
| 15.8 | Pyridinyl | Hydroxyphenyl- |
| 15.9 | Pyridinyl | Pyrrolidin-1-yl-pyridinyl- |
| 15.10 | Pyridinyl | (2,6-Dimethyl-morpholin-4-yl)-pyridinyl- |
| 15.11 | Pyridinyl | (Pyridin-2-ylsulfanyl)-pyridinyl- |
| 15.12 | Pyridinyl | Quinolinyl- |
| 15.13 | Pyridinyl | 3,4-Dimethyl-isoxazolyl- |
| 15.14 | Pyridinyl | Ethoxycarbonyl-imidazolyl- |
| 15.15 | Pyrdinyl | 4-Acetylamino-pyridinyl- |
| 15.16 | Pyridinyl | Trifluoromethyl-pyridinyl- |
| 15.17 | Pyridinyl | Carbamoyl-phenyl- |
| 15.18 | Pyridinyl | (1-Hydroxy-ethyl)-phenyl- |
| 15.19 | Pyridinyl | (2-Oxo-imidazolidin-1-yl)-pyridinyl- |
| 15.20 | Pyridinyl- | (2-Hydroxy-ethylamino)-pyridinyl- |
| 15.21 | Pyridinyl | (2-Hydroxy-ethoxy)-pyridinyl- |
| 15.22 | Pyridinylmethyl- | Methoxyphenyl- |
| 15.23 | Pyridinyl- | Hydroxymethyl-oxazolyl- |
| 15.24 | Pyridinyl | Methoxymethyl-isoxazolyl- |
| 15.25 | Fluoropyridinyl- | Methoxyphenyl- |
| 15.26 | Pyridinyl- | Dimethoxyphenyl- |
| 15.27 | Pyridinyl- | Dimethoxypyridinyl- |
| 15.28 | Pyridinyl- | Pyridinyl |
| 15.29 | Pyridinyl- | Isoxazolyl- |
| 15.30 | Pyridinyl- | 1H-Pyrazolyl- |
| 15.31 | Pyridinyl- | Fluoro-chloro-phenyl- |
| 15.32 | Pyridinyl- | Chloro-methoxy-phenyl- |
| 15.33 | Pyridinyl- | Chloro-methyl-phenyl- |
| 15.34 | Pyridinyl- | Fluoro-methoxy-phenyl- |
| 15.35 | Pyridinyl- | Methylsulfanyl-phenyl- |
| 15.36 | Pyridinyl- | Acetylphenyl- |
| 15.37 | Pyridinyl- | Methyl-methoxyphenyl- |
| 15.38 | Pyridinyl- | Methoxyphenyl- |
| 15.39 | Pyridinyl- | Methoxypyridinyl- |
| 15.40 | Pyridinyl- | [1,2,4]Thiadiazolyl- |
| 15.41 | Pyridinyl- | [1,3,4]Thiadiazolyl- |
| 15.42 | Pyridinyi- | Methylcarbamoyl-phenyl- |
| 15.43 | Pyridinyi- | Thiazolyl- |
| 15.44 | Pyridinyl- | Ethylsulfanyl-[1,3,4]thiadiazolyl- |
| 15.45 | Pyridinyl- | Cyanophenyl- |
| 15.46 | Pyridinyl- | Carbamoyl-phenyl- |
| 15.47 | Pyridinyl- | Pyrazinyl- |
| 15.48 | Pyridinyl- | Methoxycarbonyl-phenyl- |
| 15.49 | Pyridinyl- | Hydroxymethyl-phenyl- |
| 15.50 | 2-Pyridinylethyl- | Methoxy-phenyl- |
| 15.51 | Pyridinyl- | Hydroxyethyl-phenyl- |
| 15.52 | Pyridinyl- | Cyanopyridinyl |
| 15.53 | Pyridinyl- | Pyridinyl- |
| 15.54 | Pyridinyl- | 5-Methyl-isoxazolyl- |
| 15.55 | Pyridinyl | 3-Methyl-isoxazolyl- |
| 15.56 | Pyridinyl- | Ethoxy-pyridinyl- |
| 15.57 | Pyridinyl- | Carboxy-phenyl- |
| 15.58 | Acetylphenyl- | Pyridinyl- |
| 15.59 | Pyridinyl- | Methylenedioxyphenyl- |
| 15.60 | 3-Pyridinylprop-2-yl- | Pyridinyl- |
| 15.61 | Pyridinylmethyl- | Pyridinyl- |
| 15.62 | Pyridinylmethyl- | Pyridinyl- |
| 15.63 | 3-Pyridinylprop-2-yl- | Hydroxyphenyl |
| 15.64 | Hydroxmethylphenyl- | Hydroxyphenyl- |
| 15.65 | 1-Pyridinyl-ethyl- | Hydroxyphenyl- |
| 15.66 | 1-Methoxy-prop-2-yl- | Methoxypyridinyl- |
| 15.67 | 1-Methoxy-prop-2-yl | Pyridinyl- |
| 15.68 | Tetrahydrofuranyl- | Methoxypyridinyl- |
| 15.69 | Pyridinylmethyl- | Hydroxyphenyl- |
| 15.70 | Tetrahydrofuranyl- | Pyridinyl |
| 15.71 | Pyridinyl- | Hydroxyphenyl- |
| 15.72 | Pyridinyl- | Methylcarbmoyl-phenyl- |
| 15.73 | Pyridinyl- | Hydroxypropyl-phenyl- |
| 15.74 | Hydroxymethyl-phenyl- | Methoxyphenyl- |
| 15.75 | Pyridinyl- | 5-Cyclopropyl-[1,3,4]thiadiazolyl- |
| 15.76 | Acetylphenyl- | Methoxyphenyl- |
| 15.77 | Pyridinyl- | Carbamoylpyridinyl- |
| 15.78 | Pyridinyl- | Pyrimidinyl- |
| 15.79 | Pyridinyl- | 3-Methyl-isothiazolyl- |
| 15.80 | Hydroxymethyl-phenyl- | Pyridinyl- |
| 15.81 | 1-Hydroxyethyl-phenyl- | Pyridinyl- |
| 15.82 | 1-Pyridinylethyl- | Pyridinyl- |
| 15.83 | Pyridinyl- | Dichlorophenyl- |
| 15.84 | Pyridinyl- | Acetylphenyl- |
| 15.85 | Pyridinyl- | Methoxyphenyl- |
| 15.86 | Pyridinyl- | Dimethylamino-phenyl- |
| 15.87 | Pyridinyl- | Morpholin-4-yl-pyridinyl- |

Example 16

Other Compounds of Formula I

Similarly, by following the procedures illustrated in Examples 1 to 4 and with respect to Reaction Schemes 1 to 5, the following compounds corresponding to Formula 16 were obtained:

Formula 16

| | R$^a$ | R$^2$ |
|---|---|---|
| 16.01 | Acetyl- | Pyridazinyl- |
| 16.02 | Acetyl- | Methylpyridazinyl- |

Formula 16

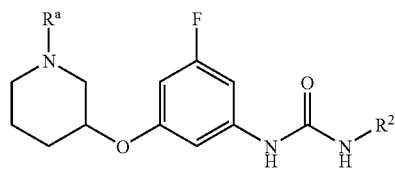

| | $R^a$ | $R^2$ |
|---|---|---|
| 16.03 | Acetyl- | Methoxypyridazinyl- |
| 16.04 | Acetyl- | Methoxypyrimidinyl- |
| 16.05 | Acetyl- | Methylpyrimidinyl- |
| 16.06 | Acetyl- | Pyrimidinyl- |
| 16.07 | N'-Cyano-N,N-dimethyl-carbamimidoyl- | Methylpyridinyl- |
| 16.08 | N'-Cyano-N,N-dimethyl-carbamimidoyl- | Pyridinyl- |
| 16.09 | Ethylcarbomyl- | Methoxyphenyl- |
| 16.10 | Methoxycarbonyl- | Methoxyphenyl- |
| 16.11 | Ethylcarbamoyl- | Methylpyridinyl- |
| 16.12 | 2-Methyoxyacetyl- | Methoxyphenyl- |
| 16.13 | Acetyl- | Acetylpyridinyl- |
| 16.14 | Dimethylcarbamoyl- | Pyridinyl- |
| 16.15 | Dimethylcarbamoyl- | Methoxypyridinyl- |
| 16.16 | Acetyl- | Pyridinyl- |
| 16.17 | Acetyl- | Cyanopyridinyl- |
| 16.18 | Acetyl- | Pyridinyl- |
| 16.19 | Acetyl- | 1-Hydroxyethyl-pyridinyl- |
| 16.20 | Methoxycarbonyl- | Cyanopyridinyl- |
| 16.21 | Acetyl- | Methoxypyridinyl- |
| 16.22 | Acetyl- | Methylsulfanylpyridinyl- |
| 16.23 | Acetyl- | Trifluoromethyl-pyridinyl- |
| 16.24 | Methoxycarbonyl- | Pyridinyl- |
| 16.25 | Dimethylcarbamoyl- | Cyanopyridinyl- |
| 16.26 | Methoxycarbonyl- | Methoxypyridinyl- |
| 16.27 | Methoxymethylcarbonyl- | Pyridinyl- |
| 16.28 | Methylsulfonyl- | Pyridinyl- |
| 16.29 | Dimethylcarbamoyl- | Methoxypyridinyl- |
| 16.30 | Ethylcarbamoyl- | Pyridinyl- |
| 16.31 | Dimethylcarbamoyl- | Pyridinyl- |
| 16.32 | Propionyl- | Methoxypyridinyl- |
| 16.33 | Isobutyryl- | Methoxyphenyl- |
| 16.34 | Propionyl- | Methoxyphenyl- |
| 16.35 | Methylsulfonyl- | Methoxyphenyl- |
| 16.36 | Methylsulfonyl- | Methoxypyridinyl- |
| 16.37 | Methoxycarbonyl- | (Acetylamino-methyl)pyridinyl- |
| 16.38 | Dimethylcarbamoyl | Carbamoyl- |
| 16.39 | Methylsulfonyl- | Cyanopyridinyl- |
| 16.40 | Methylsulfonyl- | Methoxymethylpyridinyl |
| 16.41 | Acetyl- | Methylcarbamoylmethyl-pyridinyl- |
| 16.42 | Acetyl- | Ethylpyridinyl- |
| 16.43 | Acetyl- | Methylpyridinyl |
| 16.44 | Propionyl- | Pyridinyl- |
| 16.45 | Dimethylcarbamoyl- | Methoxymethyl-pyridinyl- |
| 16.46 | Methoxycarbonyl- | Methoxymethyl-pyridinyl- |
| 16.47 | Acetyl- | (Acetylamino-methyl)pyridinyl- |
| 16.48 | Dimethylcarbamoyl- | (Acetylamino-methyl)pyridinyl- |
| 16.49 | Acetyl- | Methoxymethyl-pyridinyl- |
| 16.50 | Methylsulfonyl- | Carbamoylpyridinyl- |
| 16.51 | Acetyl- | Carbamoyl-pyridinyl- |
| 16.52 | Dimethylcarbamoyl- | Methylpyridinyl- |
| 16.53 | Methylsulfonyl- | Pyridinyl- |
| 16.54 | Acetyl | Carbamoyl-methyl-pyridinyl- |
| 16.55 | Methoxycarbonyl- | Methylpyridinyl- |
| 16.56 | Methylsulfonyl- | Methylpyridinyl- |
| 16.57 | Methylsulfonyl- | Methoxypyridinyl- |
| 16.58 | Methoxycarbonyl- | Carbamoylpyridinyl- |
| 16.59 | 4-hydroxy-piperidine-1-carbonyl- | Methylpyridinyl- |
| 16.60 | 4-Ethoxycarbonyl-piperidine-1-carbonyl | Methylpyridinyl- |
| 16.61 | Acetyl- | Isoxazol-5-yl |

Example 17

Other Compounds of Formula I

Similarly, by following the procedures illustrated in Examples 1 to 4 and with respect to Reaction Schemes 1 to 5, the following compounds corresponding to Formula 17 were obtained:

Formula 17

| | $R^{1.1}$ | $R^2$ |
|---|---|---|
| 17.01 | Pyridinyl | Methoxyphenyl- |
| 17.02 | Pyridinyl | Phenyl |
| 17.03 | Pyridinyl | Methoxyfluorophenyl- |
| 17.04 | Pyridinyl | Dimethoxyphenyl- |
| 17.05 | Pyridinyl | Fluorophenyl- |
| 17.06 | Pyridinyl | Methylsulfanylphenyl- |
| 17.07 | Pyridinyl | Dimethoxypyridinyl- |
| 17.08 | Pyridinyl | Acetylphenyl- |
| 17.09 | Pyridinyl | Methoxypyridinyl |
| 17.10 | Pyridinyl | Pyridinyl |
| 17.11 | Pyridinyl | Fluoropyridinyl |
| 17.12 | Pyridinyl | Methoxyphenyl |
| 17.13 | Pyridinyl | Flurochlorophenyl- |
| 17.14 | Pyridinyl | Dimethylaminophenyl- |
| 17.15 | Pyridinyl | Chloromethoxyphenyl- |
| 17.16 | Pyridinyl | Isoxazolyl- |
| 17.17 | Pyridinyl | 1H-Pyrazolyl- |
| 17.18 | Pyridinyl | Chloropyridinyl- |
| 17.19 | Pyridinyl | Pyrimidinyl |
| 17.20 | Pyridinyl | Methylphenyl |

Example 18

Target Identification Assays

Specificity assays: Compound specificity towards cardiac myosin is evaluated by comparing the effect of the compound on actin-stimulated ATPase of a panel of myosin isoforms: cardiac, skeletal and smooth muscle, at a single 50 µM compound concentration.

Myofibril assays: To evaluate the effect of compounds on the ATPase activity of full-length cardiac myosin in the context of native sarcomere, skinned myofibril assays are performed. Rat cardiac myofibrils are obtained by homogenizing rat cardiac tissue in the presence of detergent. Such treatment removes membranes and majority of soluble cytoplasmic proteins but leaves intact cardiac sarcomeric acto-myosin apparatus. Myofibril preparations retain the ability to hydrolyze ATP in an $Ca^{++}$ controlled manner. ATPase activities of such myofibril preparations in the presence and absence of compounds are assayed at $Ca^{++}$ concentrations giving 50% and 100% of a maximal rate.

Example 19

In Vitro Model of Dose Dependent Cardiac Myosin ATPase Modulation

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1\times10^{-4}$ M to $1\times10^{-8}$ M.

The protein components specific to this assay are bovine cardiac myosin subfragment-1 (typically 0.5 μM), bovine cardiac actin (14 μM), bovine cardiac tropomyosin (typically 3 μM), and bovine cardiac troponin (typically 3-8 μM). The exact concentrations of tropomyosin and troponin are determined empirically, by titration to achieve maximal difference in ATPase activity when measured in the presence of 1 mM EGTA versus that measured in the presence of 0.2 mM $CaCl_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity ($pCa_{50}$), so a preliminary experiment is performed to test the response of the ATPase activity to free calcium concentrations in the range of $1\times10^{-4}$ M to $1\times10^{-8}$ M. Subsequently, the assay mixture is adjusted to the $pCa_{50}$ (typically $3\times10^{-7}$ M). Assays are performed by first preparing a dilution series of test compound, each with an assay mixture containing potassium Pipes, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, $MgCl_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation $y=Bottom+((Top-Bottom)/(1+((EC50/X)^{Hill})))$. The AC1.4 is defined as the concentration at which ATPase activity is 1.4-fold higher than the bottom of the dose curve.

Example 20

Myocyte Assays

20A. PREPARATION OF ADULT CARDIAC VENTRICULAR RAT MYOCYTES. Adult male Sprague-Dawley rats are anesthetized with a mixture of isoflurane gas and oxygen. Hearts are quickly excised, rinsed and the ascending aorta cannulated. Continuous retrograde perfusion is initiated on the hearts at a perfusion pressure of 60 cm $H_2O$. Hearts are first perfused with a nominally $Ca^{2+}$ free modified Krebs solution of the following composition: 110 mM NaCl, 2.6 mM KCL, 1.2 mM $KH_2PO_4$ $7H_2O$, 1.2 mM $MgSO_4$, 2.1 mM $NaHCO_3$, 11 mM glucose and 4 mM Hepes (all Sigma). This medium is not recirculated and is continually gassed with $O_2$. After approximately 3 minutes the heart is perfused with modified Krebs buffer supplemented with 3.3% collagenase (169 μ/mg activity, Class II, Worthington Biochemical Corp., Freehold, N.J.) and 25 μM final calcium concentration until the heart becomes sufficiently blanched and soft. The heart is removed from the cannulae, the atria and vessels discarded and the ventricles are cut into small pieces. The myocytes are dispersed by gentle agitation of the ventricular tissue in fresh collagenase containing Krebs prior to being gently forced through a 200 μm nylon mesh in a 50 cc tube. The resulting myocytes are resuspended in modified Krebs solution containing 25 μm calcium. Myocytes are made calcium tolerant by addition of a calcium solution (100 mM stock) at 10 minute intervals until 100 μM calcium is achieved. After 30 minutes the supernatant is discarded and 30-50 ml of Tyrode buffer (137 mM NaCL, 3.7 mM KCL, 0.5 mM MgCL, 11 mM glucose, 4 mM Hepes, and 1.2 mM $CaCl_2$, pH 7.4) is added to cells. Cells are kept for 60 min at 37° C. prior to initiating experiments and used within 5 hrs of isolation. Preparations of cells are used only if cells first passed QC criteria by responding to a standard (>150% of basal) and isoproterenol (ISO; >250% of basal). Additionally, only cells whose basal contractility is between 3 and 8% are used in the following experiments.

20B. ADULT VENTRICULAR MYOCYTE CONTRACTILITY EXPERIMENTS. Aliquots of Tyrode buffer containing myocytes are placed in perfusion chambers (series 20 RC-27NE; Warner Instruments) complete with heating platforms. Myocytes are allowed to attach, the chambers heated to 37° C., and the cells then perfused with 37° C. Tyrode buffer. Myocytes are field stimulated at 1 Hz in with platinum electrodes (20% above threshold). Only cells that have clear striations, and are quiescent prior to pacing are used for contractility experiments. To determine basal contractility, myocytes are imaged through a 40× objective and using a variable frame rate (60-240 Hz) charge-coupled device camera, the images are digitized and displayed on a computer screen at a sampling speed of 240 Hz. [Frame grabber, myopacer, acquisition, and analysis software for cell contractility are available from IonOptix (Milton, Mass.).] After a minimum 5 minute basal contractility period, test compounds (0.01-15 μM) are perfused on the myocytes for 5 minutes. After this time, fresh Tyrode buffer is perfused to determine compound washout characteristics. Using edge detection strategy, contractility of the myocytes and contraction and relaxation velocities are continuously recorded.

20C. CONTRACTILITY ANALYSIS. Three or more individual myocytes are tested per compound, using two or more different myocyte preparations. For each cell, twenty or more contractility transients at basal (defined as 1 min prior to compound infusion) and after compound addition, are averaged and compared. These average transients are analyzed to determine changes in diastolic length, and using the Ionwizard analysis program (IonOptix), fractional shortening (% decrease in the diastolic length), and maximum contraction and relaxation velocities (um/sec) are determined. Analysis of individual cells are combined. Increase in fractional shortening over basal indicates potentiation of myocyte contractility.

20D. CALCIUM TRANSIENT ANALYSIS: Fura loading: Cell permeable Fura-2 (Molecular Probes) is dissolved in equal amounts of pluronic (Mol Probes) and FBS for 10 min at RT. A 1 μM Fura stock solution is made in Tyrode buffer containing 500 mM probenecid (Sigma). To load cells, this solution is added to myocytes at RT. After 10 min. the buffer is removed, the cells washed with Tyrode containing probenecid and incubated at RT for 10 min. This wash and incubation is repeated. Simultaneous contractility and calcium measurements are determined within 40 min. of loading.

Imaging: A test compound is perfused on cells. Simultaneous contractility and calcium transient ratios are determined at baseline and after compound addition. Cells are digitally imaged and contractility determined as described above, using that a red filter in the light path to avoid interference with fluorescent calcium measurements. Acquisition, analysis software and hardware for calcium transient analysis are obtained from IonOptix. The instrumentation for fluorescence measurement includes a xenon arc lamp and a Hyperswitch dual excitation light source that alternates between 340 and 380 wavelengths at 100 Hz by a galvo-driven mirror. A liquid filled light guide delivers the dual excitation light to the microscope and the emission fluorescence is determined using a photomultiplier tube (PMT). The fluorescence system interface routes the PMT signal and the ratios are recorded using the IonWizard acquisition program.

Analysis: For each cell, ten or more contractility and calcium ratio transients at basal and after compound addition, where averaged and compared. Contractility average transients are analyzed using the Ionwizard analysis program to determine changes in diastolic length, and fractional shortening (% decrease in the diastolic length). The averaged calcium ratio transients are analyzed using the Ionwizard analysis program to determine changes in diastolic and systolic ratios and the 75% time to baseline ($T_{75}$).

20E. DURABILITY: To determine the durability of response, myocytes are challenged with a test compound for 25 minutes followed by a 2 min. washout period. Contractility response is compared at 5 and 25 min. following compound infusion.

20F. THRESHOLD POTENTIAL: Myocytes are field stimulated at a voltage approximately 20% above threshold. In these experiments the threshold voltage (minimum voltage to pace cell) is empirically determined, the cell paced at that threshold and then the test compound is infused. After the compound activity is at steady state, the voltage is decreased for 20 seconds and then restarted. Alteration of ion channels corresponds to increasing or lowering the threshold action potential.

20G. Hz FREQUENCY Contractility of myocytes is determined at 3 Hz as follows: a 1 min. basal time point followed by perfusion of the test compound for 5 min. followed by a 2 min. washout. After the cell contractility has returned completely to baseline the Hz frequency is decreased to 1. After an initial acclimation period the cell is challenged by the same compound. As this species, rat, exhibits a negative force frequency at 1 Hz, at 3 Hz the FS of the cell should be lower, but the cell should still respond by increasing its fractional shortening in the presence of the compound.

207H. ADDITIVE WITH ISOPROTERENOL: To demonstrate that a compound act via a different mechanism than the adrenergic stimulant isoproterenol, cells are loaded with fura-2 and simultaneous measurement of contractility and calcium ratios are determined. The myocytes are sequentially challenged with 5 μm a test compound, buffer, 2 nM isoproterenol, buffer, and a combination of a test compound and isoproterenol.

Example 21

In Vitro Model of Dose Dependent Cardiac Myosin ATPase Modulation

Bovine and rat cardiac myosins are purified from the respective cardiac tissues. Skeletal and smooth muscle myosins used in the specificity studies are purified from rabbit skeletal muscle and chicken gizzards, respectively. All myosins used in the assays are converted to a single-headed soluble form (S1) by a limited proteolysis with chymotrypsin. Other sarcomeric components: troponin complex, tropomyosin and actin are purified from bovine hearts (cardiac sarcomere) or chicken pectoral muscle (skeletal sarcomere).

Activity of myosins is monitored by measuring the rates of hydrolysis of ATP. Myosin ATPase is very significantly activated by actin filaments. ATP turnover is detected in a coupled enzymatic assay using pyruvate kinase (PK) and lactate dehydrogenase (LDH). In this assay each ADP produced as a result of ATP hydrolysis is recycled to ATP by PK with a simultaneous oxidation of NADH molecule by LDH. NADH oxidation can be conveniently monitored by decrease in absorbance at 340 nm wavelength.

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1 \times 10^{-4}$ M to $1 \times 10^{-8}$ M.

The protein components specific to this assay are bovine cardiac myosin subfragment-1 (typically 0.5 μM), bovine cardiac actin (14 μM), bovine cardiac tropomyosin (typically 3 μM), and bovine cardiac troponin (typically 3-8 μM). The exact concentrations of tropomyosin and troponin are determined empirically, by titration to achieve maximal difference in ATPase activity when measured in the presence of 1 mM EGTA versus that measured in the presence of 0.2 mM $CaCl_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity ($pCa_{50}$), so a preliminary experiment is performed to test the response of the ATPase activity to free calcium concentrations in the range of $1 \times 10^{-4}$ M to $1 \times 10^{-8}$ M. Subsequently, the assay mixture is adjusted to the $pCa_{50}$ (typically $3 \times 10^{-7}$ M). Assays are performed by first preparing a dilution series of test compound, each with an assay mixture containing potassium Pipes, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, $MgCl_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top-Bottom)/(1+((EC50/X)^Hill))). The AC1.4 is defined as the concentration at which ATPase activity is 1.4-fold higher than the bottom of the dose curve.

Ability of a compound to activate cardiac myosin is evaluated by the effect of the compound on the actin stimulated ATPase of S1 subfragment. Actin filaments in the assay are decorated with troponin and tropomyosin and Ca++ concentration is adjusted to a value that would result in 50% of maximal activation. S1 ATPase is measured in the presence of a dilution series of the compound. Compound concentration required for 40% activation above the ATPase rate measured in the presence of control (equivalent volume of DMSO) is reported as $AC_{40}$.

Example 22

In Vivo Fractional Shortening Assay

22A. ANIMALS Male Sprague Dawley rats from Charles River Laboratories (275-350 g) are used for bolus efficacy and infusion studies. Heart failure animals are described below. They are housed two per cage and have access to food and water ad libitum. There is a minimum three-day acclimation period prior to experiments.

22B. ECHOCARDIOGRAPHY Animals are anesthetized with isoflurane and maintained within a surgical plane throughout the procedure. Core body temperature is maintained at 37° C. by using a heating pad. Once anesthetized, animals are shaven and hair remover is applied to remove all traces of fur from the chest area. The chest area is further prepped with 70% ETOH and ultrasound gel is applied. Using a GE System Vingmed ultrasound system (General Electric Medical Systems), a 10 MHz probe is placed on the chest wall and images are acquired in the short axis view at the level of the papillary muscles. 2-D M-mode images of the left ventricle are taken prior to, and after, compound bolus injection or infusion. In vivo fractional shortening ((end diastolic diameter—end systolic diameter)/end diastolic diameter× 100) is determined by analysis of the M-mode images using the GE EchoPak software program.

22C. BOLUS AND INFUSION EFFICACY For bolus and infusion protocols, fractional shortening is determined using echocardiography as described above. For bolus and infusion protocols, five pre-dose M-Mode images are taken at 30 second intervals prior to bolus injection or infusion of compounds. After injection, M-mode images are taken at 1 min and at five minute intervals thereafter up to 30 min. Bolus injection (0.5-5 mg/kg) or infusion is via a tail vein catheter. Infusion parameters are determined from pharmacokinetic profiles of the compounds. For infusion, animals received a 1 minute loading dose immediately followed by a 29 minute infusion dose via a tail vein catheter. The loading dose is calculated by determining the target concentration×the steady state volume of distribution. The maintenance dose concentration is determined by taking the target concentration×the clearance. Compounds are formulated in 25% cavitron vehicle for bolus and infusion protocols. Blood samples are taken to determine the plasma concentration of the compounds.

Example 23

Hemodynamics in Normal and Heart Failure Animals

Animals are anesthetized with isoflurane, maintained within a surgical plane, and then shaven in preparation for catheterization. An incision is made in the neck region and the right carotid artery cleared and isolated. A 2 French Millar Micro-tip Pressure Catheter (Millar Instruments, Houston, Tex.) is cannulated into the right carotid artery and threaded past the aorta and into the left ventricle. End diastolic pressure readings, max+/−dp/dt, systolic pressures and heart rate are determined continuously while compound or vehicle is infused. Measurements are recorded and analyzed using a PowerLab and the Chart 4 software program (ADInstruments, Mountain View, Calif.). Hemodynamics measurements are performed at a select infusion concentration. Blood samples are taken to determine the plasma concentration of the compounds.

Example 24

Left Coronary Artery Occlusion Model of Congestive Heart Failure

24A. ANIMALS Male Sprague-Dawley CD (220-225 g; Charles River) rats are used in this experiment. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study. The animals are fasted overnight prior to surgery.

24B. OCCLUSION PROCEDURE Animals are anaesthetized with ketamine/xylazine (95 mg/kg and 5 mg/kg) and intubated with a 14-16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10-15 cm $H_2O$ and respiratory rate 60-110 breaths/min. 100% $O_2$ is delivered to the animals by the ventilator. The surgical site is scrubbed with surgical scrub and alcohol. An incision is made over the rib cage at the $4^{th}$-$5^{th}$ intercostal space. The underlying muscles are dissected with care to avoid the lateral thoracic vein, to expose the intercostal muscles. The chest cavity is entered through $4^{th}$-$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. The left coronary artery is occluded by tying the suture around the artery ("LCO"). Sham animals are treated the same, except that the suture is not tied. The incision is closed in three layers. The rat is ventilated until able to ventilate on its own. The rats are extubated and allowed to recover on a heating pad. Animals receive buprenorphine (0.01-0.05 mg/kg SQ) for post operative analgesia. Once awake, they are returned to their cage. Animals are monitored daily for signs of infection or distress. Infected or moribund animals are euthanized. Animals are weighed once a week.

24C. EFFICACY ANALYSIS Approximately eight weeks after infarction surgery, rats are scanned for signs of myocardial infarction using echocardiography. Only those animals with decreased fractional shortening compared to sham rats are utilized further in efficacy experiments. In all experiments, there are four groups, sham+vehicle, sham+compound, LCL+vehicle and LCL+compound. At 10-12 weeks post LCL, rats are infused at a select infusion concentration. As before, five pre-dose M-Mode images are taken at 30 second intervals prior to infusion of compounds and M-mode images are taken at 30 second intervals up to 10 minutes and every minute or at five minute intervals thereafter. Fractional shortening is determined from the M-mode images. Comparisons between the pre-dose fractional shortening and compound treatment are performed by ANOVA and a post-hoc Student-Newman-Keuls. Animals are allowed to recover and within 7-10 days, animals are again infused with compounds using the hemodynamic protocol to determine hemodynamic changes of the compounds in heart failure animals. At the end to the infusion, rats are killed and the heart weights determined.

When tested as described in Examples 18-24, compounds of Formula I are shown to have the desired activity.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound represented by Formula I:

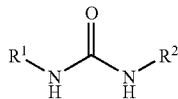

Formula I wherein:

$R^1$ is represented by Formula II:

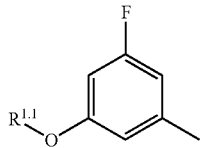

Formula II wherein:

$R^{1.1}$ is 1-acyl-pyrrolidin-3-yl, 1-alkoxycarbonyl-pyrrolidin-3-yl, 1-amidino-pyrrolidin-3-yl, 1-sulfonyl-pyrrolidin-3-yl, 3-oxo-tetrahydro-pyrrolo[1,2-c]oxazol-6-yl, 1-acyl-piperidin-3-yl, 1-alkoxycarbonyl-piperidin-3-yl, 1-amidino-piperidin-3-yl or 1-sulfonyl-piperidin-3-yl, each of which is optionally substituted with an additional lower alkoxy or lower alkoxyalkyl ring substituent;

$R^2$ is pyridin-3-yl or pyridin-3-yl substituted with one or two substituents chosen from lower alkoxy and lower alkyl;

or a pharmaceutically acceptable salt thereof.

2. The compound of claim 1 where $R^{1.1}$ is 1-acetyl-piperidin-3-yl, 1-methoxyacetyl-piperidin-3-yl, 1-(azetidine-1-carbonyl)-piperidin-3-yl, 1-methoxycarbonyl-piperidin-3-yl, 1-ethoxycarbonyl-piperidin-3-yl, 1-dimethylaminocarbonyl-piperidin-3-yl, 1-methanesulfonyl-piperidin-3-yl, 1-(ethane-2-sulfonyl)-piperidin-3-yl 1-(propane-2-sulfonyl)-piperidin-3-yl, 1-(azetidin-1-yl-sulfonyl)-piperidin-3-yl, 1-dimethylaminosulfonyl-piperidin-3-yl, 1-($N^1$-azetidin-1-yl-$N^2$-cyano-amidino)-piperidin-3-yl, 1-($N^2$-cyano-$N^1$,$N^1$-dimethyamidino)-piperidine-3-yl, 1-acetyl-pyrrolidin-3-yl, 1-acetyl-5-methoxymethyl-pyrrolidin-3-yl, 1-methoxyacetyl-pyrrolidin-3-yl, 1-(azetidine-1-carbonyl)-pyrrolidin-3-yl, 1-methoxycarbonyl-pyrrolidin-3-yl, 1-methoxycarbonyl-2-methoxymethyl-pyrrolidin-4-yl, 1-methanesulfonyl-pyrrolidin-3-yl, 1-(ethane-2-sulfonyl)-pyrrolidin-3-yl, 1-(ethane-2-sulfonyl)-4-methoxy-pyrrolidin-3-yl, 1-(ethane-2-sulfonyl)-5-methoxymethyl-pyrrolidin-3-yl, 1-(propane-2-sulfonyl)-pyrrolidin-3-yl, 1-(azetidin-1-yl-sulfonyl)-pyrrolidin-3-yl, 1-dimethylaminosulfonyl-pyrrolidin-3-yl, 1-dimethylaminosulfonyl-2-methoxymethyl-pyrrolidin-4-yl, 1-($N^1$-azetidin-1-yl-$N^2$-cyano-amidino)-pyrrolidin-3-yl, 1-($N^2$-cyano-$N^1$,$N^1$-dimethyamidino)-pyrrolidin-3-yl, or 3-oxo-tetrahydro-pyrrolo[1,2-c]oxazol-6-yl.

3. The compound of claim 1 where $R^{1.1}$ is 1-acyl-pyrrolidin-3-yl, 1-acetyl-5-methoxymethyl-pyrrolidin-3-yl, 1-sulfonyl-pyrrolidin-3-yl, 3-oxo-tetrahydro-pyrrolo[1,2-c]oxazol-6-yl, 1-alkoxycarbonyl-piperidin-3-yl or 1-sulfonyl-piperidin-3-yl.

4. The compound of claim 3 where $R^{1.1}$ is 1-methoxycarbonyl-2-methoxymethyl-pyrrolidin-4-yl, 1-(ethane-2-sulfonyl)-pyrrolidin-3-yl, 1-(ethane-2-sulfonyl)-5-methoxymethyl-pyrrolidin-3-yl, 1-dimethylaminosulfonyl-pyrrolidin-3-yl, 1-dimethylaminosulfonyl-2-methoxymethyl-pyrrolidin-4-yl, 3-oxo-tetrahydro-pyrrolo[1,2-c]oxazol-6-yl, 1-methoxycarbonyl-piperidin-3-yl, 1-methanesulfonyl-piperidin-3-yl, or 1-(ethane-2-sulfonyl)-piperidin-3-yl.

5. The compound of claim 1 where $R^2$ is pyridin-3-yl or 6-methyl-pyridin-3-yl.

6. A compound of claim 1 wherein the compound represented by Formula I is selected from:

1-[3-(1-Acetyl-piperidin-3-yloxy)-5-fluoro-phenyl]-3-(6-methoxy-pyridin-3-yl)-urea;
1-[3-(1-Acetyl-piperidin-3-yloxy)-5-fluoro-phenyl]-3-pyridin-3-yl-urea;
1-[3-Fluoro-5-(1-methanesulfonyl-piperidin-3-yloxy)-phenyl]-3-pyridin-3-yl-urea;
(R)-1-[3-(1-Acetyl-piperidin-3-yloxy)-5-fluoro-phenyl]-3-(6-methoxy-pyridin-3-yl)-urea;
(S)-1-[3-(1-Acetyl-piperidin-3-yloxy)-5-fluoro-phenyl]-3-(6-methoxy-pyridin-3-yl)-urea;
(R)-1-[3-(1-Acetyl-piperidin-3-yloxy)-5-fluoro-phenyl]-3-pyridin-3-yl-urea;
(S)-1-[3-(1-Acetyl-piperidin-3-yloxy)-5-fluoro-phenyl]-3-pyridin-3-yl-urea;
(R)-3-{3-Fluoro-5-[3-(6-methyl-pyridin-3-yl)-ureido]-phenoxy}-piperidine-1-carboxylic acid methyl ester;
(S)-3-{3-Fluoro-5-[3-(6-methyl-pyridin-3-yl)-ureido]-phenoxy}-piperidine-1-carboxylic acid methyl ester;
(R)-1-[3-Fluoro-5-(1-methanesulfonyl-piperidin-3-yloxy)-phenyl]-3-pyridin-3-yl-urea;
(S)-1-[3-Fluoro-5-(1-methanesulfonyl-piperidin-3-yloxy)-phenyl]-3-pyridin-3-yl-urea;
(R)-1-[3-(1-Acetyl-piperidin-3-yloxy)-5-fluoro-phenyl]-3-(6-methyl-pyridin-3-yl)-urea;
(S)-1-[3-(1-Acetyl-piperidin-3-yloxy)-5-fluoro-phenyl]-3-(6-methyl-pyridin-3-yl)-urea;
(R)-1-[3-Fluoro-5-(1-methanesulfonyl-piperidin-3-yloxy)-phenyl]-3-(6-methyl-pyridin-3-yl)-urea;
(S)-1-[3-Fluoro-5-(1-methanesulfonyl-piperidin-3-yloxy)-phenyl]-3-(6-methyl-pyridin-3-yl)-urea;
(R)-1-{3-Fluoro-5-[1-(propane-2-sulfonyl)-piperidin-3-yloxy]-phenyl}-3-pyridin-3-yl-urea;
(S)-1-{3-Fluoro-5-[1-(propane-2-sulfonyl)-piperidin-3-yloxy]-phenyl}-3-pyridin-3-yl-urea;

(R)-1-{3-Fluoro-5-[1-(propane-2-sulfonyl)-piperidin-3-yloxy]-phenyl}-3-(6-methyl-pyridin-3-yl)-urea;
(S)-1-{3-Fluoro-5-[1-(propane-2-sulfonyl)-piperidin-3-yloxy]-phenyl}-3-(6-methyl-pyridin-3-yl)-urea;
(R)-1-[3-(1-ethanesulfonyl-piperidin-3-yloxy)-5-fluoro-phenyl]-3-pyridin-3-yl-urea;
(S)-1-[3-(1-ethanesulfonyl-piperidin-3-yloxy)-5-fluoro-phenyl]-3-pyridin-3-yl-urea;
(R)-1-[3-(1-Ethanesulfonyl-piperidin-3-yloxy)-5-fluoro-phenyl]-3-(6-methyl-pyridin -3-yl)-urea;
(S)-1-[3-(1-Ethanesulfonyl-piperidin-3-yloxy)-5-fluoro-phenyl]-3-(6-methyl-pyridin -3-yl)-urea;
(R)-3-[3-Fluoro-5-(pyridin-3-yl-ureido)-phenoxy]-piperidine-1-N,N-dimethyl-N -cyano-carboxamidine;
(S)-3-[3-Fluoro-5-(pyridin-3-yl-ureido)-phenoxy]-piperidine-1-N,N-dimethyl-N -cyano-carboxamidine;
(R)-3-[3-Fluoro-5-(2-methyl-pyridin-5-yl-ureido)-phenoxy]-piperidine-1-N,N  -dimethyl-N-cyano-carboxamidine;
(S)-3-[3-Fluoro-5-(2-methyl-pyridin-5-yl-ureido)-phenoxy]-piperidine-1-N,N  -dimethyl-N-cyano-carboxamidine;
(R)-1-[3-(1-Ethanesulfonyl-piperidin-3-yloxy)-5-fluoro-phenyl]-3-(6-methyl -pydridin-3-yl)-urea;
(S)-1-[3-(1-Ethanesulfonyl-piperidin-3-yloxy)-5-fluoro-phenyl]-3-(6-methyl -pydridin-3-yl)-urea;
(R)-3-[3-Fluoro-5-(3-pyridin-3-yl-ureido)-phenoxy]-pyrrolidine-1-sulfonic acid dimethylamide;
(S)-3-[3-Fluoro-5-(3-pyridin-3-yl-ureido)-phenoxy]-pyrrolidine-1-sulfonic acid dimethylamide;
(R)-3-{3-Fluoro-5-[3-(6-methyl-pyridin-3-yl)-ureido]-phenoxy}-pyrrolidine-1-sulfonic acid dimethylamide;
(S)-3-{3-Fluoro-5-[3-(6-methyl-pyridin-3-yl)-ureido]-phenoxy}-pyrrolidine-1-sulfonic acid dimethylamide;
1-[(R)-3-(1-Acetyl-(R)-5-methoxymethyl-pyrrolidin-3-yloxy)-5-fluoro-phenyl]-3-pyridin-3-yl-urea;
1-[(S)-3-(1-Acetyl-(S)-5-methoxymethyl-pyrrolidin-3-yloxy)-5-fluoro-phenyl]-3-pyridin-3-yl-urea;
1-[(R)-3-(1-Acetyl-(S)-5-methoxymethyl-pyrrolidin-3-yloxy)-5-fluoro-phenyl]-3-pyridin-3-yl-urea;
1-[(S)-3-(1-Acetyl-(R)-5-methoxymethyl-pyrrolidin-3-yloxy)-5-fluoro-phenyl]-3-pyridin-3-yl-urea;
4-{3-fluoro-5-[(R)-3-(6-methyl-pyridin-3-yl)-ureido]phenoxy}-(R)-2-methoxymethyl  -pyrrolidine-1-carboxylic acid methyl ester;
4-{3-fluoro-5-[(S)-3-(6-methyl-pyridin-3-yl)-ureido]phenoxy}-(S)-2-methoxymethyl -pyrrolidine-1-carboxylic acid methyl ester;
4-{3-fluoro-5-[(R)-3-(6-methyl-pyridin-3-yl)-ureido]phenoxy}-(S)-2-methoxymethyl  -pyrrolidine-1-carboxylic acid methyl ester;
4-{3-fluoro-5-[(S)-3-(6-methyl-pyridin-3-yl)-ureido]phenoxy}-(R)-2-methoxymethyl -pyrrolidine-1-carboxylic acid methyl ester;
1-[(R)-3-(1-Acetyl-(R)-5-methoxymethyl-pyrrolidin-3-yloxy)-5-fluoro-phenyl]-3-(6-methyl-pyridin-3-yl)-urea;
1-[(S)-3-(1-Acetyl-(S)-5-methoxymethyl-pyrrolidin-3-yloxy)-5-fluoro-phenyl]-3-(6-methyl-pyridin-3-yl)-urea;
1-[(R)-3-(1-Acetyl-(S)-5-methoxymethyl-pyrrolidin-3-yloxy)-5-fluoro-phenyl]-3-(6-methyl-pyridin-3-yl)-urea; and
1-[(S)-3-(1-Acetyl-(R)-5-methoxymethyl-pyrrolidin-3-yloxy)-5-fluoro-phenyl]-3-(6-methyl-pyridin-3-yl)-urea 3-[3-Fluoro-5-(3-pyridin-3-yl-ureido)-phenoxy]-piperidine-1-carboxylic acid methyl ester.

7. A compound of claim 1 wherein the compound represented by Formula I is selected from:
(S)-3-{3-Fluoro-5-[3-(6-methyl-pyridin-3-yl)-ureido]-phenoxy}-pyrrolidine-1-sulfonic acid dimethylamide;
(R)-3-{3-Fluoro-5-[3-(6-methyl-pyridin-3-yl)-ureido]-phenoxy}-pyrrolidine-1-sulfonic acid dimethylamide;
(S)-3-[3-Fluoro-5-(2-methyl-pyridin-5-yl-ureido)-phenoxy]-pyrrolidine-1-N,N   -dimethyl-N-cyano-carboxam idine;
(R)-3-[3-Fluoro-5-(2-methyl-pyridin-5-yl-ureido)-phenoxy]-pyrrolidine-1-N,N  -dimethyl-N-cyano-carboxamidine;
(S)-3-[3-Fluoro-5-(3-pyridin-3-yl-ureido)-phenoxy]-pyrrolidine-1-sulfonic acid dimethylamide;
(R)-3-[3-Fluoro-5-(3-pyridin-3-yl-ureido)-phenoxy]-pyrrolidine-1-sulfonic acid dimethylamide;
(S)-3-[3-Fluoro-5-(pyridin-2-yl-ureido)-phenoxy]-pyrrolidine-1-N,N-dimethyl-N -cyano-carboxamidine;
(R)-3-[3-Fluoro-5-(pyridin-2-yl-ureido)-phenoxy]-pyrrolidine-1-N,N-dimethyl-N -cyano-carboxamidine;
(S)-3-[3-Fluoro-5-(3-pyridin-3-yl-ureido)-phenoxy]-pyrrolidine-1-carboxylic acid methyl ester;
(R)-3-[3-Fluoro-5-(3-pyridin-3-yl-ureido)-phenoxy]-pyrrolidine-1-carboxylic acid methyl ester;
(S)-3-{3-Fluoro-5-[3-(6-methyl-pyridin-3-yl)-ureido]-phenoxy}-pyrrolidine-1-carboxylic acid methyl ester;
(R)-3-{3-Fluoro-5-[3-(6-methyl-pyridin-3-yl)-ureido]-phenoxy}-pyrrolidine-1-carboxylic acid methyl ester;
(S)-1-{3-Fluoro-5-[1-(propane-2-sulfonyl)-pyrrolidin-3-yloxy]-phenyl}-3-pyridin-3-yl-urea;
(R)-1-{3-Fluoro-5-[1-(propane-2-sulfonyl)-pyrrolidin-3-yloxy]-phenyl}-3-pyridin-3-yl-urea;
(S)-1-{3-Fluoro-5-[1-(propane-2-sulfonyl)-pyrrolidin-3-yloxy]-phenyl}-3-(6-methyl -pyridin-3-yl)-urea;
(R)-1-{3-Fluoro-5-[1-(propane-2-sulfonyl)-pyrrolidin-3-yloxy]-phenyl}-3-(6-methyl-pyridin-3-yl)-urea;
(S)-1-{3-Fluoro-5-[1-(ethane-2-sulfonyl)-pyrrolidin-3-yloxy]-phenyl}-3-pyridin-3-yl-urea;
(R)-1-{3-Fluoro-5-[1-(ethane-2-sulfonyl)-pyrrolidin-3-yloxy]-phenyl}-3-pyridin-3-yl-urea;
(S)-1-{3-Fluoro-5-[1-(ethane-2-sulfonyl)-pyrrolidin-3-yloxy]-phenyl}-3-(6-methyl -pyridin-3-yl)-urea;
(R)-1-{3-Fluoro-5-[1-(ethane-2-sulfonyl)-pyrrolidin-3-yloxy]-phenyl}-3-(6-methyl -pyridin-3-yl)-urea;
(S)-1-{3-Fluoro-5-[1-(methane-2-sulfonyl)-pyrrolidin-3-yloxy]-phenyl}-3-(6-methyl-pyridin-3-yl)-urea;
(R)-1-{3-Fluoro-5-[1-(methane-2-sulfonyl)-pyrrolidin-3-yloxy]-phenyl}-3-(6-methyl-pyridin-3-yl)-urea;
(S)-4-{3-Fluoro-5-[3-(6-methyl-pyridin-3-yl)-ureido]-phenoxy}-[(S)-2-methoxymethyl]-pyrrolidine-1-sulfonic acid dimethylamide;
(R)-4-{3-Fluoro-5-[3-(6-methyl-pyridin-3-yl)-ureido]-phenoxy}-[(R)-2-methoxymethyl]-pyrrolidine-1-sulfonic acid dimethylamide;
(S)-4-{3-Fluoro-5-[3-(6-methyl-pyridin-3-yl)-ureido]-phenoxy}-[(R)-2-methoxymethyl]-pyrrolidine-1-sulfonic acid dimethylamide;
(R)-4-{3-Fluoro-5-[3-(6-methyl-pyridin-3-yl)-ureido]-phenoxy}-[(S)-2-methoxymethyl]-pyrrolidine-1-sulfonic acid dimethylamide;
(S)-4-{3-Fluoro-5-[3-(6-methyl-pyridin-3-yl)-ureido]-phenoxy}-[(S)-2-methoxymethyl]-pyrrolidine-1-carboxylic acid methyl ester;

(R)-4-{3-Fluoro-5-[3-(6-methyl-pyridin-3-yl)-ureido]-phenoxy}-[(R)-2-methoxymethyl]-pyrrolidine-1-carboxylic acid methyl ester;

(S)-4-{3-Fluoro-5-[3-(6-methyl-pyridin-3-yl)-ureido]-phenoxy}-[(R)-2-methoxymethyl]-pyrrolidine-1-carboxylic acid methyl ester;

(R)-4-{3-Fluoro-5-[3-(6-methyl-pyridin-3-yl)-ureido]-phenoxy}-[(S)-2-methoxymethyl]-pyrrolidine-1-carboxylic acid methyl ester;

(S)-1-{3-(1-Ethanesulfonyl-[(S)-4-methoxy]-pyrrolidin-3-yloxy)-5-fluoro-phenyl}-3-(6-methyl-pyridin-3-yl)-urea;

(R)-1-{3-(1-Ethanesulfonyl-[(R)-4-methoxy]-pyrrolidin-3-yloxy)-5-fluoro-phenyl}-3-(6-methyl-pyridin-3-yl)-urea;

(S)-1-{3-(1-Ethanesulfonyl-[(R)-4-methoxy]-pyrrolidin-3-yloxy)-5-fluoro-phenyl}-3-(6-methyl-pyridin-3-yl)-urea;

(R)-1-{3-(1-Ethanesulfonyl-[(S)-4-methoxy]-pyrrolidin-3-yloxy)-5-fluoro-phenyl}-3-(6-methyl-pyridin-3-yl)-urea;

(S)-1-{3-(1-Ethanesulfonyl-[(S)-5-methoxymethyl]-pyrrolidin-3-yloxy)-5-fluoro -phenyl}-3-pyridin-3-yl-urea;

(R)-1-{3-(1-Ethanesulfonyl-[(R)-5-methoxymethyl]-pyrrolidin-3-yloxy)-5-fluoro -phenyl}-3-pyridin-3-yl-urea;

(S)-1-{3-(1-Ethanesulfonyl-[(R)-5-methoxymethyl]-pyrrolidin-3-yloxy)-5-fluoro -phenyl}-3-pyridin-3-yl-urea;

(R)-1-{3-(1-Ethanesulfonyl-[(S)-5-methoxymethyl]-pyrrolidin-3-yloxy)-5-fluoro -phenyl}-3-pyridin-3-yl-urea;

(S)-1-{3-(1-Ethanesulfonyl-[(S)-5-methoxymethyl]-pyrrolidin-3-yloxy)-5-fluoro    -phenyl}-3-(6-methyl-pyridin-3-yl)-urea;

(R)-1-{3-(1-Ethanesulfonyl-[(R)-5-methoxymethyl]-pyrrolidin-3-yloxy)-5-fluoro    -phenyl}-3-(6-methyl-pyridin-3-yl)-urea;

(S)-1-{3-(1-Ethanesulfonyl-[(R)-5-methoxymethyl]-pyrrolidin-3-yloxy)-5-fluoro    -phenyl}-3-(6-methyl-pyridin-3-yl)-urea;

(R)-1-{3-(1-Ethanesulfonyl-[(S)-5-methoxymethyl]-pyrrolidin-3-yloxy)-5-fluoro    -phenyl}-3-(6-methyl-pyridin-3-yl)-urea;

1-[3-Fluoro-5-(S)-(3-oxo-(S)-tetrahydro-pyrrolo[1,2-c]oxazol-6-yloxy)-phenyl]-3-pyridin-3-yl-urea;

1-[3-Fluoro-5-(R)-(3-oxo-(R)-tetrahydro-pyrrolo[1,2-c]oxazol-6-yloxy)-phenyl]-3-pyridin-3-yl-urea;

1-[3-Fluoro-5-(S)-(3-oxo-(R)-tetrahydro-pyrrolo[1,2-c]oxazol-6-yloxy)-phenyl]-3-pyridin-3-yl-urea;

1-[3-Fluoro-5-(R)-(3-oxo-(S)-tetrahydro-pyrrolo[1,2-c]oxazol-6-yloxy)-phenyl]-3-pyridin-3-yl-urea;

1-[3-Fluoro-5-(S)-(3-oxo-(S)-tetrahydro-pyrrolo[1,2-c]oxazol-6-yloxy)-phenyl]-3-(6-methyl-pyridin-3-yl)-urea;

1-[3-Fluoro-5-(R)-(3-oxo-(R)-tetrahydro-pyrrolo[1,2-c]oxazol-6-yloxy)-phenyl]-3-(6-methyl-pyridin-3-yl)-urea;

1-[3-Fluoro-5-(S)-(3-oxo-(R)-tetrahydro-pyrrolo[1,2-c]oxazol-6-yloxy)-phenyl]-3-(6-methyl-pyridin-3-yl)-urea; and 1-[3-Fluoro-5-(R)-(3-oxo-(S)-tetrahydro-pyrrolo[1,2-c]oxazol-6-yloxy)-phenyl]-3-(6-methyl-pyridin-3-yl)-urea.

8. A compound of claim 1 wherein the compound represented by Formula I is selected from:

(R)-1-[3-(1-Acetyl-piperidin-3-yloxy)-5-fluoro-phenyl]-3-pyridin-3-yl-urea;

(R)-3-{3-Fluoro-5-[3-(6-methyl-pyridin-3-yl)-ureido]-phenoxy}-piperidine-1-carboxylic acid methyl ester;

(S)-3-{3-Fluoro-5-[3-(6-methyl-pyridin-3-yl)-ureido]-phenoxy}-piperidine-1-carboxylic acid methyl ester;

(S)-3-[3-Fluoro-5-(3-pyrldin-3-yl-ureido)-phenoxy]-pyrrolidlne-1-sulfonic acid dimethylamide;

1-[(R)-3-(1-Acetyl-(R)-5-methoxymethyl-pyrrodin-3-yloxy)-5-fluoro-phenyl]-3-pyridin-3-yl-urea;

4-{3-fluoro-5-[(R)3-(6-methyl-pyridin-3-yl)-ureido]phenoxy}-(R)-2-methoxymethyl -pyrrolidine-1-carboxylic acid methyl ester;

(S)-1-[3-(1-Ethanesulonyl-piperidin-3-yloxy)-5-fluoro-phenyl]-3-(6methyl -pydridin-3-yl)-urea;

(R)-1-{3-Fluoro-5-[3-(6-methyl-pyridin-3-yl)-ureido]-phenoxy}-piperidine-1-carboxylic acid methyl ester;

(S)-3-{3-Fluoro-5-[3-(6-methyl-pyridin-3-yl)-ureido]-phenoxy}-piperidine-1-carboxylic acid methyl ester;

(S)-3-{3-Fluoro-5-[3-(6-methyl-pyridin-3-yl)-ureido]-phenoxy}-pyrrolidine-1-carboxylic acid methyl ester;

(R)-3-{3-Fluoro-5-[3-(6-methyl-pyridin-3-yl)-ureido]-phenoxy}-pyrrolidine-1-carboxylic acid methyl ester;

(S)-1-[3-Fluoro-5-(1-methanesulfonyl-piperidin-3-yloxy)-phenyl]-3-pyridin-3-yl -urea;

(R)-3-[3-Fluoro-5-(3-pyridin-3-yl-ureido)-phenoxy]-pyrrolidine-1-sulfonic acid dimethylamide;

(R)-1-{3-Fluoro-5-[1-(ethane-2-sulfonyl)-pyrrolidin-3-yloxy]-phenyl}-3-(6-methyl -pyridin-3-yl)-urea;

(S)-4-{3-Fluoro-5-[3-(6-methyl-pyridin-3-yl)-ureido]-phenoxy}-[(S)-2-methoxymethyl]-pyrrolidine-1-sulfonic acid dimethylamide;

(S)-4-{3-Fluoro-5-[3-(6-methyl-pyridin-3-yl)-ureido]-phenoxy}-[(S)-2-methoxymethyl]-pyrrolidine-1-carboxylic acid methyl ester;

(R)-1-{3-(1-Ethanesulfonyl-[(S)-5-methoxymethyl]-pyrrolidin-3-yloxy)-5-fluoro -phenyl}-3-pyridin-3-yl-urea;

1-[3-Fluoro-5-(R)-(3-oxo-(S)-tetrahydro-pyrrolo[1,2-c]oxazol-6-yloxy)-phenyl]-3-pyridin-3-yl-urea; and 1-[3-Fluoro-5-(R)-(3-oxo-(S)-tetrahydro-pyrrolo[1,2-c]oxazol-6-yloxy)-phenyl]-3-(6-methyl-pyridin-3-yl)-urea.

* * * * *